(12) United States Patent
Baell et al.

(10) Patent No.: US 7,553,809 B2
(45) Date of Patent: *Jun. 30, 2009

(54) FC RECEPTOR MODULATORS AND USES THEREOF

(75) Inventors: Jonathan B. Baell, Ivanhoe (AU); Thomas P. J. Garrett, Brunswick (AU); P. Mark Hogarth, Williamstown (AU); Barry R. Matthews, Olinda (AU); Thomas D. McCarthy, East Malvern (AU); Geoffrey A. Pietersz, Greensborough (AU); Maree S. Powell, Lysterfield (AU); Ian F. C. McKenzie, Pt. Lonsdale (AU); Kelly F. Maxwell, Singapore (SG); Vidana Epa, Coburg (AU)

(73) Assignee: Ilexus Pty Limited, Heidelberg, Victoria (AU)

( * ) Notice: Subject to any disclaimer, the term of this patent is extended or adjusted under 35 U.S.C. 154(b) by 411 days.

This patent is subject to a terminal disclaimer.

(21) Appl. No.: 10/861,227

(22) Filed: Jun. 3, 2004

(65) Prior Publication Data

US 2006/0057144 A1 Mar. 16, 2006

Related U.S. Application Data

(63) Continuation-in-part of application No. 09/995,277, filed on Nov. 26, 2001, now Pat. No. 6,835,753, which is a continuation of application No. 09/393,598, filed on Sep. 10, 1999, now Pat. No. 6,355,683, said application No. 10/861,227 is a continuation-in-part of application No. 10/687,109, filed on Oct. 15, 2003, now abandoned, which is a continuation of application No. 09/245,764, filed on Feb. 5, 1999, now Pat. No. 6,675,105.

(60) Provisional application No. 60/099,855, filed on Sep. 11, 1998, provisional application No. 60/131,938, filed on Apr. 30, 1999, provisional application No. 60/148,479, filed on Aug. 11, 1999, provisional application No. 60/073,972, filed on Feb. 6, 1998, provisional application No. 60/099,994, filed on Sep. 11, 1998.

(51) Int. Cl.
 *A01N 61/00* (2006.01)
(52) U.S. Cl. ............................................ 514/2
(58) Field of Classification Search .................... 703/11
 See application file for complete search history.

(56) References Cited

U.S. PATENT DOCUMENTS

| 4,686,282 | A |   | 8/1987  | Hahn |          |
|-----------|---|---|---------|------|----------|
| 4,752,601 | A |   | 6/1988  | Hahn |          |
| 5,824,487 | A | * | 10/1998 | Ravetch et al. | 435/7.8 |
| 6,503,509 | B1| * | 1/2003  | Vilen et al. | 424/153.1 |
| 6,835,753 | B2| * | 12/2004 | Baell et al. | 514/568 |

FOREIGN PATENT DOCUMENTS

| SU |    750960 A | 4/1982  |
|----|-------------|---------|
| WO | WO 86/01211 A | 2/1986 |
| WO | WO 95/28959 | 11/1995 |
| WO | WO 96/08512 | 3/1996  |
| WO | WO 97/40033 A | 10/1997 |
| WO | WO 99/40117 A | 8/1999  |

OTHER PUBLICATIONS

Burmeister et al., *Nature*, 372:379-383 (1994).
Burmeister et al., *Nature*, 372:336-343 (1994).
Chemical Abstracts CA:55:1138e (1955).
Garman et al., *Cell*, 95:951-961 (1998).
Holm et al., *Nucleic Acids Research*, 26(1):316-319 (1998).
Holm et al., *Science*, 273:595-602 (1996).
Holm et al., *J. Mol. Biol.*, 233:123-138 (1993).
Huang et al., *Biopolymers*, 43(5):367-382 (1997).
Huber et al., *J. Mol. Biol.*, 230:1077-1088 (1993).
Hulett et al., *Advances in Immunology*, 57:1-127 (1994).
Knegtel et al., *J. Mol. Biol.*, 266:424-440 (1996).
Kwack et al., "Functional Consequences of the Interaction Between T-cell Antigen Receptors and FcγRs on T Cells", Immunology Letters, 44 (1995) pp. 139-143, Elsevier Science B.V.
Maxwell et al., *Nature Structural Biology*, 6(5):437-442 (1999).
McKenzie et al., "The Role of Human Fc Receptor FcγRIIA in the Immune Clearance of Platelets: A Transgenic Mouse Model", *J. Immunology*, pp. 4311-4318.
Murali et al., *Immunologic Research*, 17(1&2):163-169 (1998).
Padlan et al., *Receptor*, 2:129-144 (1992).
Padlan et al., *Biochemical Society Transactions*, 21:963-967 (1993).
Protein Data Bank Accession No. 1ALT (Summary).
Russell et al., *J. Mol. Biol.*, 244:332-350 (1994).
Tabata et al., Pharm. Res. (1993), 10(4), 487-96 (abstract).
Weng et al., *J. Mol. Biol.*, 282:217-225 (1998).
Williams et al., "The Immunoglobulin Superfamily—Domains for Cell Surface Recognition," pp. 381-405 (1988).

* cited by examiner

*Primary Examiner*—Lori A Clow
*Assistant Examiner*—Anna Skibinsky

(57) ABSTRACT

This invention relates to a method of inhibiting Fc receptor binding of immunoglobulin including the use of a Fc receptor modulating compound which binds to defined surfaces on a Fc receptor. The present invention also relates to a method for treating a variety of diseases using a Fc receptor modulating compound.

6 Claims, 33 Drawing Sheets

Figure 1:
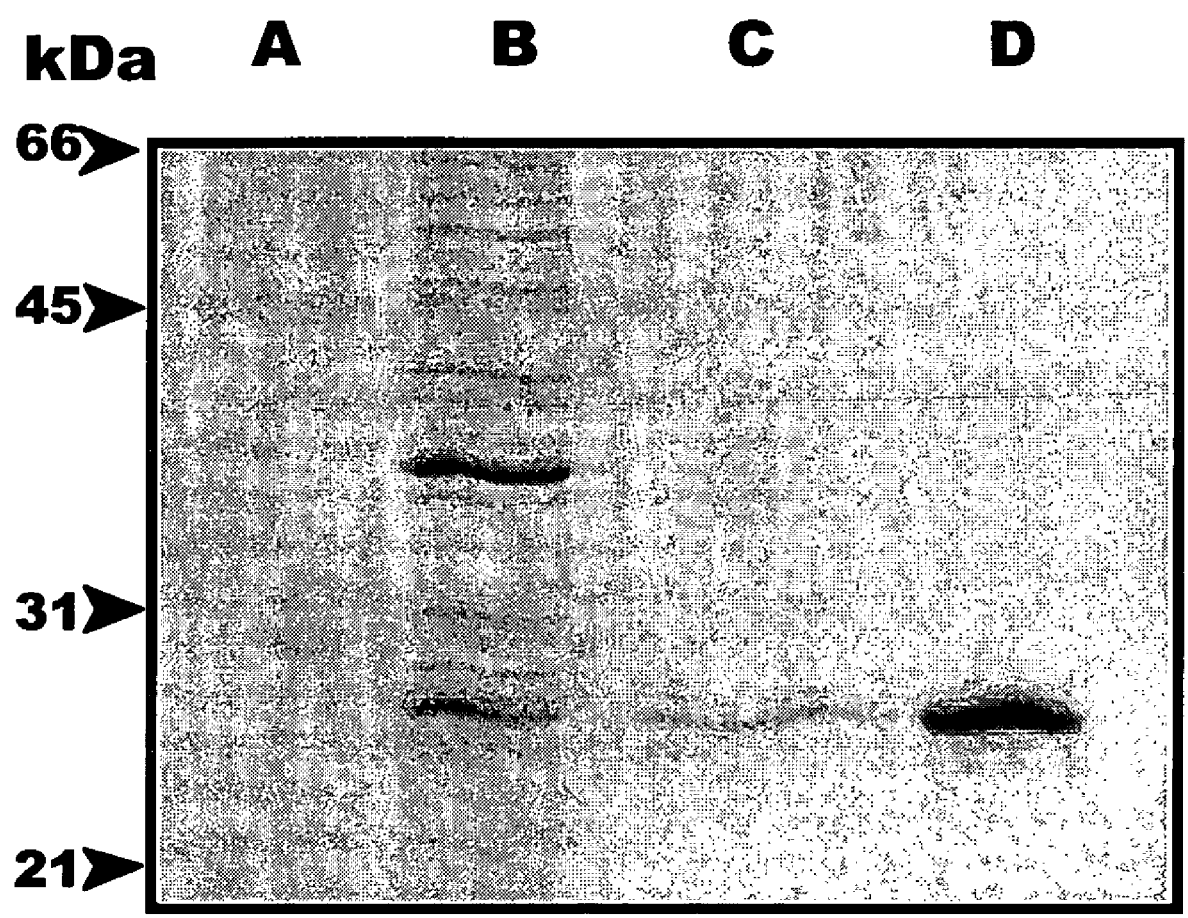

```
FcγRIIa   1 APPKAVLKLEPPWINVLQEDSVTLTCQGARSPESDSIQWFHNGNLIPTHT 50
                    A'              B              C
FcγRIIb   1 APPKAVLKLEPQWINVLQEDSVTLTCRGTHSPESDSIQWFHNGNLIPTHT 50
FcγRIIc   1 APPKAVLKLEPQWINVLQEDSVTLTCRGTHSPESDSIQWFHNGNLIPTHT 50

E              F              G          A         A'
FcγRIIa  51 QPSYRFKANNNDSGEYTCQTGQTSLSDPVHLTVLSEWLVLQTPHLEFQEG 100
FcγRIIb  51 QPSYRFKANNNDSGEYTCQTGQTSLSDPVHLTVLSEWLVLQTPHLEFQEG 100
FcγRIIc  51 QPSYRFKANNNDSGEYTCQTGQTSLSDPVHLTVLSEWLVLQTPHLEFQEG 100

B              C          C'             E              F
FcγRIIa 101 ETIMLRCHSWKDKPLVKVTFFQNGKSQKFSHLDPIFSIPQANHSHSGDYH 150
FcγRIIb 101 ETIVLRCHSWKDKPLVKVTFFQNGKSKKFSRSIPNFSIPQANHSHSGDYH 150
FcγRIIc 101 ETIVLRCHSWKDKPLVKVTFFQNGKSKKFSRSDPNFSIPQANHSHSGDYH 150

F          G        G
FcγRIIa 151 CTGNIGYTLFSSKPVTITVQ 170   1-170 of (SEQ ID NO:3)
FcγRIIb 151 CTGNIGYTLYSSKPVTITVQ 170   (SEQ ID NO:5)
FcγRIIc 151 CTGNIGYTLYSSKPVTITVQ 170   (SEQ ID NO:6)
```

FIG. 5

```
                                                                                           C'
                                              A              A'              B              C           ─────
                                          ─────         ─────────         ─────         ─────
Fc γRIIa   1 A P P K A V L K L E P P W I N V L Q E D S V T L T C Q G A R S P E S D S I Q W F H N G N L I P T H T   50
Fc γRI     1 T T K A V I T L Q P P W V S V F Q E E T V T L H C E V L H L P G S S T Q W F V N G T A T Q T S T P     50
Fc γRIII   1 D L P K A V V F L E P Q W Y S V L E K D S V T L K C Q G A Y S P E D N S T Q W F H N E S L I S S Q A   50
Fc εRI     1 V P Q K P K V S L N P P W N R I F K G E N V T L T C N G N N F F E V S S T K W F H N G S L S E E T N   50

E                                                                              A'
                  ─────                                                                          ─────
                            A                              B                     C                             F
                      ─────────                  ───────────────         ─────────                       ─────
Fc γRIIa  51 Q P S Y R F K A N N N D S G E Y T C Q T G Q T S L S D P V H L T V L S E W L V L Q T P H L E F Q E G 100
Fc γRI    51 S Y R I T S A S V N D S G E Y R C Q R G L S G R S D P I Q L E I H R G W L L L Q V S S R V F T E G E 100
Fc γRIII  51 S S Y F I D A A T V N D S G E Y R C Q T N L S T L S D P V Q L E V H I G W L L L Q A P R W V F K E E 100
Fc εRI    51 S S L N I V N A K F E D S G E Y K C Q H Q Q V N E S E P V Y L E V F S D W L L L Q A S A E V V M E G 100

G                                C'
                  ─────                            ─────
                            B                              C                           F
                      ─────────                ─────────────                   ─────────
Fc γRIIa 101 E T I M L R C H S W K D K P L V K V T F F Q N G K S Q K F S H L D P T F S I P Q A N H S H S G D Y H 150
Fc γRI   101 P L A L R C H A W K D K L V Y N V L Y Y R N G K A F K F F H W N S N L T I L K T N I S H N G T Y H C 199
Fc γRIII 101 D P I H L R C H S W K N T A L H K V T Y L Q N G K D R K Y F H H N S D F H I P K A T L K D S G S Y F 150
Fc εRI   101 Q P L F L R C H G W R N W D V Y K V I Y Y K D G E A L K Y W Y E N H N I S I T N A T V E D S G T Y Y 150

G'
             ─────
              F (cont)
             ─────────
Fc γRIIa 151 C T G N I G Y T L F S S K P V T I T V Q                                                               170
Fc γRI   151 S G – M G K H R Y T S A G I S V T V K E L F P A P V L N A S V T S P L L E G N L V T L S C E T K L L 199
Fc γRIII 151 C R G L V G S K N V S S E T V N I T I T                                                               170
Fc εRI   151 C T G K V W Q L D Y E S E P L N I T V I                                                               170

Fc γRI   200 L Q R P G L Q L Y F S F Y M G S K T L R G R N T S S E Y Q I L T A R R E D S G L Y W C E A A T E D G 249
Fc γRI   250 N V L K R S P E L E L 260                          1-259 of (SEQ ID NO:7)
```

FIG. 11

Sequence FcgRIIa    1-171
APPKAVLKLEPPWINVLQEDSVTLTCQGARSPESDSIQWFHNGNLIPTHTQPSYRFKANNNDSGE
YTCQTGQTSLSDPVHLTVLSEWLVLQTPHLEFQEGETIMLRCHSWKDKPLVKVTFFQNGKSQKFS
RLDPTFSIPQANHSHSGDYHCTGNIGYTLFSSKPVTITVQV                (SEQ ID NO:3)

Sequence FceRI      1-172
VPQKPKVSLNPPWNRIFKGENVTLTCNGNNFFEVSSTKWFHNGSLSEETNSSLNIVNAKFEDSGE
YKCQHQQVNESEPVYLEVFSDWLLLQASAEVVMEGQPLFLRCHGWRNWDVYKVIYYKDGEALKYW
YENHNISITNATVEDSGTYYCTGKVWQLDYESEPLNITVIKA              (SEQ ID NO:9)

FIG. 13

```
fcgr2a    ---APPKAVL KLEPPWINVL QEDSVTLTCQ GARSPESDSI QWFHNGNLIP
fcgr3b    RTEDLPKAVV FLEPQWYSVL EKDSVTLKCQ GAYSPEDNST QWFHNESLIS fcgr2a    THTQPSYRFK -ANNNDSGEY TCQTGQTSLS DPVHLTVLFE WLVLQTPHLE
fcgr3b    SQ-ASSYFID AATVNDSGEY RCQTNLSTLS DPVQLEVHIG WLLLQAPRWV fcgr2a    FQEGETIMLR CHSWKDKPLV KVTFFQNGKS QKFSHLDPTF SIPQANHSHS
fcgr3b    FKEEDPIHLR CHSWKNTALH KVTYLQNGKD RKYFHHNSDF HIPKATLKDS fcgr2a    GDYHCTGNIG YTLFSSKPVT ITV-QV   (SEQ ID NO:3)
fcgr3b    GSYFCRGLVG SKNVSSETVN ITITQ-   (SEQ ID NO:8)
```

FIG. 18

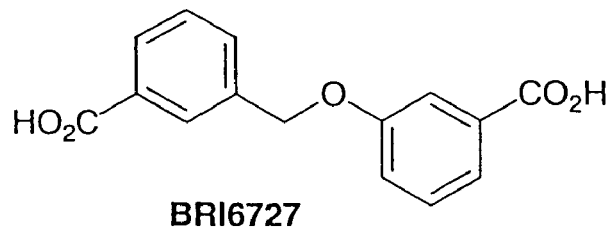
BRI6727
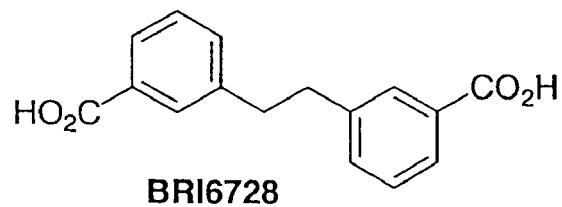
BRI6728
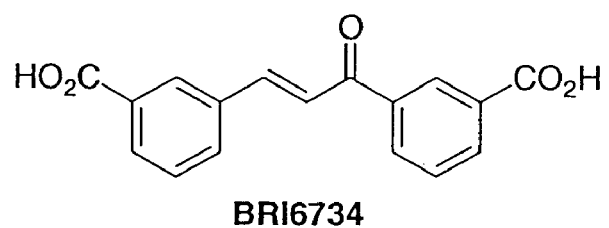
BRI6734
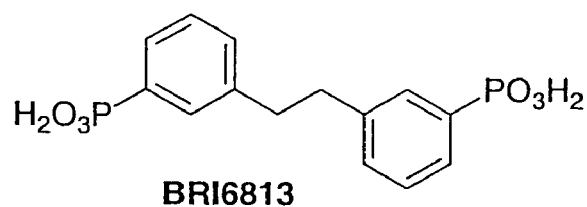
BRI6813
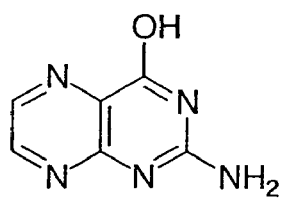
BRI6795
FIG. 23A

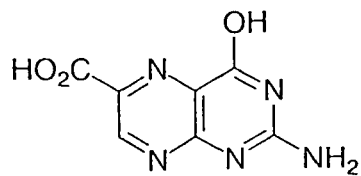
BRI6796
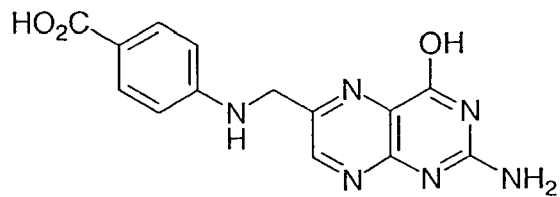
BRI6797
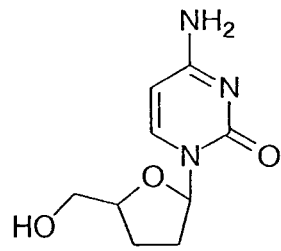
BRI6798
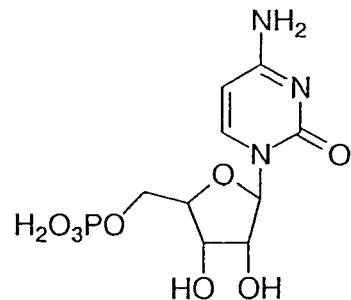
BRI6799
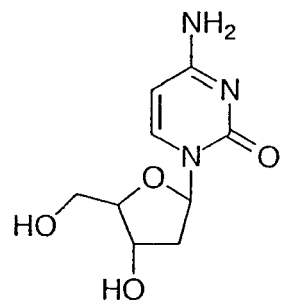
BRI6800
FIG. 23B

Activation of platelets in the presence of agonist only.
Platelets (100 ×10⁶/ml) were mixed in the presence of FcγRIIa agonist (HAGG, 200μg/ml) and PBS and the rate of platelet aggregation was measured as the gradient of the change to percent light transmission (x) over time (y).

Activation of platelets in the presence of agonist and BRI compound 6855.
Platelets (100 x10⁶/ml) were mixed in the presence of FcγRIIa agonist (HAGG, 200μg/ml) and compound BRI 6855 (5mg/ml) and the rate of platelet aggregation was measured as the gradient of the change to percent light transmission (x) over time (y).

FC RECEPTOR MODULATORS AND USES THEREOF

CROSS-REFERENCE TO RELATED APPLICATIONS

This application is a continuation-in-part of U.S. application Ser. No. 09/995,277 filed Nov. 26, 2001 now U.S. Pat. No. 6,835,753, which is a continuation application of application Ser. No. 09/393,598 filed Sep. 10, 1999, which claims priority from U.S. Provisional Patent Application No. 60/099,855 filed Sep. 11, 1998, U.S. Provisional Application No. 60/131,938, filed Apr. 30, 1999 and U.S. Provisional Application No. 60/148,479, filed Aug. 11, 1999. This application is also a continuation-in-part of U.S. application Ser. No. 10/687,109 filed Oct. 15, 2003 now abandoned, which is a continuation of U.S. application Ser. No. 09/245,764, filed Feb. 5, 1999 now U.S. Pat. No. 6,675,105, which claims priority from U.S. Provisional Patent Application No. 60/073,972, filed Feb. 6, 1998 and U.S. Provisional Patent Application No. 60/099,994, filed Sep. 11, 1998. All of the aforementioned patent applications are incorporated herein by reference in their entirety.

FIELD OF THE INVENTION

The present invention also relates to methods for inhibiting Fc receptor binding of an immunoglobulin in patients, compounds which modulate binding of an immunoglobulin to an Fc receptor and uses thereof.

BACKGROUND OF THE INVENTION

Fc receptors (FcR) are a family of highly related receptors that are specific for the Fc portion of immunoglobulin (Ig). These receptors have major roles in normal immunity and resistance to infection and provide the humoral immune system with a cellular effector arm. Receptors have been defined for each of the immunoglobulin classes and as such are defined by the class of Ig of which they bind (i.e. Fc gamma receptor (FcγR) bind gamma immunoglobulin (IgG), Fc epsilon receptor (FcεR) bind epsilon immunoglobulin (IgE), Fc alpha receptor (FcαR) bind alpha immunoglobulin (IgA)). Among the FcγR receptors, three subfamily members have been defined; FcγRI, which is a high affinity receptor for IgG; FcγRII, which are low affinity receptors for IgG that avidly bind to aggregates of immune complexes; and FcγRIII, which are low affinity receptors that bind to immune complexes. These receptors are highly related structurally but perform different functions. The structure and function of FcγRII is of interest because of its interaction with immune complexes and its association with disease.

FcγR are expressed on most hematopoietic cells, and through the binding of IgG play a key role in homeostasis of the immune system and host protection against infection. FcγRII is a low affinity receptor for IgG that essentially binds only to IgG immune complexes and is expressed on a variety of cell types including, for example monocytes, macrophages, neutrophils, eosinophils, platelets and B lymphocytes. FcγRII is involved in various immune and inflammatory responses including antibody-dependent cell-mediated cytotoxicity, clearance of immune complexes, release of inflammatory mediators and regulation of antibody production. The binding of IgG to a FcγR can lead to disease indications that involve regulation by FcγR. For example, the autoimmune disease thrombocytopenia purpura involves tissue (platelet) damage resulting from FcγR-dependent IgG immune complex activation of platelets or their destruction by FcγR+ phagocytes. In addition, various inflammatory diseases are known to involve IgG immune complexes (e.g. rheumatoid arthritis, systemic lupus erythematosus), including type II and type III hypersensitivity reactions. Type II and type III hypersensitivity reactions are mediated by IgG, which can activate either complement-mediated or phagocytic effector mechanisms, leading to tissue damage.

The elucidation of the protein structure of FcγRIIa, FcεRI, or indeed any FcR is of importance in the formulation of therapeutic and diagnostic reagents for disease management. Until the discovery of the present invention, the structure and resulting mechanism by which FcγRIIa regulates immune responses was unknown. Thus, despite the general multifunctional role of FcγRIIa, development of useful reagents for treatment or diagnosis of disease was hindered by lack of structural information of the receptor. The linear nucleic acid and amino acid sequence of FcγRIIa have been previously reported (Hibbs et al. *Proc. Natl. Acad. Sci. USA*, vol. 85, pp. 2240-2244, 1988). Mutagenesis studies to identify regions of human FcγRIIa (Hulett et al., *Eur. J. Immunol.*, vol. 23, pp. 40-645, 1993; Hulett et al., *J. Biol. Chem.*, vol. 69, pp. 15287-15293 1994; and Hulett et al., *J. Biol. Chem.*, vol. 270, pp. 21188-21194, 1995), human FcγRIIIb (Hibbs et al., *J. Immunol.*, vol. 152, p. 4466, 1994; and Tamm et al., *J. Biol. Chem.*, vol. 271, p. 3659, 1996) and mouse FcγRI (Hulett et al., *J. Immunol.*, vol. 148, pp. 1863-1868, 1991) have defined important regions of IgG binding to the FcγR. Information based on linear sequences, however, cannot accurately predict three dimensional structure of the protein and its functional domains. Huber et al. (*J. Mol. Biol.*, vol. 230, pp. 1077-1083, 1993) have described crystal formation of neonatal rat Fc receptor protein (FcRn). Burmeister et al. (*Nature*, vol. 372, pp. 336-343, 1994; and *Nature*, vol. 372, pp. 379-383, 1994) have described the structure of FcRn crystals. FcRn, however, is closely related to major histocompatability protein complex and not related to the leukocyte FcγR family by function or structure. Thus, the protein structure of FcRn is not predictive of the FcR structure of the present invention.

FcεR are expressed on mast cells, and through the binding of IgE, trigger an inflammatory immune response which is primarily due to the release of inflammatory mediators upon degranulation of the mast cell (e.g., histamine and serotonin). Release of these mediators causes localized vascular permeability and increase in fluids in the local tissues, including an influx of polymorphonuclear cells into the site. Thus, binding of IgE to an FcεRI can lead to disease indications that involve discharge of fluids from the gut and increased mucus secretion and bronchial contraction, such indications typically being associated with diseases involving allergic inflammation.

Therefore, the elucidation of protein structure of FcεRI is of importance in the formulation of therapeutic and diagnostic reagents for disease management, and in particular, for the management of diseases related to allergic inflammation and other Th2-based immune responses. As for the FcγR described above, the linear nucleic acid and amino acid sequences of human FcεRI have been previously reported (Kochan et al., 1998, *Nuc. Acid. Res.* 16:3584). Until the discovery of the present invention, however, the structure and resulting mechanism by which FcεR regulates immune responses was unknown. Thus, despite the knowledge of the general action of FcεRI, the development of useful reagents for treatment or diagnosis of disease, such as diseases associated with allergic inflammation, was hindered by lack of structural information of the receptor.

Because FcR are involved in a variety of biological mechanisms, there is a need for compounds which affect the binding of immunoglobulins to FcR. There is also a need for using such compounds to treat a variety of illnesses.

SUMMARY OF THE INVENTION

The discovery, by the present applicants, of the three-dimensional structure of Fc receptor (FcR) proteins, has permitted the generation of models of such three-dimensional structures, the development of methods of structure based drug design using such structures, and the identification of compounds identified by such methods and the use of such compounds in therapeutic compositions. The generated models have permitted the identification of target sites for interaction of compounds which modulate binding of an immunoglobulin to an Fc receptor.

Figure 30:
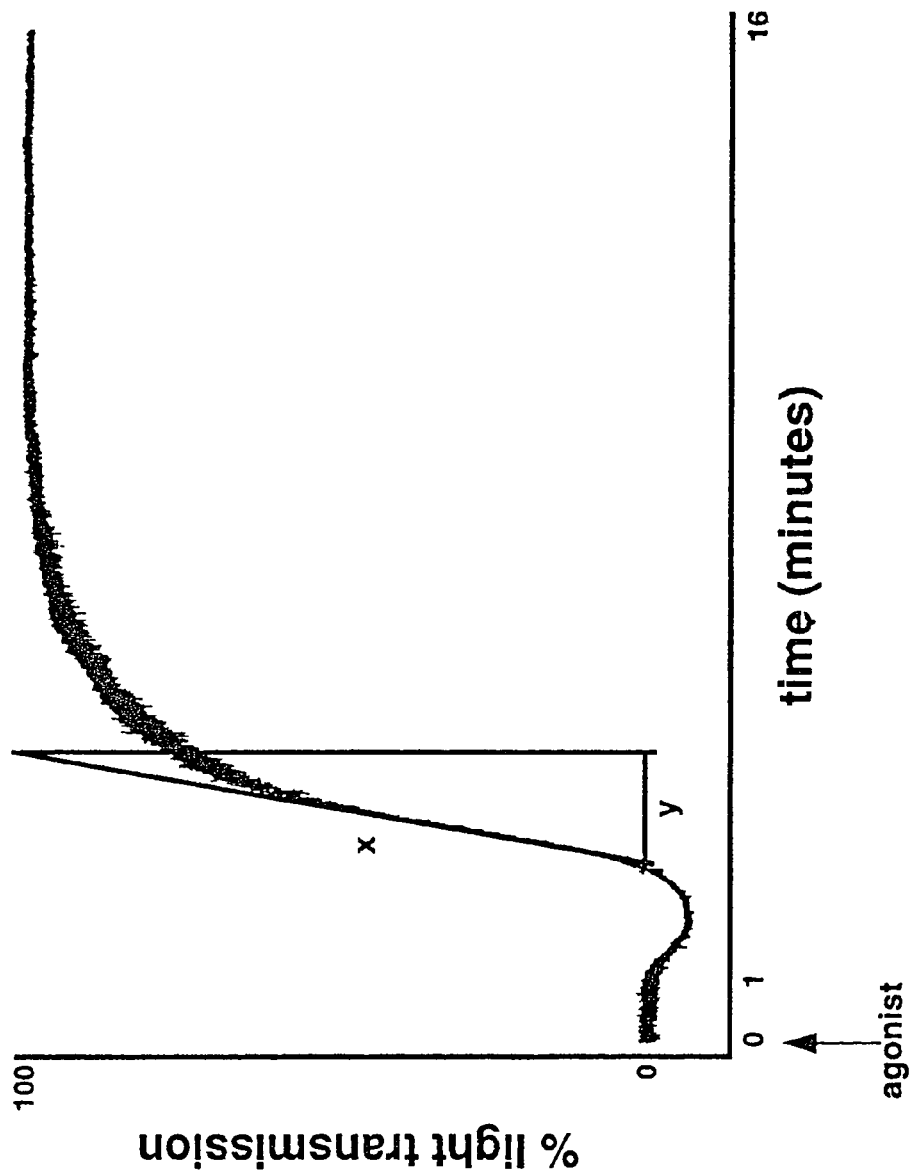
Figure 31:
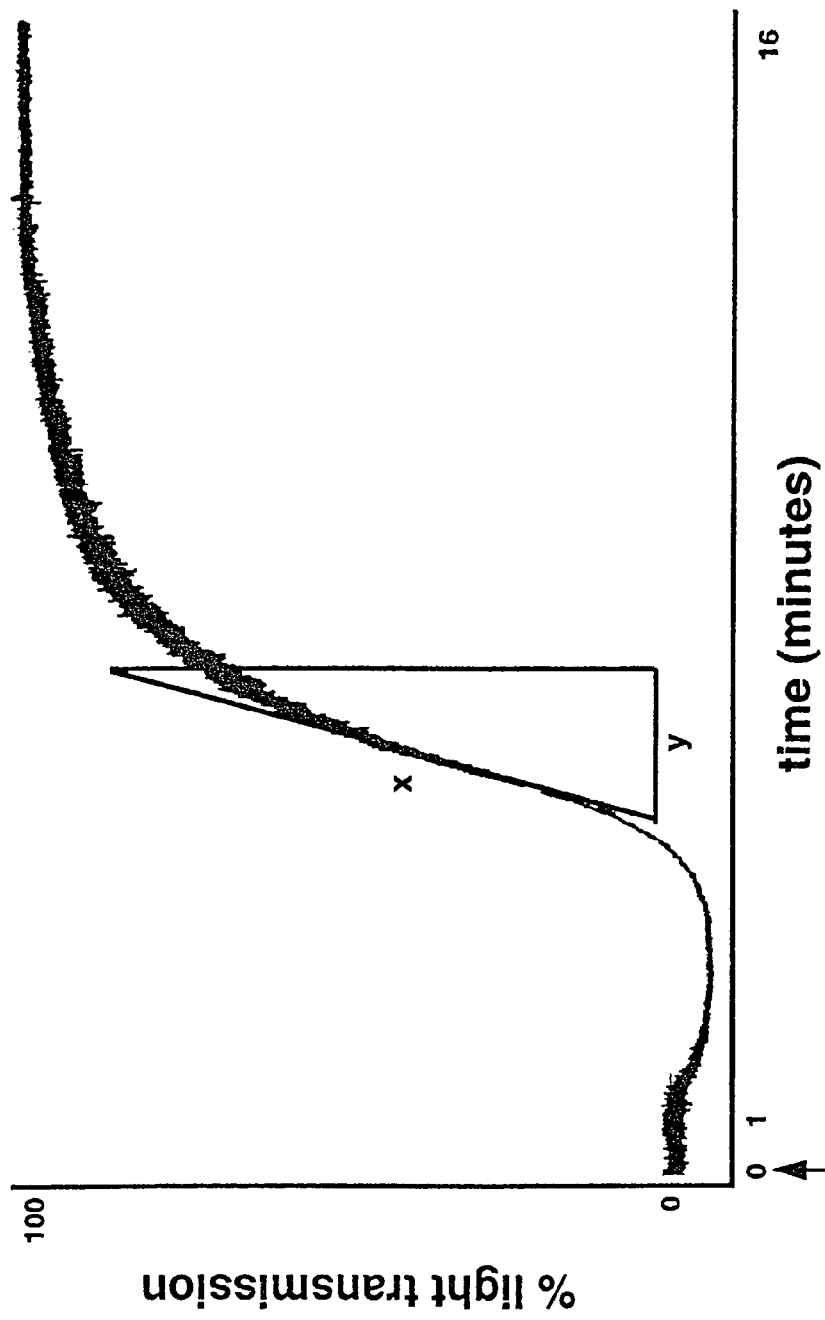
Figure 32:
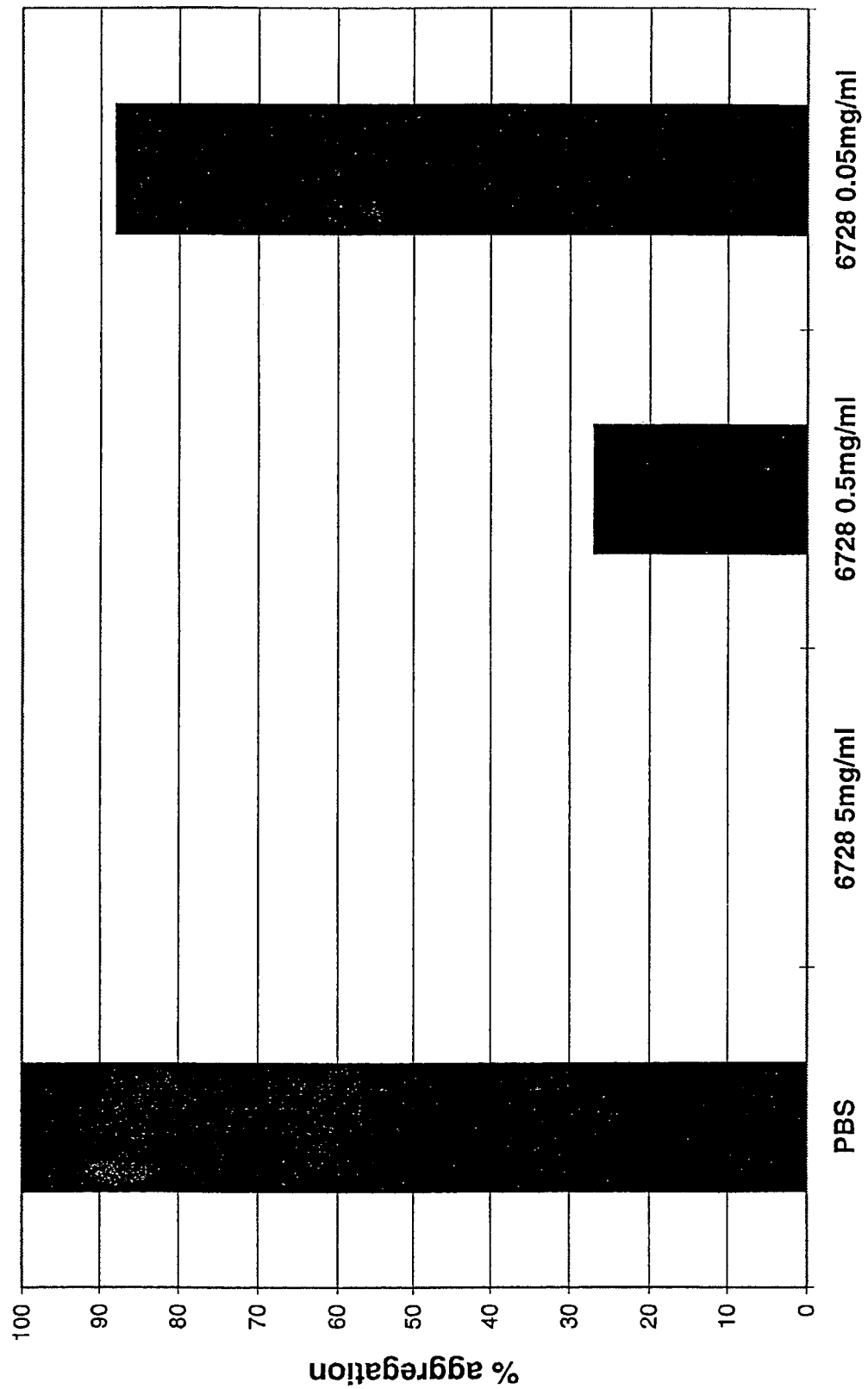

The present invention therefore provides a method of inhibiting Fc receptor binding of immunoglobulin in a patient, said Fc receptor being a dimer of two FcR monomers each comprising domains 1 (D1) and 2 (D2), the method comprising administering to said patient a pharmaceutically effective amount of a compound which binds to a surface on said Fc receptor selected from:

(a) the immunoglobulin-binding site, (b) the upper groove between said FcR monomers, (c) the dimerisation interface between said FcR monomers, (d) the interface, cleft or hinge region between D1 and D2 of said FcR monomers, and (e) the lower groove between said FcR monomers;

whereby said binding of said compound to said surface inhibits binding of said Fc receptor to immunoglobulin.

The Fc receptor is preferably selected from the group consisting of FcαR, FcεR, FcγR and mixtures thereof. More preferably, the Fc receptor is selected from the group consisting of FcγRIIa, FcγRIIb, FcγRIIc and mixtures thereof. Most preferably, the Fc receptor is FcγRIIa.

In a preferred embodiment of the invention there is provided a method of inhibiting Fc receptor binding of immunoglobulin in a patient, said Fc receptor being a dimer of two FcR monomers each comprising domains 1 (D1) and 2 (D2), the method comprising administering to said patient a pharmaceutically effective amount of a compound, wherein said compound binds to a surface on an immunoglobulin-binding site of a FcγRIIa receptor, wherein said surface comprises:

(a) a structure defined by the conformation of amino acid residues 155, 156, 158-160, 113-116, 129, 131, 133 and 134 of SEQ ID NO:3, (b) a structure defined by the conformation of amino acid residues 117-121, 125-129, 150-154 and 157-161 of SEQ ID NO:3 (preferably comprising an FG loop), (c) a structure defined by the conformation of amino acid residues 117-131 and 150-164 of SEQ ID NO:3, (d) a structure defined by the conformation of amino acid residues 17 to 20 of SEQ ID NO:3, or (e) a structure defined by the conformation of amino acid residues 12 to 14, 6 to 10, 77 to 80, 93 to 96 and 101 of SEQ ID NO:3.

The method of the present invention preferably reduces IgG-mediated tissue damage in said patient. The method also preferably reduces inflammation in said patient. More preferably, the method is used to treat an autoimmune disease.

BRIEF DESCRIPTION OF THE DRAWINGS

FIG. 1 is a scanned image of SDS-PAGE analysis of PsFcγRIIa protein during the purification process.

FIG. 2 is a scanned image of two-dimensional NEPHGE analysis of purified PsFcγRIIa protein.

FIG. 3 illustrates Langmuir plots of purified PsFcγRIIa protein binding to different isotypes of human immunoglobulin G.

FIG. 4 illustrates a graphical representation of the dimer of PFcγRIIa.

FIG. 5 illustrates the positions of the beta sheets in FcγRIIa Domains 1 and 2 and compares amino acid sequences of isomorphs of FcγRII.

FIG. 6 illustrates the stereo view of the FcγRIIa structure shown in FIG. 18.

FIG. 7 illustrates the location of amino acids involved in binding of Fc.RIIa to IgG.

FIG. 8 illustrates an expanded view of an IgG binding region showing position and side chains of the involved amino acids.

FIG. 9 illustrates an expanded view of an IgG binding region showing amino acids which when mutated to alanine improves IgG binding to FcγRIIa.

FIG. 10 illustrates an expanded view of the region of one FcγRIIa monomer that contributes to the dimer interface.

FIG. 11 illustrates a comparison of the amino acid sequence of FcγRIIa protein with the amino acid sequences of FcγRI, FcγRIIIb and FcεRI protein.

FIG. 12 illustrates a comparison of structural features shared by FcγRIIa, FcγRI, FcγRIIIb and FcεRI proteins.

FIG. 13 illustrates a sequence alignment of the amino acid sequences of FcγRIIa and FcεRI.

FIG. 14 is a scanned image illustrating a worm representation of the structure of an FcεRI monomer.

FIG. 15 is a scanned image illustrating a worm representation of the structure of an FcεRI dimer.

FIG. 16 is a scanned image illustrating a molecular surface representation of an FcεRI dimer model.

FIG. 17 is a schematic representation of target sites in the FcR structure for drug design.

FIG. 18 illustrates a sequence alignment of the amino acid sequences of FcγRIIa and FcγRIIIb.

FIG. 19 is a schematic illustration of a binding site on FcγRIIa receptor;

FIG. 20 shows a lateral schematic view of the groove, illustrating only one face, with the protein residues of interest;

FIG. 21 illustrates how a particular ligand relates to the general design of a compound of the present invention;

FIG. 22 is an illustration showing a various hydrogen bonding between the amino acids in FcγIIa receptor binding site and a particular modulator;

FIGS. 23A and 23B show some of the Fc receptor modulating compounds including those corresponding to Fc receptor modulating activities shown in FIGS. 24-27;

FIG. 24 shows modulating activity of FcγRIIa binding to human IgG1 by some of the compounds in FIGS. 23A and 23B;

FIG. 25 shows modulating activity of FcγRIIa binding to human IgG3 by some of the compounds in FIGS. 23A and 23B;

FIG. 26 shows modulating activity of FcγRIIa binding to human IgG1 by some of the compounds in FIGS. 23A and 23B;

FIG. 27 shows modulating activity of FcγRIIa binding to human IgG3 by some of the compounds in FIGS. 23A and 23B;

FIG. 28 shows enhanced sFcγRII binding of IgG1 and IgG3 in the presence of a hexapeptide;

FIG. 29 shows inhibition of sFcγRII binding to IgG1 and IgG3 in the presence of a tripeptide;

FIG. 30 is a plot of increased light transmission over time in the presence of agonist only;

FIG. 31 is a plot of increased light transmission over time in the presence of agonist and BRI6855 compound; and FIG. 32 is a plot of % platelet aggregation at a various concentrations of BRI6728 compound.

DETAILED DESCRIPTION OF THE INVENTION

A model of an Fc receptor is described herein, in which the model represents a three dimensional structure of an Fc receptor (FcR) protein. One embodiment of this model includes the three dimensional structure of an FcR protein, including those substantially conforming with the atomic coordinates represented in any one of Tables 1-5. The use of the term "substantially conforms" herein refers to at least a portion of a three dimensional structure of an FcR protein which is sufficiently spatially similar to at least a portion of a specified three dimensional configuration of a particular set of atomic coordinates (e.g., those represented by Table 1) to allow the three dimensional structure of the FcR protein to be modeled or calculated (i.e., by molecular replacement) using the particular set of atomic coordinates as a basis for determining the atomic coordinates defining the three dimensional configuration of the FcR protein. A three dimensional structure of a dimer of a first FcR can substantially conform to the atomic coordinates which represent a three dimensional structure of a monomer of a second FcR, and vice versa. In the first instance, at least a portion of the structure of the first FcR protein (i.e., a monomer of the first FcR protein dimer) substantially conforms to the atomic coordinates which represent the three dimensional configuration of the second FcR monomer. In the second reversed case, a first monomeric FcR protein substantially conforms to at least a portion of the second FcR protein (i.e., a monomer of the second FcR protein dimer). Similarly, a three dimensional structure of a given portion or chain of a first FcR can substantially conform to at least a portion of the atomic coordinates which represent a three dimensional configuration of a second FcR.

More particularly, a structure that substantially conforms to a given set of atomic coordinates is a structure wherein at least about 50% of such structure has an average root-mean-square deviation (RMSD) of less than about 1.5 Å for the backbone atoms in secondary structure elements in each domain, and more preferably, less than about 1.3 Å for the backbone atoms in secondary structure elements in each domain, and, in increasing preference, less than about 1.0 Å, less than about 0.7 Å, less than about 0.5 Å, and most preferably, less than about 0.3 Å for the backbone atoms in secondary structure elements in each domain. In a more preferred embodiment, a structure that substantially conforms to a given set of atomic coordinates is a structure wherein at least about 75% of such structure has the recited average root-mean-square deviation (RMSD) value, and more preferably, at least about 90% of such structure has the recited average root-mean-square deviation (RMSD) value, and most preferably, about 100% of such structure has the recited average root-mean-square deviation (RMSD) value. In an even more preferred embodiment, the above definition of "substantially conforms" can be extended to include atoms of amino acid side chains. As used herein, the phrase "common amino acid side chains" refers to amino acid side chains that are common to both the structure which substantially conforms to a given set of atomic coordinates and the structure that is actually represented by such atomic coordinates. Preferably, a three dimensional structure that substantially conforms to a given set of atomic coordinates is a structure wherein at least about 50% of the common amino acid side chains have an average root-mean-square deviation (RMSD) of less than about 1.5 Å, and more preferably, less than about 1.3 Å, and, in increasing preference, less than about 1.0 Å, less than about 0.7 Å, less than about 0.5 Å, and most preferably, less than about 0.3 Å. In a more preferred embodiment, a structure that substantially conforms to a given set of atomic coordinates is a structure wherein at least about 75% of the common amino acid side chains have the recited average root-mean-square deviation (RMSD) value, and more preferably, at least about 90% of the common amino acid side chains have the recited average root-mean-square deviation (RMSD) value, and most preferably, about 100% of the common amino acid side chains have the recited average root-mean-square deviation (RMSD) value.

A three dimensional structure of an FcR protein which substantially conforms to a specified set of atomic coordinates can be modeled by a suitable modeling computer program such as MODELER (A. Sali and T. L. Blundell, *J. Mol. Biol.*, vol. 234:779-815, 1993 as implemented in the Insight II Homology software package (Insight II (97.0), MSI, San Diego)), using information, for example, derived from the following data: (1) the amino acid sequence of the FcR protein; (2) the amino acid sequence of the related portion(s) of the protein represented by the specified set of atomic coordinates having a three dimensional configuration; and, (3) the atomic coordinates of the specified three dimensional configuration. A three dimensional structure of an FcR protein which substantially conforms to a specified set of atomic coordinates can also be calculated by a method such as molecular replacement, which is described in detail below.

A suitable three dimensional structure of an FcR protein for use in modeling or calculating the three dimensional structure of another FcR protein comprises the set of atomic coordinates represented in Table 1. The set of three dimensional coordinates set forth in Table 1 is represented in standard Protein Data Bank format. Accordingly, an FcR protein selected from the group of FcγRI, FcγRIIa, FcγRIIb, FcγRIIc, FcγRIIIb, FcεRI and FcαRI have a three dimensional structure which substantially conforms to the set of atomic coordinates represented by Table 1. As used herein, a three dimensional structure can also be a most probable, or significant, fit with a set of atomic coordinates. A most probable or significant fit refers to the fit that a particular FcR protein has with a set of atomic coordinates derived from that particular FcR protein. Such atomic coordinates can be derived, for example, from the crystal structure of the protein such as the coordinates determined for the FcγRIIa structure provided herein, or from a model of the structure of the protein as determined herein for FcεRI and FcγRIIIb. For example, the three dimensional structure of a monomeric FcγRIIa protein, including a naturally occurring or recombinantly produced Fc.RIIa protein, substantially conforms to and is a most probable fit, or significant fit, with the atomic coordinates of Table 1. The three dimensional crystal structure of FcγRIIa that was determined by the present inventors comprises the atomic coordinates of Table 1. Also as an example, the three dimensional structure of an Fc RI protein substantially conforms to the atomic coordinates of Table 1 and both substantially conforms to and is a most probable fit with the atomic coordinates of Table 3, and the three dimensional structure of the model of FcεRI monomer determined by the present inventors comprises the atomic coordinates of Table 3. This definition can be applied to the other FcR proteins in a similar manner.

A preferred structure of an FcR protein substantially conforms to the atomic coordinates, and the B-values and/or the thermal parameters represented in Table 1. Such values as listed in Table 1 can be interpreted by one of skill in the art. A more preferred three dimensional structure of an FcR protein substantially conforms to the three dimensional coordinates represented in Table 1. An even more preferred three dimensional structure of an FcR protein is a most probable fit with the three dimensional coordinates represented in Table 1. Methods to determine a substantially conforming and probable fit are within the expertise of skill in the art and are described herein in the Examples section.

A preferred FcR protein that has a three dimensional structure which substantially conforms to the atomic coordinates represented by Table 1 includes an FcR protein having an amino acid sequence that is at least about 25%, preferably at least about 30%, more preferably at least about 40%, more preferably at least about 50%, more preferably at least about 60%, more preferably at least about 70%, more preferably at least about 80% and more preferably at least about 90%, identical to an amino acid sequence of an FcγRIIa protein, preferably an amino acid sequence including SEQ ID NO:3, SEQ ID NO:10, SEQ ID NO:11 and/or SEQ ID NO:12, across the full-length of the FcR sequence when using, for example, a sequence alignment program such as the DNAsis™ program (available from Hitachi Software, San Bruno, Calif.) or the MacVector™ program (available from the Eastman Kodak Company, New Haven, Conn.) or the GC.™ program (available from "GC.", University of Wisconsin, Madison, Wis.), such alignment being performed for example, using the standard default values accompanying such alignment programs.

One embodiment includes a three dimensional structure of FcγRIIa protein. A suitable three dimensional structure of FcγRIIa protein substantially conforms with the atomic coordinates represented in Table 1. A suitable three dimensional structure of FcγRIIa also substantially conforms with the atomic coordinates represented by Tables 2-5. A suitable three dimensional structure of FcγRIIa protein also comprises the set of atomic coordinates represented in Table 1. The set of three dimensional coordinates of FcγRIIa protein is represented in standard Protein Data Bank format. A preferred structure of FcγRIIa protein substantially conforms to the atomic coordinates, and the B-values and/or the thermal parameters represented in Table 1 (monomeric FcγRIIa) or Table 2 (dimeric FcγRIIa). Such values as listed in Table 1 can be interpreted by one of skill in the art. A more preferred three dimensional structure of FcγRIIa protein has a most probable fit with the three dimensional coordinates represented in Table 1.

Another embodiment includes a three dimensional structure of FcεRI protein. A suitable three dimensional structure of FcεRI protein substantially conforms with the atomic coordinates represented in Table 1, Table 2, Table 3, Table 4 or Table 5. A more suitable three dimensional structure of FcεRI protein substantially conforms with the sets of atomic coordinates represented in Table 3 (monomeric FcεRI) or Table 4 (dimeric FcεRI). A suitable three dimensional structure of Fc.RI protein also comprises the set of atomic coordinates represented in Tables 3 or 4. The sets of three dimensional coordinates of Fc.RI protein are represented in standard Protein Data Bank format. Such coordinates as listed in Tables 1-5 can be interpreted by one of skill in the art. A more preferred three dimensional structure of FcεRI protein has a probable fit with the three dimensional coordinates represented in Table 3 or Table 4.

A further embodiment includes a three dimensional structure of FcγRIIIb protein. A suitable three dimensional structure of FcγRIIIb protein substantially conforms with the atomic coordinates represented in Table 1, Table 2, Table 3, Table 4 or Table 5. An even more suitable three dimensional structure of FcγRIIIb protein substantially conforms with the set of atomic coordinates represented in Table 5. A suitable three dimensional structure of FcγRIIIb protein also comprises the set of atomic coordinates represented in Table 5. The sets of three dimensional coordinates of FcγRIIIb protein are represented in standard Protein Data Bank format. A more preferred three dimensional structure of FcγRIIIb protein has a most probable fit with the three dimensional coordinates represented in Table 5.

A three dimensional structure of any FcR protein can be modeled using methods generally known in the art based on information obtained from analysis of an FcγRIIa crystal, and from other FcR structures which are derived from an FcγRIIa crystal. The Examples section below discloses the production of an FcγRIIa crystal, the production of an FcεRI crystal, the three dimensional structure of an Fc.RIIa protein monomer and dimer derived from the FcγRIIa crystal, and the model of the three dimensional structure of an FcεRI protein monomer and dimer using methods generally known in the art based on the information obtained from analysis of an Fc.RIIa crystal. It is an embodiment that the three dimensional structure of a crystalline FcR, such as the crystalline FcγRIIa, can be used to derive the three dimensional structure of any other FcR, such as the FcεRI disclosed herein. Subsequently, the derived three dimensional structure of such an FcR (e.g., FcεRI) derived from the crystalline structure of FcγRIIa can be used to derive the three dimensional structure of other FcR, such as FcRγIII. Therefore, the novel discovery of the crystalline FcγRIIa and the three dimensional structure of FcγRIIa permits one of ordinary skill in the art to now derive the three dimensional structure, and models thereof, of any FcR. The derivation of the structure of any FcR can now be achieved even in the absence of having crystal structure data for such other FcR, and when the crystal structure of another FcR is available, the modeling of the three dimensional structure of the new FcR can be refined using the knowledge already gained from the Fc.RIIa structure. It is therefore an advantage that, in the absence of crystal structure data for other FcR proteins, the three dimensional structures of other FcR proteins can be modeled, taking into account differences in the amino acid sequence of the other FcR. Indeed, the report of the crystallization of the monomeric FcεRI and publication of a model of the receptor (Garman et al., Dec. 23, 1998, *Cell* 95:951-961) subsequent to the priority filing dates of the present application has confirmed that the monomeric FcεRI protein determined by the present inventors comprising the atomic coordinates represented in Table 3 has the overall gross structural features of the three dimensional structure of the crystalline FcεRI reported in Garman et al. Although the atomic coordinates of the crystalline FcεRI structure of Garman et al. are not currently publicly available, a review of the structural representations and discussion in Garman et al. indicates that the three dimensional structure of the crystalline FcεRI is expected to substantially conform to the atomic coordinates represented by Table 3. Moreover, the novel discoveries described herein allow for structure based drug design of compounds which affect the activity of virtually any FcR, and particularly, of FcγR and FcεRI.

Crystals are derivatized with heavy atom compounds such as complexes or salts of Pt, Hg, Au and Pb and X-ray diffraction data are measured for native and derivatized crystals. Differences in diffraction intensities for native crystals and derivatized crystals can be used to determine phases for these data by the methods of MIR (muliple Isomorphous Replacement) or SIRAS (single isomorphous replacement with anomolous scattering). The Fourier transform of these data yield a low resolution electron density map for the protein. This electron density can be modified by image enhancement techniques. A molecular model for the protein is then placed in the electron density. This initial (partial) structure can be refined using a computer program (such as XPLOR) by modifying the parameters which describe the structure to minimize the difference between the measured and calculated diffraction patterns, while simultaneously restraining the model to conform to known geometric and chemical properties of proteins. New phases and a thus a new electron density map can be calculated for protein. Using this map as a guide the molecular model of the structure may be improved manually. This procedure is repeated to give the structure of the protein, represented herein for FcγRIIa as a set of atomic coordinates in Table 1.

One embodiment includes a three dimensional structure of Fc.RIIa protein, in which the atomic coordinates of the FcγRIIa protein are generated by the method comprising: (a) providing FcγRIIa protein in crystalline form; (b) generating an electron-density map of the crystalline FcγRIIa protein; and (c) analyzing the electron-density map to produce the atomic coordinates.

A three dimensional structure of FcγRIIa protein of the present invention can be used to derive a model of the three dimensional structure of another FcR protein (i.e., a structure to be modeled). As used herein, a "structure" of a protein refers to the components and the manner of arrangement of the components to constitute the protein. As used herein, the term "model" refers to a representation in a tangible medium of the three dimensional structure of a protein, polypeptide or peptide. For example, a model can be a representation of the three dimensional structure in an electronic file, on a computer screen, on a piece of paper (i.e., on a two dimensional medium), and/or as a ball-and-stick figure. Physical three-dimensional models are tangible and include, but are not limited to, stick models and space-filling models. The phrase "imaging the model on a computer screen" refers to the ability to express (or represent) and manipulate the model on a computer screen using appropriate computer hardware and software technology known to those skilled in the art. Such technology is available from a variety of sources including, for example, Evans and Sutherland, Salt Lake City, Utah, and Biosym Technologies, San Diego, Calif. The phrase "providing a picture of the model" refers to the ability to generate a "hard copy" of the model. Hard copies include both motion and still pictures. Computer screen images and pictures of the model can be visualized in a number of formats including space-filling representations, a carbon traces, ribbon diagrams (see, for example, FIG. 14 which is a two dimensional ribbon diagram model of a three-dimensional structure of human Fc.RI protein) and electron density maps.

Suitable target FcR structures to model include any FcR protein, polypeptide or peptide, including monomers, dimers and multimers of an FcR protein, that is substantially structurally related to an FcγRIIa protein. A preferred target FcR structure that is substantially structurally related to an FcγRIIa protein includes a target FcR structure having an amino acid sequence that is at least about 25%, preferably at least about 30%, more preferably at least about 36%, more preferably at least about 40%, more preferably at least about 50%, more preferably at least about 60%, more preferably at least about 70%, more preferably at least about 80% and more preferably at least about 90%, identical to an amino acid sequence of an FcγRIIa protein, preferably an amino acid sequence including SEQ ID NO:3, SEQ ID NO:10, SEQ ID NO:11, SEQ ID NO:12, SEQ ID NO:14 and/or SEQ ID NO:15, across the full-length of the target FcR structure sequence when using, for example, a sequence alignment program such as the DNAsis™ program (available from Hitachi Software, San Bruno, Calif.) or the MacVector™ program (available from the Eastman Kodak Company, New Haven, Conn.) or the GC program (available from "GC.", University of Wisconsin, Madison, Wis.), such alignment being performed for example, using the standard default values accompanying such alignment programs. More preferred target FcR structures to model include proteins comprising amino acid sequences that are at least about 50%, preferably at least about 60%, more preferably at least about 70%, more preferably at least about 80%, more preferably at least about 90%, and more preferably at least about 95%, identical to amino acid sequence SEQ ID NO:3, SEQ ID NO:5, SEQ ID NO:6, SEQ ID NO:7, SEQ ID NO:8, SEQ ID NO:9, SEQ ID NO:10, SEQ ID NO:11, SEQ ID NO:12, or SEQ ID NO:13 when comparing preferred regions of the sequence, such as the amino acid sequence for Domain 1 or Domain 2 of any one of the amino acid sequences, when using a DNA alignment program disclosed herein to align the amino acid sequences. A more preferred target FcR structure to model includes a structure comprising Fc.RI, Fc.RIIa, Fc.RIIb, FcγRIIc, FcγRIIIb, FcεRI or FcεRI protein, more preferably a structure comprising the amino acid sequence SEQ ID NO:3, SEQ ID NO:5, SEQ ID NO:6, SEQ ID NO:7, SEQ ID NO:8, SEQ ID NO:9, SEQ ID NO:10, SEQ ID NO:11, SEQ ID NO:12, or SEQ ID NO:13 and more preferably a structure consisting of the amino acid sequence SEQ ID NO:3, SEQ ID NO:5, SEQ ID NO:6, SEQ ID NO:7, SEQ ID NO:8, SEQ ID NO:9, SEQ ID NO:10, SEQ ID NO:11, SEQ ID NO:12, or SEQ ID NO:13.

Preferred target FcR structures to model also include, but are not limited to, derivations of Fc receptor proteins, such as an Fc receptor having one or more amino acid residues substituted, deleted or added (referred to herein as Fc receptor mutants), or proteins encoded by natural allelic variants of a nucleic acid molecule encoding an Fc receptor. A preferred Fc receptor protein to model includes FcγRIIa.Tm (i.e., an FcγRIIa protein from which the transmembrane domain has been deleted), and mutants or natural allelic variants of a nucleic acid molecule encoding Fc.RI, FcγRIIa, FcγRIIb, FcγRIIc, FcγRIIIb, FcεRI, FcεRI protein. More preferred Fc receptor proteins to model include Fc receptor proteins having an amino acid sequence including SEQ ID NO:5, SEQ ID NO:6, SEQ ID NO:7, SEQ ID NO:8, SEQ ID NO:9, SEQ ID NO:10, SEQ ID NO:11, SEQ ID NO:12, or SEQ ID NO:13 or mutants or natural allelic variants of SEQ ID NO:3, SEQ ID NO:5, SEQ ID NO:6, SEQ ID NO:7, SEQ ID NO:8, SEQ ID NO:9, SEQ ID NO:10, SEQ ID NO:11, SEQ ID NO:12, or SEQ ID NO:13. An amino acid sequence for FcγRIIb is represented herein as SEQ ID NO:5, an amino acid sequence for FcγRIIc is represented herein as SEQ ID NO:6, an amino acid sequence for FcεRI is represented herein as SEQ ID NO:7, an amino acid sequence for FcγRIII is represented herein as SEQ ID NO:8, an amino acid sequence for FcεRI is represented herein as SEQ ID NO:9 and as set forth in FIG. 11, and an amino acid sequence for FcεRI is represented herein as SEQ ID NO:13. It is noted that the nucleotide and amino acid sequences for all of the above-known FcR are known and publicly available. Preferred allelic variants to model include, but are not limited to, FcγRIIa allelic variants having a glutamine at residue 27 of SEQ ID NO:3 and an arginine at residue 131 of SEQ ID NO:3, represented herein as SEQ ID NO:10; a tryptophan at residue 27 of SEQ ID NO:3 and a histidine at residue 131 of SEQ ID NO:3, represented herein as SEQ ID NO:11; or a tryptophan at residue 27 of SEQ ID NO:3 and an arginine at residue 131 of SEQ ID NO:3, represented herein as SEQ ID NO:12.

As used herein, a "natural allelic variant" refers to alternative forms of a gene that occupies corresponding loci on homologous chromosomes. Allelic variants typically encode proteins having similar activity to that of the protein encoded by the gene to which they are being compared. Allelic variants can also comprise alterations in the 5' or 3' untranslated regions of the gene (e.g., in regulatory control regions). Allelic variants are well known to those skilled in the art and would be expected to be found within a given group of genes encoding an Fc receptor in a given species of animal.

As used herein, "mutants of a nucleic acid molecule encoding an Fc receptor" refer to nucleic acid molecules modified by nucleotide insertions, deletions and/or substitutions. Preferably, a mutant of an Fc receptor nucleic acid molecule comprises modifications such that the protein encoded by the mutant of an Fc receptor nucleic acid molecule (i.e., an Fc receptor protein mutant) has one or more epitopes that can be targeted by a humoral or cellular immune response against a non-mutated Fc receptor protein. More preferably, the nucleic acid molecule encoding a mutant Fc receptor protein can form a stable hybrid with a nucleic acid sequence encoding a non-mutated Fc receptor nucleic acid molecule under stringent hybridization conditions. Even more preferably, the nucleic acid molecule encoding a mutant Fc receptor protein can form a stable hybrid, under stringent hybridization conditions, with a nucleic acid sequence encoding an amino acid sequence including SEQ ID NO:3, SEQ ID NO:5, SEQ ID NO:6, SEQ ID NO:7, SEQ ID NO:8, SEQ ID NO:9, SEQ ID NO:10, SEQ ID NO:11, SEQ ID NO:12, or SEQ ID NO:13.

As used herein, stringent hybridization conditions refer to standard hybridization conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., *ibid.*, is incorporated by reference herein in its entirety (see specifically, pages 9.31-9.62, 11.7 and 11.45-11.61). In addition, formulae to calculate the appropriate hybridization and wash conditions to achieve hybridization permitting varying degrees of mismatch of nucleotides are disclosed, for example, in Meinkoth et al., 1984, *Anal. Biochem.* 138, 267-284; Meinkoth et al., *ibid.*, is incorporated by reference herein in its entirety.

More particularly, stringent hybridization conditions, as referred to herein, refer to conditions which permit isolation of nucleic acid molecules having at least about 70% nucleic acid sequence identity with the nucleic acid molecule being used to probe in the hybridization reaction, more particularly at least about 75%, and most particularly at least about 80%. Such conditions will vary, depending on whether DNA:RNA or DNA:DNA hybrids are being formed. Calculated melting temperatures for DNA:DNA hybrids are 10 C less than for DNA:RNA hybrids. In particular embodiments, stringent hybridization conditions for DNA:DNA hybrids include hybridization at an ionic strength of 0.1×SSC (0.157 M Na$^+$) at a temperature of between about 20 C and about 35 C, more preferably, between about 28 C and about 40 C, and even more preferably, between about 35 C and about 45 C. In particular embodiments, stringent hybridization conditions for DNA:RNA hybrids include hybridization at an ionic strength of 0.1×SSC (0.157 M Na$^+$) at a temperature of between about 30 C and about 45 C, more preferably, between about 38 C and about 50 C, and even more preferably, between about 45 C and about 55 C. These values are based on calculations of a melting temperature for molecules larger than about 100 nucleotides, 0% formamide and a G+C content of about 50%. Alternatively, $T_m$ can be calculated empirically as set forth in Sambrook et al., supra, pages 11.55 to 11.57.

Figure 12:
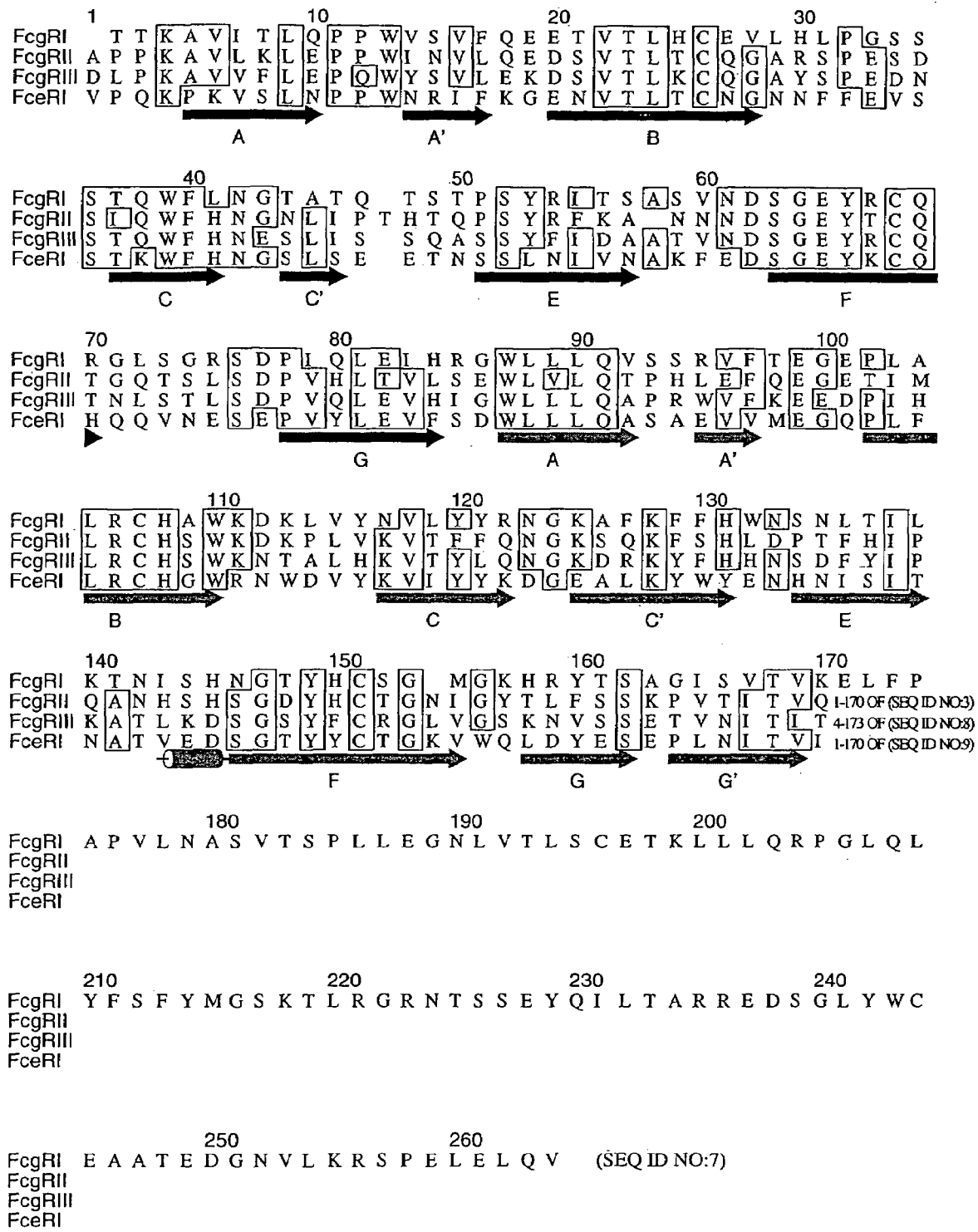

A model can be derived using conserved structural features between the known three dimensional structure of one FcR protein, such as FcγRIIa, and another target FcR structure. Such structural features include, but are not limited to, amino acid sequence, conserved di-sulphide bonds, and β-strands or β-sheets that are highly conserved in immunoglobulin superfamily members. For example, FIGS. 5, 11 and 12 illustrate the relationship of β-strands with the linear amino acid sequence of various Fc receptor proteins. Preferably, a model is derived by starting with the backbone of the three dimensional structure of FcγRIIa protein. Individual residues are then replaced according to the amino acid sequence of the target FcR structure at residues that differ from the amino acid sequence of an Fc.RIIa protein. Care is taken that replacement of residues does not disturb the tertiary structure of the backbone. While procedures to model target FcR structures are generally known in the art, provided here is a three dimensional structure of FcγRIIa protein and the first three dimensional structures of protein substantially related to a member of the family of FcγR receptors, an FcεRI and an FcγRIIIb. Thus, the present invention provides essential information to produce accurate, and therefore, useful models of a member of the family of Fc.R receptors, of the FcεRI receptor and of the FcεRI receptor. As discussed above, once the three dimensional structure of a second FcR has been derived from a determined three dimensional structure of a first FcR such as FcγRIIa disclosed herein, the second FcR three dimensional structure can be used to derive (i.e., model or calculate) the three dimensional structure of another FcR.

A structure can be modeled using techniques generally described by, for example, Sali, *Current Opinions in Biotechnology*, vol. 6, pp. 437-451, 1995, and algorithms can be implemented in program packages such as Homology 95.0 (in the program Insight II, available from Biosym/MSI, San Diego, Calif.). Use of Homology 95.0 requires an alignment of an amino acid sequence of a known structure having a known three dimensional structure with an amino acid sequence of a target structure to be modeled. The alignment can be a pairwise alignment or a multiple sequence alignment including other related sequences (for example, using the method generally described by Rost, *Meth. Enzymol.*, vol. 266, pp. 525-539, 1996) to improve accuracy. Structurally conserved regions can be identified by comparing related structural features, or by examining the degree of sequence homology between the known structure and the target structure. Certain coordinates for the target structure are assigned using known structures from the known structure. Coordinates for other regions of the target structure can be generated from fragments obtained from known structures such as those found in the Protein Data Bank maintained by Brookhaven National Laboratory, Upton, N.Y. Conformation of side chains of the target structure can be assigned with reference to what is sterically allowable and using a library of rotamers and their frequency of occurrence (as generally described in Ponder and Richards, *J. Mol. Biol.*, vol. 193, pp. 775-791, 1987). The resulting model of the target structure, can be refined by molecular mechanics (such as embodied in the program Discover, available from Biosym/MSI) to ensure that the model is chemically and conformationally reasonable.

Accordingly, one embodiment is a method to derive a model of the three dimensional structure of a target FcR structure, the method comprising the steps of: (a) providing an amino acid sequence of an FcγRIIa protein and an amino acid sequence of a target FcR structure; (b) identifying structurally conserved regions shared between the FcγRIIa amino acid sequence and the target FcR structure amino acid sequence; (c) determining atomic coordinates for the target FcR structure by assigning said structurally conserved regions of the target FcR structure to a three dimensional structure using a three dimensional structure of an FcγRIIa protein based on atomic coordinates that substantially conform to the atomic coordinates represented in Table 1, to derive a model of the three dimensional structure of the target structure amino acid sequence. A model according to the present invention has been previously described herein. Preferably the model comprises a computer model. The method can further comprise the step of electronically simulating the structural assignments to derive a computer model of the three dimensional structure of the target structure amino acid sequence. Suitable target structures to model include proteins, polypeptides and peptides of Fc receptors disclosed herein, including monomers and dimers of such receptors. Preferred amino acid sequences to model are disclosed herein.

Another embodiment is a method to derive a computer model of the three dimensional structure of a target FcR structure for which a crystal has been produced (referred to herein as a "crystallized target structure"). A suitable method to produce such a model includes the method comprising molecular replacement. Methods of molecular replacement are generally known by those of skill in the art (generally described in Brunger, *Meth. Enzym.*, vol. 276, pp. 558-580, 1997; Navaza and Saludjian, *Meth. Enzym.*, vol. 276, pp. 581-594, 1997; Tong and Rossmann, *Meth. Enzym.*, vol. 276, pp. 594-611, 1997; and Bentley, *Meth. Enzym.*, vol. 276, pp. 611-619, 1997, each of which are incorporated by this reference herein in their entirety) and are performed in a software program including, for example, XPLOR. X-ray diffraction data is collected from the crystal of a crystallized target structure. The X-ray diffraction data is transformed to calculate a Patterson function. The Patterson function of the crystallized target structure is compared with a Patterson function calculated from a known structure (referred to herein as a search structure). The Patterson function of the crystallized target structure is rotated on the search structure Patterson function to determine the correct orientation of the crystallized target structure in the crystal. The translation function is then calculated to determine the location of the target structure with respect to the crystal axes. Once the crystallized target structure has been correctly positioned in the unit cell, initial phases for the experimental data can be calculated. These phases are necessary for calculation of an electron density map from which structural differences can be observed and for refinement of the structure. Preferably, the structural features (e.g., amino acid sequence, conserved di-sulphide bonds, and .-strands or .-sheets) of the search molecule are related to the crystallized target structure. Preferably, a crystallized target FcR structure useful in a method of molecular replacement has an amino acid sequence that is at least about 25%, more preferably at least about 30%, more preferably at least about 40%, more preferably at least about 50%, more preferably at least about 60%, more preferably at least about 70%, more preferably at least about 80% and more preferably at least about 90% identical to the amino acid sequence of the search structure (e.g., FcγRIIa), when the two amino acid sequences are compared using a DNA alignment program disclosed herein. A preferred search structure includes an FcγRIIa protein comprising an amino acid sequence including SEQ ID NO:3, SEQ ID NO:10, SEQ ID NO:11, SEQ ID NO:12, SEQ ID NO:14 or SEQ ID NO:15. A more preferred search structure of the present invention includes an FcγRIIa protein having a three dimensional structure that substantially conforms with the atomic coordinates listed in Table 1. Preferably, a Patterson function of a crystalline FcγRIIa protein is derived from X-ray diffraction of an FcγRIIa crystal. A preferred target FcR structure for use in a molecular replacement strategy includes FcεRI, FcγRIIb, FcγRIIc, FcγRIII, FcεRI and/or FcγRI, and most preferably, FcγRI and FcγRIIIb.

A preferred embodiment includes a method to derive a three dimensional structure of a crystallized target FcR structure (i.e. a crystallized FcR protein), said method comprising the steps of: (a) comparing the Patterson function of a crystallized target FcR structure with the Patterson function of crystalline FcγRIIa protein to produce an electron-density map of said crystallized target FcR structure; and (b) analyzing the electron-density map to produce the three dimensional structure of the crystallized target FcR structure.

Another embodiment is a method to determine a three dimensional structure of a target structure, in which the three dimensional structure of the target FcR structure is not known. Such a method is useful for identifying structures that are related to the three dimensional structure of an Fc.RIIa protein based only on the three dimensional structure of the target structure. Thus, the present method enables identification of structures that do not have high amino acid identity with an FcγRIIa protein but which do share three dimensional structure similarities. A preferred method to determine a three dimensional structure of a target FcR structure comprises: (a) providing an amino acid sequence of a target structure, wherein the three dimensional structure of the target structure is not known; (b) analyzing the pattern of folding of the amino acid sequence in a three dimensional conformation by fold recognition; and (c) comparing the pattern of folding of the target structure amino acid sequence with the three dimensional structure of FcγRIIa protein to determine the three dimensional structure of the target structure, wherein the three dimensional structure of the FcγRIIa protein substantially conforms to the atomic coordinates represented in Table 1. Preferred methods of fold recognition include the methods generally described in Jones, *Curr. Opinion Struc. Biol.*, vol. 7, pp. 377-387, 1997. Such folding can be analyzed based on hydrophobic and/or hydrophilic properties of a target structure.

One embodiment includes a three dimensional computer image of the three dimensional structure of an FcR protein. Suitable structures of which to produce three dimensional computer images are disclosed herein. Preferably, a computer image is created to a structure substantially conforms with the three dimensional coordinates listed in Table 1. A computer image of the present invention can be produced using any suitable software program, including, but not limited to, MOLSCRIPT 2.0 (Avatar Software AB, Heleneborgsgatan 21 C, SE-11731 Stockholm, Sweden), the graphical display program 0 (Jones et. al., *Acta Crystallography*, vol. A47, p. 110, 1991) or the graphical display program GRASP. Suitable computer hardware useful for producing an image of the present invention are known to those of skill in the art. Preferred computer hardware includes a Silicon Graphics Workstation.

Another embodiment relates to a computer-readable medium encoded with a set of three dimensional coordinates selected from the group of the three dimensional coordinates represented in Table 1, the three dimensional coordinates represented in Table 2, the three dimensional coordinates represented in Table 3, the three dimensional coordinates represented in Table 4, and the three dimensional coordinates represented in Table 5, wherein, using a graphical display software program, the three dimensional coordinates create an electronic file that can be visualized on a computer capable of representing said electronic file as a three dimensional image. Preferably, the three dimensional structure is of an FcR protein selected from the group of FcγRIIa, FcεRI, and FcγRIIIb.

Yet another embodiment of the present invention relates to a computer-readable medium encoded with a set of three dimensional coordinates of a three dimensional structure which substantially conforms to the three dimensional coordinates represented in Table 1, wherein, using a graphical display software program, the set of three dimensional coordinates create an electronic file that can be visualized on a computer capable of representing said electronic file as a three dimensional image. Preferably, the three dimensional structure is of an FcR protein selected from the group of FcεRI, FcγRIIa, FcγRIIb, FcγRIIc, FcγRIII, FcεRI and FcαRI.

Another embodiment relates to a two dimensional image of an FcR including those illustrated in FIG. 4, FIG. 6, FIG. 7, FIG. 8, FIG. 9, FIG. 10, FIG. 14, FIG. 15 or FIG. 16. Most of these figures were drawn with MOLSCRIPT 2.0 (Avatar Software AB, Heleneborgsgatan 21 C, SE-11731 Stockholm, Sweden).

One embodiment includes an image of FcR protein that is generated when a set of three dimensional coordinates comprising the three dimensional coordinates represented in Table 1 are analyzed on a computer using a graphical display software program to create an electronic file of said image and visualizing said electronic file on a computer capable of representing electronic file as a three dimensional image. Suitable graphical software display programs include MOLSCRIPT 2.0, O and GRASP. A suitable computer to visualize such image includes a Silicon Graphics Workstation. Suitable structures and models to image are disclosed herein. Preferably, the three dimensional structures and/or models are of an FcR protein selected from the group of FcγRI, FcγRIIa, FcγRIIb, FcγRIIc, FcγRIII, FcεRI and FcαRI.

The present invention also includes a three dimensional model of the three dimensional structure of a target structure including FcγRI protein, FcγRIIa, FcRIIb protein, FcγRIIc protein, FcγRIIIb protein, FcεRI protein, and FcαRI protein, such a three dimensional model being produced by the method comprising: (a) providing an amino acid sequences of an FcγRIIa protein and an amino acid sequence of a target FcR structure; (b) identifying structurally conserved regions shared between the FcγRIIa amino acid sequence and the target FcR structure amino acid sequence; (c) determining atomic coordinates for the FcR protein by assigning the structurally conserved regions of the target FcR structure to a three dimensional structure using a three dimensional structure of an FcγRIIa protein based on atomic coordinates that substantially conform to the atomic coordinates represented in Table 1 to derive a model of the three dimensional structure of the target FcR structure amino acid sequence. Preferably, the model comprises a computer model. Preferably, the method further comprises the step of electronically simulating the structural assignments to derive a computer model of the three dimensional structure of the target FcR structure amino acid sequence. Preferred amino acid sequences of FcγRI protein, FcγRIIb protein, FcγRIIc protein, FcγRIIIb protein and FcεRI protein are disclosed herein.

One embodiment includes a method for producing crystals of FcγRIIa, comprising combining FcγRIIa protein with a mother liquor and inducing crystal formation to produce the FcγRIIa crystals. Another embodiment includes a method for producing crystals of FcεRI, comprising combining FcεRI protein with a mother liquor and inducing crystal formation to produce the FcεRI crystals. Although the production of crystals of Fc.RIIa and FcεRI are specifically described herein, it is to be understood that such processes as are described herein can be adapted by those of skill in the art to produce crystals of other Fc receptors (FcR), particularly FcγRI, FcγRIIb, FcγRIIc, FcγRIIIb and FcαRI, the three dimensional structures of which are also encompassed by the present invention.

Preferably, crystals of FcγRIIa are formed using a solution containing a range of FcγRIIa protein from about 1 mg/ml to about 20 mg/ml, more preferably from about 2 mg/ml to about 0.15 mg/ml, and even more preferably from about 3 mg/ml to about 6 mg/ml of FcγRIIa protein in a mother liquor, with 3 mg/ml and 6 mg/ml of FcγRIIa protein in a mother liquor being more preferred. Preferably, crystals are formed using droplets containing from about 1 g to about 30 µg, more preferably from about 5 µg to about 25 µg, and more preferably from about 4.5 µg to about 9 µg of FcγRIIa protein per 3 µl droplet.

A suitable mother liquor comprises an acetate salt buffer. A preferred acetate salt buffer of the present invention comprises ammonium acetate. The concentration of ammonium acetate in the buffer prior to crystallization can range from about 100 mM to about 500 mM ammonium acetate. Preferably, the concentration of ammonium acetate in the buffer ranges from about 150 mM to about 300 mM ammonium acetate. More preferably, the concentration of ammonium acetate in the buffer is 200 mM ammonium acetate. A suitable acetate salt buffer preferably includes a buffer having a pH of from about 5 to about 7, more preferably from about 5.5 to about 6.5, and more preferably a pH of about 5.6. Preferably, the pH of an acetate salt buffer or the present invention is controlled using sodium citrate. A suitable acetate salt buffer contains sodium citrate at a concentration of about 0.01 M sodium citrate, more preferably 0.05 M sodium citrate and more preferably 0.1 M sodium citrate. A suitable acetate salt buffer contains any polyethylene glycol (PEG), with PEG 4000 being more preferred. Suitable PEG 4000 concentrations in an acetate salt buffer o include a concentration of about 20%, preferably about 25%, and more preferably about 30% PEG 4000.

Another suitable mother liquor comprises a sulphate buffer. A preferred sulphate buffer of the present invention comprises lithium sulfate. The concentration of lithium sulfate in the buffer prior to crystallization can range from about 100 mM to about 2.5 M lithium sulfate. Preferably, the concentration of lithium sulfate in the buffer ranges from about 500 mM to about 2 M lithium sulfate. More preferably, the concentration of lithium sulfate in the buffer is about 1.5 M lithium sulfate. A suitable sulphate buffer preferably includes a buffer having a pH of from about 5 to about 9, more preferably from about 6 to about 8, and more preferably a pH of about 7.5. Preferably, the pH of a sulphate buffer is controlled using HEPES. A suitable sulphate buffer contains HEPES at a concentration of about 0.01 M HEPES, more preferably 0.05 M HEPES and more preferably 0.1 M HEPES.

Supersaturated solutions of FcγRIIa protein can be induced to crystallize by several methods including, but not limited to, vapor diffusion, liquid diffusion, batch crystallization, constant temperature and temperature induction or a combination thereof. Preferably, supersaturated solutions of FcγRIIa protein are induced to crystallize by vapor diffusion (i.e., hanging drop method). In a vapor diffusion method, an FcγRIIa protein is combined with a mother liquor of the present invention that will cause the FcγRIIa protein solution to become supersaturated and form FcγRIIa crystals at a constant temperature.

Vapor diffusion is preferably performed under a controlled temperature in the range of from about 15 C to about 30 C, more preferably from about 20 C to about 25 C, and more preferably at a constant temperature of about 22 C.

A preferred embodiment includes a method to produce crystals of Fc.RIIa comprising the steps of: (a) preparing an about 3 mg/ml solution of FcγRIIa protein in an acetate salt buffer to form a supersaturated formulation, in which the buffer comprises about 200 mM ammonium acetate, about 100 mM sodium citrate and about 30% PEG 4000 and has a pH of about pH 5.8; (b) dropping about 3 μl droplets of the supersaturated formulation onto a coverslip and inverting this over a well containing about 1 ml of the acetate salt buffer; and (c) incubating until crystals of FcγRIIa form.

Another preferred embodiment includes a method to produce crystals of FcγRIIa comprising the steps of: (a) preparing an about 3 mg/ml solution of FcγRIIa protein in a sulphate buffer to form a supersaturated formulation, in which the buffer comprises about 0.15 M HEPES and about 1.5 M lithium sulphate and has a pH of about pH 7.5; (b) dropping about 3 μl droplets of the supersaturated formulation onto a coverslip and inverting this over a containing about 1 ml of the sulphate buffer; and (c) incubating until crystals of FcγRIIa form.

As discussed briefly above, another embodiment of the present invention is a method of producing FcεRI crystals and the FcεRI crystals produced thereby. Preferably, crystals of FcεRI are formed using a solution containing a range of Fc RI protein from about 1 mg/ml to about 20 mg/ml, more preferably from about 2 mg/ml to about 15 mg/ml, and even more preferably from about 3 mg/ml to about 6 mg/ml of FcεRI protein in a mother liquor, with 3 mg/ml and 6 mg/ml of FcεRI protein in a mother liquor being more preferred. Preferably, crystals are formed using droplets containing from about 1 μg to about 30 μg, more preferably from about 5 μg to about 25 μg, and more preferably from about 4.5 μg to about 9 μg of FcεRI protein per 3 μl droplet.

A suitable mother liquor comprises an acetate salt buffer. A preferred acetate salt buffer of the present invention comprises calcium acetate. The concentration of calcium acetate in the buffer prior to crystallization can range from about 100 mM to about 500 mM calcium acetate. Preferably, the concentration of calcium acetate in the buffer ranges from about 150 mM to about 300 mM calcium acetate. More preferably, the concentration of calcium acetate in the buffer is 200 mM calcium acetate. A suitable acetate salt buffer preferably includes a buffer having a pH of from about 5.5 to about 7.5, more preferably from about 6.0 to about 7.0, and more preferably a pH of about 6.5. Preferably, the pH of an acetate salt buffer is controlled using sodium cacodylate. A suitable acetate salt buffer contains sodium cacodylate at a concentration of about 0.01 M sodium cacodylate, more preferably 0.05 M sodium cacodylate and more preferably 0.1 M sodium cacodylate. A suitable acetate salt buffer contains any polyethylene glycol (PEG), with PEG 8000 being more preferred. Suitable PEG 8000 concentrations in an acetate salt buffer of the present invention include a concentration of about 10% w/v, preferably about 15%, and more preferably about 20% w/v PEG 8000.

Another suitable mother liquor comprises a buffer which includes sodium cacodylate together with 2-propanol and polyethylene glycol. A preferred sodium cacodylate buffer of the present invention comprises a concentration of sodium cacodylate in the buffer prior to crystallization of about 0.01 M sodium cacodylate, more preferably 0.05 M sodium cacodylate and more preferably 0.1 M sodium cacodylate. A suitable sodium cacodylate buffer preferably includes a buffer having a pH of from about 5 to about 7, more preferably from about 5.5 to about 6.5, and more preferably a pH of from about 5.5 to about 6.0. A suitable sodium cacodylate buffer contains 2-propanol at a concentration of about 5% v/v, more preferably 7% v/v and more preferably 10% v/v. A suitable sodium cacodylate buffer contains any polyethylene glycol (PEG), with PEG 4000 being more preferred. Suitable PEG 4000 concentrations in an acetate salt buffer include a concentration of about 10% w/v, preferably about 15%, and more preferably about 20% w/v PEG 4000.

Another suitable mother liquor comprises a sodium citrate buffer which includes tri sodium citrate dihydrate together with sodium cacodylate and 2-propanol. A preferred sodium citrate buffer of the present invention comprises a concentration of tri sodium citrate dihydrate in the buffer prior to crystallization of about 0.05 M tri sodium citrate dihydrate, more preferably 0.1 M tri sodium citrate dihydrate and more preferably 0.2 M tri sodium citrate dihydrate. A suitable sodium citrate buffer preferably includes a buffer having a pH of from about 5.5 to about 7, more preferably from about 6.0 to about 7.0, and more preferably a pH of about 6.5. A preferred sodium citrate buffer comprises a concentration of sodium cacodylate in the buffer prior to crystallization of about 0.01 M sodium cacodylate, more preferably 0.05 M sodium cacodylate and more preferably 0.1 M sodium cacodylate. A suitable sodium citrate buffer contains 2-propanol at a concentration of about 15% v/v, more preferably 20% v/v and more preferably 30% v/v.

Supersaturated solutions of FcεRI protein can be induced to crystallize by several methods including, but not limited to, vapor diffusion, liquid diffusion, batch crystallization, constant temperature and temperature induction or a combination thereof. Preferably, supersaturated solutions of FcεRI protein are induced to crystallize by vapor diffusion (i.e., hanging drop method). In a vapor diffusion method, an Fc RI protein is combined with a mother liquor that will cause the FcεRI protein solution to become supersaturated and form FcεRI crystals at a constant temperature. Vapor diffusion is preferably performed under a controlled temperature in the range of from about 15 C to about 30 C, more preferably from about 20 C to about 25 C, and more preferably at a constant temperature of about 22 C.

A preferred embodiment includes a method to produce crystals of FcεRI comprising the steps of: (a) preparing an about 3 mg/ml solution of FcεRI protein in an acetate salt buffer to form a supersaturated formulation, in which the buffer comprises about 200 mM calcium acetate, about 100 mM sodium cacodylate and about 18% w/v PEG 8000 and has a pH of about pH 6.5; (b) dropping about 3 μl droplets of the supersaturated formulation onto a coverslip and inverting this over a well containing about 1 ml of the acetate salt buffer; and (c) incubating until crystals of FcεRI form.

Another preferred embodiment includes a method to produce crystals of FcεRI comprising the steps of: (a) preparing an about 3 mg/ml solution of FcεRI protein in a sodium cacodylate buffer to form a supersaturated formulation, in which the buffer comprises about 100 mM sodium cacodylate, about 10% v/v 2-propanol and about 20% w/v PEG 4000 and has a pH of about pH 5.5-6.0; (b) dropping about 3 ul droplets of the supersaturated formulation onto a coverslip and inverting this over a containing about 1 ml of the sulphate buffer; and (c) incubating until crystals of FcεRI form.

Yet another preferred embodiment includes a method to produce crystals of FcεRI comprising the steps of: (a) preparing an about 3 mg/ml solution of FcεRI protein in a sodium citrate buffer to form a supersaturated formulation, in which the buffer comprises about 200 mM tri sodium citrate dihydrate, about 100 mM sodium cacodylate and about 30% v/v 2-propanol and has a pH of about pH 6.5; (b) dropping about 3 ul droplets of the supersaturated formulation onto a coverslip and inverting this over a containing about 1 ml of the sulphate buffer; and (c) incubating until crystals of FcεRI form.

Any isolated FcR protein can be used with the present method. An isolated FcR protein can be isolated from its natural milieu or produced using recombinant DNA technology (e.g., polymerase chain reaction (PCR) amplification, cloning) or chemical synthesis. To produce recombinant FcR protein, a nucleic acid molecule encoding FcR protein can be inserted into any vector capable of delivering the nucleic acid molecule into a host cell. Suitable and preferred nucleic acid molecules to include in recombinant vectors of the present invention are as disclosed herein. A preferred nucleic acid molecule of the present invention encodes a human FcR protein, and more preferably, a human FcγRIIa protein, a human FcεRI protein, or a human FcγRIIIb protein. A nucleic acid molecule can encode any portion of an FcR protein, preferably a full-length FcR protein, and more preferably a soluble form of FcR protein (i.e., a form of FcR protein capable of being secreted by a cell that produces such protein). A more preferred nucleic acid molecule to include in a recombinant vector, and particularly in a recombinant molecule, includes a nucleic acid molecule encoding a protein having the amino acid sequence represented by SEQ ID NO:3, SEQ ID NO:5, SEQ ID NO:6, SEQ ID NO:7, SEQ ID NO:8, SEQ ID NO:9, SEQ ID NO:10, SEQ ID NO:11, SEQ ID NO:12, or SEQ ID NO:13. A preferred nucleic acid molecule to include in a recombinant molecule includes sFcγRIIa and sFcεRI, the production of which are described in the Examples section.

A recombinant vector can be either RNA or DNA, either prokaryotic or eukaryotic, and typically is a virus or a plasmid. Preferably, a nucleic acid molecule encoding an FcR protein is inserted into a vector comprising an expression vector to form a recombinant molecule. As used herein, an expression vector is a DNA or RNA vector that is capable of transforming a host cell and of affecting expression of a specified nucleic acid molecule. Expression vectors of the present invention include any vectors that function (i.e., direct gene expression) in recombinant cells, including in bacterial, fungal, endoparasite, insect, other animal, and plant cells. Preferred expression vectors direct expression in insect cells. A more preferred expression vector comprises pVL1392 baculovirus shuttle plasmid. A preferred recombinant molecule comprises pVL-sFcγRIIa(a), pVL-sFcγRIIa(b), and pVL-sFcεRI.

An expression vector can be transformed into any suitable host cell to form a recombinant cell. A suitable host cell includes any cell capable of expressing a nucleic acid molecule inserted into the expression vector. For example, a prokaryotic expression vector can be transformed into a bacterial host cell. A preferred host cell includes a cell capable of expressing a baculovirus, in particular an insect cell, with Spodoptera frugiperda or Trichoplusia ni cells being preferred. A preferred recombinant cell includes S. frugiperda: pVL-sFcγRIIa(a)/pVL-sFcγRIIa(b) cells and S. frugiperda: pVL-sFcεRI the production of which is described herein.

One method to isolate FcR protein useful for producing FcR crystals includes recovery of recombinant proteins from cell cultures of recombinant cells expressing such FcR protein. In one embodiment, an isolated recombinant FcR protein is produced by culturing a cell capable of expressing the protein under conditions effective to produce the protein, and recovering the protein. A preferred cell to culture is a recombinant cell of the present invention. Effective culture conditions include, but are not limited to, effective media, bioreactor, temperature, pH and oxygen conditions and culture medium that permit protein production. Such culturing conditions are within the expertise of one of ordinary skill in the art. Examples of suitable conditions are included in the Examples section.

Preferably, a recombinant cell expresses a secreted form of FcR protein. FcR proteins can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, chromatofocusing and differential solubilization. Preferably, an FcR protein is purified in such a manner that the protein is purified sufficiently for formation of crystals useful for obtaining information related to the three dimensional structure of an FcR protein. Preferably, a composition of FcR protein is about 70%, more preferably 75%, more preferably 80%, more preferably 85% and more preferably 90% pure.

In one embodiment, a recombinant FcR protein is purified from a cell culture supernatant harvested between about 20 hours and about 60 hours post-infection, preferably between about 30 hours and about 50 hours post-infection, and more preferably about 40 hours post-infection. Preferably, an FcγRIIa protein is purified from a supernatant by a method comprising the steps: (a) applying supernatant from S. frugiperda: pVL-sFc.RIIa (a)/pVL-sFcγRIIa(b) cells to an ion exchange column; (b) collecting unbound protein from the ion exchange column and applying the unbound protein to an immuno-affinity chromatography column; (c) eluting proteins bound to the immuno-affinity chromatography column and applying the eluted proteins to a gel filtration column; and (d) collecting filtered proteins from the gel filtration column to obtain the Fc.RIIa protein. Preferably, an Fc RI protein is purified from a supernatant by a method comprising the steps: (a) applying supernatant from S. frugiperda: pVL-sFc RI cells to an ion exchange column; (b) collecting unbound protein from the ion exchange column and applying the unbound protein to an immuno-affinity chromatography column; (c) eluting proteins bound to the immuno-affinity chromatography column and applying the eluted proteins to a gel filtration column; and (d) collecting filtered proteins from the gel filtration column to obtain the FcεRI protein.

In view of the high degree of amino acid sequence homology between human FcγR proteins and other members of the FcγR family of proteins, the methods of purification are applicable for each member of the FcγR family. In addition, one of skill in the art will recognize that the purification methods of the present invention are generally useful for purifying any FcR protein, such as the FcεRI protein, except using IgE rather than IgG for the step of immuno-affinity chromatography purification, and such as the FcαRI protein, except using IgA rather than IgG for the purification step. Isolated protein of the members of the FcγR family of proteins, FcεR protein and FcαR protein may be obtained through recombinant DNA technology or may be purified from natural sources, including but not limited to, monocytes, macrophages, neutrophils, eosinophils, platelets and B lymphocytes (i.e., B cells). Descriptions of recombinant production of isolated Fc.RIIa and Fc.RI proteins are described in the Examples section.

Another embodiment includes a composition comprising FcR protein in a crystalline form (i.e., FcR crystals). As used herein, the terms "crystalline FcR" and "FcR crystal" both refer to crystallized FcR protein and are intended to be used interchangeably. Preferably, a crystalline FcR is produced using the crystal formation method described herein, in particular according to the method disclosed in Example 6 or Example 9. A FcR crystal of the present invention can comprise any crystal structure and preferably precipitates as an orthorhombic crystal. A suitable crystalline FcR of the present invention includes a monomer or a multimer of FcR protein. A preferred crystalline FcR comprises one FcR protein in an asymmetric unit. A more preferred crystalline FcR comprises a dimer of FcR proteins.

A particular embodiment includes a composition comprising FcγRIIa protein in a crystalline form (i.e., Fc.RIIa crystals). As used herein, the terms "crystalline FcγRIIa" and "FcγRIIa crystal" both refer to crystallized FcγRIIa protein and are intended to be used interchangeably. Preferably, a crystal FcγRIIa is produced using the crystal formation method described herein, in particular according to the method disclosed in Example 6. A FcγRIIa crystal of the present invention can comprise any crystal structure and preferably precipitates as an orthorhombic crystal. Preferably, a composition of the present invention includes FcγRIIa protein molecules arranged in a crystalline manner in a space group $P2_12_12$, so as to form a unit cell of dimensions a=78.80 Å, b=100.55 Å, c=27.85 Å. A preferred crystal of the present invention provides X-ray diffraction data for determination of atomic coordinates of the Fc.RIIa protein to a resolution of about 3.0 Å, preferably about 2.4 Å, and more preferably at about 1.8 Å.

A suitable crystalline FcγRIIa of the present invention includes a monomer or a multimer of FcγRIIa protein. A preferred crystalline FcγRIIa comprises one FcγRIIa proteins in an asymmetric unit. A more preferred crystalline FcγRIIa comprises a dimer of FcγRIIa proteins.

Another particular embodiment includes a composition comprising FcεRI protein in a crystalline form (i.e., FcεRI crystals). As used herein, the terms "crystalline Fc .RI" and "FcεRI crystal" both refer to crystallized FcRI protein and are intended to be used interchangeably. Preferably, a crystal FcεRI is produced using the crystal formation method described herein, in particular according to the method disclosed in Example 9. A FcεRI crystal can comprise any crystal structure and preferably precipitates as an orthorhombic crystal. A suitable crystalline FcεRI includes a monomer or a multimer of FcεRI protein. A preferred crystalline FcεRI comprises one FcεRI protein in an asymmetric unit. A more preferred crystalline FcεRI comprises a dimer of FcεRI proteins.

Crystalline FcR can be used to determine the ability of a chemical compound to bind to FcγRIIa protein a manner predicted by a structure based drug design method as described herein. Preferably, an FcγRIIa crystal is soaked in a solution containing a chemical compound of the present invention. Binding of the chemical compound to the crystal is then determined by methods standard in the art.

One embodiment is a therapeutic composition comprising one or more therapeutic compounds. Preferred therapeutic compounds include inhibitory compounds and stimulatory compounds.

One embodiment is a therapeutic composition that is capable of reducing IgG-mediated tissue damage. Suitable therapeutic compositions are capable of reducing IgG-mediated tissue damage resulting from IgG-mediated hypersensitivity or other biological mechanisms involved in IgG-mediated recruitment of inflammatory cells that involves FcγR protein. For example, a therapeutic composition can: (1) inhibit (i.e., prevent, block) binding of FcγR protein on a cell having an FcγR protein (e.g., B cells, macrophage, neutrophil, eosinophil or platelet cells) to an IgG immune complex by interfering with the IgG binding site of an FcγR protein; (2) binding to the Fc portion of IgG to inhibit complement fixation by an IgG immune complex by interfering with the complement binding site of an IgG molecule; (3) inhibit precipitation of IgG or IgG immune complexes (i.e., prevent Fc:Fc interactions between two IgG); (4) inhibit immunoglobulin-mediated cellular signal transduction by interfering with the binding of an IgG to a cell surface receptor; (5) inhibit FcγR-mediated cellular signal transduction by interfering with the binding of a cell signal inducing molecule (i.e., a molecule that induces cellular signal transduction through an FcγR protein) to an FcγR protein; (6) inhibit opsinization of pathogens by inhibiting binding of IgG bound to a pathogen to FcγR protein on a phagocytic cell (e.g., to prevent antibody dependent enhancement (ADE) of viral infection, such as with flaviviruses and dengue virus); and (7) inhibit the binding of viral molecules to FcγR protein (e.g., measles virus nucleocapsid protein). As used herein, the term "immune complex" refers to a complex that is formed when an antibody binds to a soluble antigen. As used herein, the term "complement fixation" refers to complement activation by an antigen:antibody complex that results in recruitment of inflammatory cells, typically by assembly of a complex comprising C3a and C5a, or generation of cleaved C4. As used herein, the term "binding site" refers to the region of a molecule (e.g., a protein) to which another molecule specifically binds. Such therapeutic compositions include one or more inhibitory compounds that inhibit binding of IgG to Fc.R protein, IgG to complement, IgG to IgG, IgG to a cell surface receptor, a cell signal inducing molecule to Fc.R protein, Fc.R protein to virus or inhibit opsinization. Also included in the present invention are methods to reduce IgG-mediated tissue damage. The method includes the step of administering to an animal a therapeutic composition of the present invention.

Another embodiment is a therapeutic composition that is capable of stimulating an IgG humoral immune response in an animal. Yet another embodiment is a therapeutic composition that improves the therapeutic affects of an antibody that is administered to an animal to treat, by opsinization or FcγR-dependent effector functions (e.g. antibody-dependent FcγR-mediated cytotoxicity, phagocytosis or release of cellular mediators), a particular disease, including, but not limited to, cancer or infectious disease (e.g. oral infections such as HIV, herpes, bacterial infections, yeast infections or parasite infections). Such a therapeutic composition includes one or more stimulatory compounds that have increased binding to IgG, enhance binding of IgG to FcγR, enhance dimer formation of an FcγR and/or enhance signal transduction through the FcγR. Also included in the present invention is a method to stimulate a humoral immune response. The method includes the step of administering to an animal a therapeutic composition of the present invention.

Suitable inhibitory compounds are compounds that interact directly with an FcγR protein, preferably an FcγRIIa protein or an FcγRIIIb protein, thereby inhibiting the binding of IgG to an FcγR protein, by either blocking the IgG binding site of an FcγR (referred to herein as substrate analogs) or by modifying other regions of the FcγR protein (such as in the upper groove of the IgG binding cleft between the monomers of an FcγR dimer, at the dimer interface, in the cleft or hinge region between D1 and D2 on each monomer, and/or underneath the IgG binding cleft in the lower groove formed by the monomers of an FcγR dimer) such that IgG cannot bind to the FcγR (e.g., by allosteric interaction). A FcγR substrate analog refers to a compound that interacts with (e.g., binds to, associates with, modifies) the IgG binding site of an Fc.R protein. A FcγR substrate analog can, for example, comprise a chemical compound that mimics the Fc portion of an IgG, or that binds specifically to the IgG binding site of an FcγR but does not mimic the Fc portion of an IgG. An inhibitory compound of the present invention can also include a compound that essentially mimics at least a portion of an FcγRIIa protein that binds to IgG (referred to herein as a peptidomimetic compound). Other suitable inhibitory compounds of the present invention include compounds that inhibit the binding of an FcγR protein to a cell signal inducing molecule other than IgG. Examples of such cell signal inducing molecules include another FcγR (i.e., to form a dimer of FcγR proteins), or a cell surface accessory molecule, an intracellular accessory molecule or virus (e.g., measles virus nucleocapsid protein).

One embodiment of the present invention is a therapeutic composition that is capable of reducing IgE-mediated responses. Suitable therapeutic compositions are capable of reducing IgE-mediated responses resulting from IgE-mediated hypersensitivity, IgE-mediated release of inflammatory modulators or other biological mechanisms involved in IgE-mediated recruitment of inflammatory cells that involves FcεR protein. For example, a therapeutic composition of the present invention can: (1) inhibit (i.e., prevent, block) binding of FcεR protein on a cell having an FcεR protein (e.g., mast cells) to an IgE immune complex by interfering with the IgE binding site of an FcεR protein; (2) inhibit precipitation of IgE or IgE immune complexes (i.e., prevent Fc:Fc interactions between two IgE); (3) inhibit immunoglobulin-mediated cellular signal transduction by interfering with the binding of an IgE to a cell surface receptor; and (4) inhibit FcεR-mediated cellular signal transduction by interfering with the binding of a cell signal inducing molecule (i.e., a molecule that induces cellular signal transduction through an FcεR protein) to an FcεR protein. Such therapeutic compositions include one or more inhibitory compounds that inhibit binding of IgE to FcεR protein, IgE to IgE, IgE to a cell surface receptor, or a cell signal inducing molecule to FcεR protein. Also included in the present invention are methods to reduce IgE-mediated responses, such as IgE-mediated inflammation. The method includes the step of administering to an animal a therapeutic composition of the present invention.

Another embodiment of the present invention is a therapeutic composition that is capable of stimulating a IgE humoral immune response in an animal. Yet another embodiment of the present invention is a therapeutic composition that improves the therapeutic affects of an antibody that is administered to an animal to treat, by opsinization or FcεR-dependent effector functions (e.g. phagocytosis or release of cellular mediators), a particular disease. Such a therapeutic composition includes one or more stimulatory compounds that have increased binding to IgE, enhance binding of IgE to FcεRI, enhance dimer formation of FcεRI and/or otherwise enhance signal transduction through the FcεRI. Also included in the present invention is a method to stimulate a humoral immune response. The method includes the step of administering to an animal a therapeutic composition of the present invention.

Suitable inhibitory compounds of the present invention are compounds that interact directly with an FcεR protein, thereby inhibiting the binding of IgE to an FcεR protein, by either blocking the IgE binding site of an FcεR (referred to herein as substrate analogs) or by modifying other regions of the FcεR protein (such as in the upper groove of the IgE binding cleft between the monomers of an FcεRI dimer, at the dimer interface, in the cleft or hinge region between D1 and D2 on each monomer, and/or underneath the IgE binding cleft in the lower groove formed by the monomers of an FcεRI dimer) such that IgE cannot bind to the FcεR (e.g., by allosteric interaction). A FcεR substrate analog refers to a compound that interacts with (e.g., binds to, associates with, modifies) the IgE binding site of an FcεR protein. A FcεR substrate analog can, for example, comprise a chemical compound that mimics the Fc portion of an IgE, or that binds specifically to the IgE binding site of an FcεR but does not mimic the Fc portion of an IgE. An inhibitory compound of the present invention can also include a compound that essentially mimics at least a portion of an FcεR protein that binds to IgE (referred to herein as a peptidomimetic compound). Other suitable inhibitory compounds of the present invention include compounds that inhibit the binding of an FcεR protein to a cell signal inducing molecule other than IgE. Examples of such cell signal inducing molecules include another FcεR (i.e., to form a dimer of FcεR proteins), or a cell surface accessory molecule, an intracellular accessory molecule or virus (e.g., measles virus nucleocapsid protein).

Inhibitory compounds of the present invention can be identified by various means known to those of skill in the art. For example, binding of an inhibitory compound to, or otherwise interaction with, an FcR protein, can be determined with FcR protein in solution or on cells using, for example, immunoassays such as enzyme linked immunoabsorbent assays (ELISA) and radioimmunoassays (RIA) or binding assays such as Biacore assays. Cell-based assays can include, for example, cytokine (e.g., IL-4, IL-6 or IL-12) secretion assays, or intracellular signal transduction assays that determine, for example, protein or lipid phosphorylation, mediator release or intracellular $Ca^{++}$ mobilization upon FcR binding to a cell signal inducing molecule.

Suitable stimulatory therapeutic compounds of the present invention are compounds that exhibit improved binding to Ig when compared with the ability of a natural FcR protein (e.g., an FcR protein isolated from its natural milieu) to bind to Ig, and also include compounds that enhance the binding of Ig to its FcR or enhance signal transduction through the FcR. Stimulatory compounds of the present invention are identified by their ability to: (1) bind to, or otherwise interact with, Ig at a higher level than, for example, natural FcR protein; (2) enhance binding of Ig to its FcR; (3) enhance dimer formation of an FcR by binding either to the FcR, to an Ig that binds to the FcR or to the combination of Ig bound to the FcR; and/or (4) enhance signal transduction through the FcR. Methods to determine improved binding of Ig to a stimulatory compound of the present invention compared with, for example, natural FcR protein, include binding assays that determine the stability of binding, affinity or kinetics at which an Ig binds to a stimulatory compound and a natural FcR protein. Such methods are well known to those of skill in the art and are disclosed herein in the Examples section. A stimulatory compound of the present invention can also include a compound that binds to an Ig or an FcR protein, thereby enhancing the binding of Ig to FcR protein or improving cellular signal transduction during or after the binding of Ig to FcR protein, by, for example, modifying other regions of the FcR or Ig by an allosteric interaction that modifies the Ig-binding site of FcR or the Fc portion of Ig that binds to an FcR protein. Another stimulatory compound of the present invention can include a compound that binds to FcR protein in the absence of Ig, in such a manner that FcR-mediated cellular signal transduction is stimulated.

One of skill in the art will understand that inhibitory or stimulatory compounds can also be developed based on the structure of any FcR and its Ig ligand, as described above for FcγR protein and IgG and FcεRI and IgE.

According to the present invention, suitable therapeutic compounds of the present invention include peptides or other organic molecules, and inorganic molecules. Suitable organic molecules include small organic molecules. Preferably, a therapeutic compound of the present invention is not harmful (e.g., toxic) to an animal when such compound is administered to an animal. Peptides refer to a class of compounds that is small in molecular weight and yields two or more amino acids upon hydrolysis. A polypeptide is comprised of two or more peptides. As used herein, a protein is comprised of one or more polypeptides. Preferred therapeutic compounds to design include peptides composed of "L" and/or "D" amino acids that are configured as normal or retroinverso peptides, peptidomimetic compounds, small organic molecules, or homo- or hetero-polymers thereof, in linear or branched configurations.

Therapeutic compounds of the present invention can be designed using structure based drug design. Until the discovery of the three dimensional structure of the present invention, no information was available for structure based development of therapeutic compounds based on the structure of FcR protein. Such rational development heretofore could not be executed de novo from available linear amino acid sequence information. Structure based drug design refers to the use of computer simulation to predict a conformation of a peptide, polypeptide, protein, or conformational interaction between a peptide or polypeptide, and a therapeutic compound. For example, generally, for a protein to effectively interact with a therapeutic compound, it is necessary that the three dimensional structure of the therapeutic compound assume a compatible conformation that allows the compound to bind to the protein in such a manner that a desired result is obtained upon binding. Knowledge of the three dimensional structure of the protein enables a skilled artisan to design a therapeutic compound having such compatible conformation. For example, knowledge of the three dimensional structure of the IgG binding site of FcγRIIa protein enables one of skill in the art to design a therapeutic compound that binds to FcγRIIa, is stable and results in inhibition of a biological response such as IgG binding to cells having Fc.R, or cellular signal transduction, upon such binding. In addition, for example, knowledge of the three dimensional structure of the IgG binding site of FcγRIIa protein enables a skilled artisan to design a substrate analog of FcγRIIa protein.

Suitable structures and models useful for structure based drug design are disclosed herein. Preferred structures to use in a method of structure based drug design include a structure of FcγRIIa protein, a structure of FcεRI protein, a structure of an FcγRIIIb protein, and a model of a target FcR structure. Preferred models of target structures to use in a method of structure based drug design include models produced by any modeling method disclosed herein, including molecular replacement and fold recognition related methods.

One embodiment of the present invention is a computer-assisted method of structure based drug design of bioactive compounds, comprising: (a) providing a structure of a protein including a three dimensional structure of an FcR protein or a model of the present invention; (b) designing a chemical compound using the three dimensional structure or model; and (c) chemically synthesizing the chemical compound. Such a method can additionally include the step of (d) evaluating the bioactivity of the synthesized chemical compound. Suitable three dimensional structures an FcR protein and models to use with the present method are disclosed herein. According to the present invention, the step of designing can include creating a new chemical compound or searching databases of libraries of known compounds (e.g., a compound listed in a computational screening database containing three dimensional structures of known compounds). Designing can also be performed by simulating chemical compounds having substitute moieties at certain structural features. The step of designing can include selecting a chemical compound based on a known function of the compound. A preferred step of designing comprises computational screening of one or more databases of compounds in which the three dimensional structure of the compound is known and is interacted (e.g., docked, aligned, matched, interfaced) with the three dimensional structure of an FcR protein by computer (e.g. as described by Humblet and Dunbar, *Animal Reports in Medicinal Chemistry*, vol. 28, pp. 275-283, 1993, M Venuti, ed., Academic Press). Methods to synthesize suitable chemical compounds are known to those of skill in the art and depend upon the structure of the chemical being synthesized. Methods to evaluate the bioactivity of the synthesized compound depend upon the bioactivity of the compound (e.g., inhibitory or stimulatory) and are disclosed herein.

Various other methods of structure-based drug design are disclosed in Maulik et al., 1997, *Molecular Biotechnology: Therapeutic Applications and Strategies*, Wiley-Liss, Inc., which is incorporated herein by reference in its entirety. Maulik et al. disclose, for example, methods of directed design, in which the user directs the process of creating novel molecules from a fragment library of appropriately selected fragments; random design, in which the user uses a genetic or other algorithm to randomly mutate fragments and their combinations while simultaneously applying a selection criterion to evaluate the fitness of candidate ligands; and a grid-based approach in which the user calculates the interaction energy between three dimensional receptor structures and small fragment probes, followed by linking together of favorable probe sites.

Preferably, a chemical compound of the present invention that binds to the Ig binding site of an FcR protein is known to originate from a chemical compound having chemical and/or stereochemical complementarity with FcR protein and/or Ig. Such complementarity is characteristic of a chemical compound that matches the surface of the receptor either in shape or in distribution of chemical groups and binds to FcR protein to promote or inhibit Ig binding to the FcR protein, or to induce cellular signal transduction upon binding to FcR protein. More preferably, a chemical compound that binds to the Ig binding site of an FcR protein associates with an affinity of at least about $10^{-6}$ M, and more preferably with an affinity of at least about $10^{-8}$ M.

Figure 17:
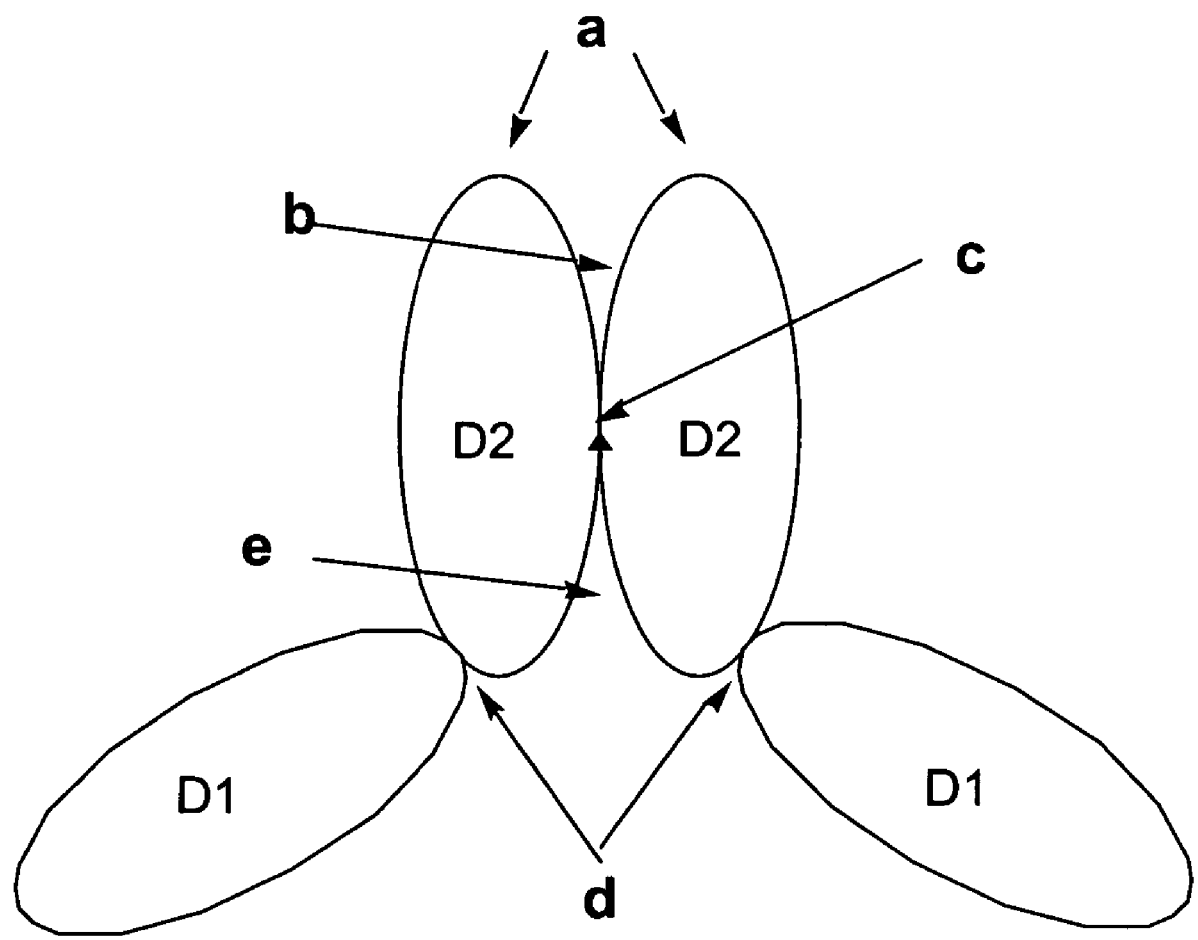

Preferably, five sites of FcR protein are targets for structure based drug design. These sites include the Ig-binding site of FcR protein, the upper groove between two FcR monomers, the dimerization interface between two FcR protein monomers, the lower groove between two FcR monomers, the interface, cleft or hinge region between Domains 1 and 2 of FcR protein, and combinations of any of these sites (e.g., interacting with the Ig-binding site and the upper groove between monomers simultaneously). A schematic representation of these sites is shown in FIG. 17, with "a" representing the Ig-binding site of FcR protein, "b" representing the upper groove between two FcR monomers, "c" representing the dimerization interface between two FcR protein monomers, "d" representing the interface, cleft or hinge region between Domains 1 and 2 of FcR protein, and "e" representing the lower groove between two FcR monomers. The following discussion provides specific detail on drug-design using target sites of the FcR and as an example, references preferred target sites on the FcγRIIa structure. It is to be understood, however, that one of skill in the art, using the description of the FcεRI structure and the FcγRIIIb structure provided herein, will be able to effectively select similar target sites on the FcεRI protein monomer and dimer for structure based drug design. Additionally, one of skill in the art, now being able to model the other FcR proteins based on the information provided herein, will also be able to effectively select similar target sites on the other FcR proteins for structure based drug design.

Figure 7:
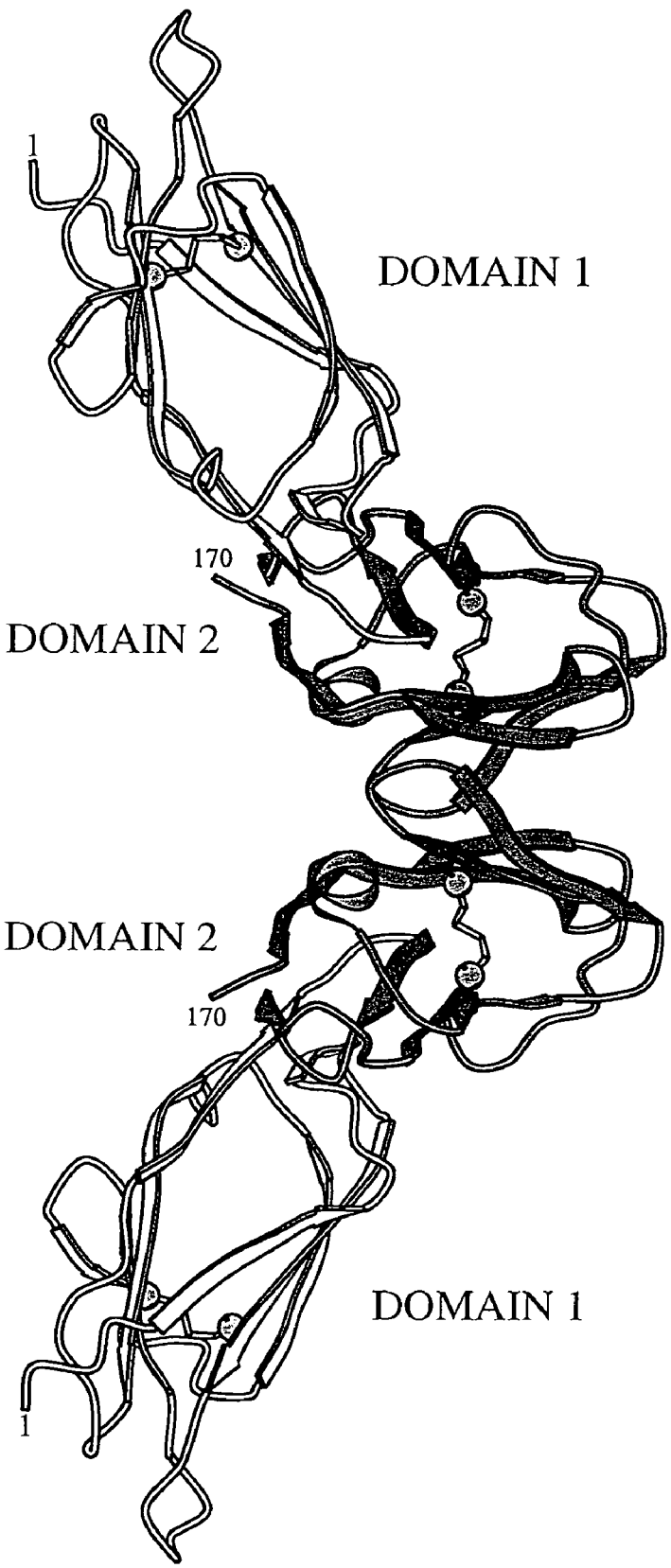

The Ig-binding site (FIG. 17; "a") is targeted to directly affect the binding of FcR to Ig (i.e., inhibition or enhancement). The IgG binding site of FcγRIIa protein, for example, includes, but is not limited to, residues 155, 156, 158-160, 113-116, 129, 131, 133 and 134 of SEQ ID NO:3, and can also include at least a portion of the second site described above (FIG. 17; "b"), the groove between the two IgG binding sites that form upon dimerization of FcγRIIa protein. Residues from site "b" that are included in IgG binding include, but are not limited to, residues 117-121, 125-129, 150-154 and 157-161 of SEQ ID NO:3. A suitable target site for structure based drug design comprising the IgG binding site of Fc.RIIa protein is illustrated in FIG. 7. More specifically, mutagenesis studies have identified several residues which have an effect on the binding of IgG, and the three dimensional structure disclosed herein clearly identifies which residues are surface exposed (i.e., are likely to participate in binding of IgG and are not just having an allosteric effect). These residues can be classified in three spatial groups: (1) Phe129, His131, Lys113, Pro114, Leu115, Val116; (2) Pro134 and Asp133; and (3) Leu159 and Ser161. Group (1) forms a continuous surface leading from the lip of the groove "b" (FIG. 17) across the binding surface "a" (FIG. 17), and represents the most preferred target of design work at the site of IgG binding. Group (2) is separated from Group (1) by Leu132, which is currently of unknown importance in the binding of IgG, and may well be part of the surface exposed residues. Group (3) contains residues which are remote from the other two groups and do not appear to be available to participate in binding of the IgG by the dimer structure.

The upper groove between the two monomers of the FcR (FIG. 17; "b") is also targeted to directly affect the binding of FcR to Ig (i.e., inhibition or enhancement). The upper groove provides an attractive site to build into in contrast to targeting a flat protein surface. The dimer structure of the FcγRIIa protein suggests targeting C2 or pseudo C2 symmetric inhibitors. Preferred residues to target in the Fc.RIIa protein include Lys117, His131, Phe129, Asn154, Ser161, Leu159, Thr152 and Phe121, with Phe129, Lys117 and His131 being most preferred. In one embodiment, compounds can be designed which interact with both the upper groove "b" and the IgG binding surface "a" simultaneously. For example, improved Ig regulatory compounds may be obtained by designing regulatory compounds which flow out of the groove and bind to the binding surface of "a" as described above. Alternatively, a regulatory compound which binds to "b" may sterically hinder binding of IgG to "a" without actually interacting with the "a" binding surface.

Figure 10:
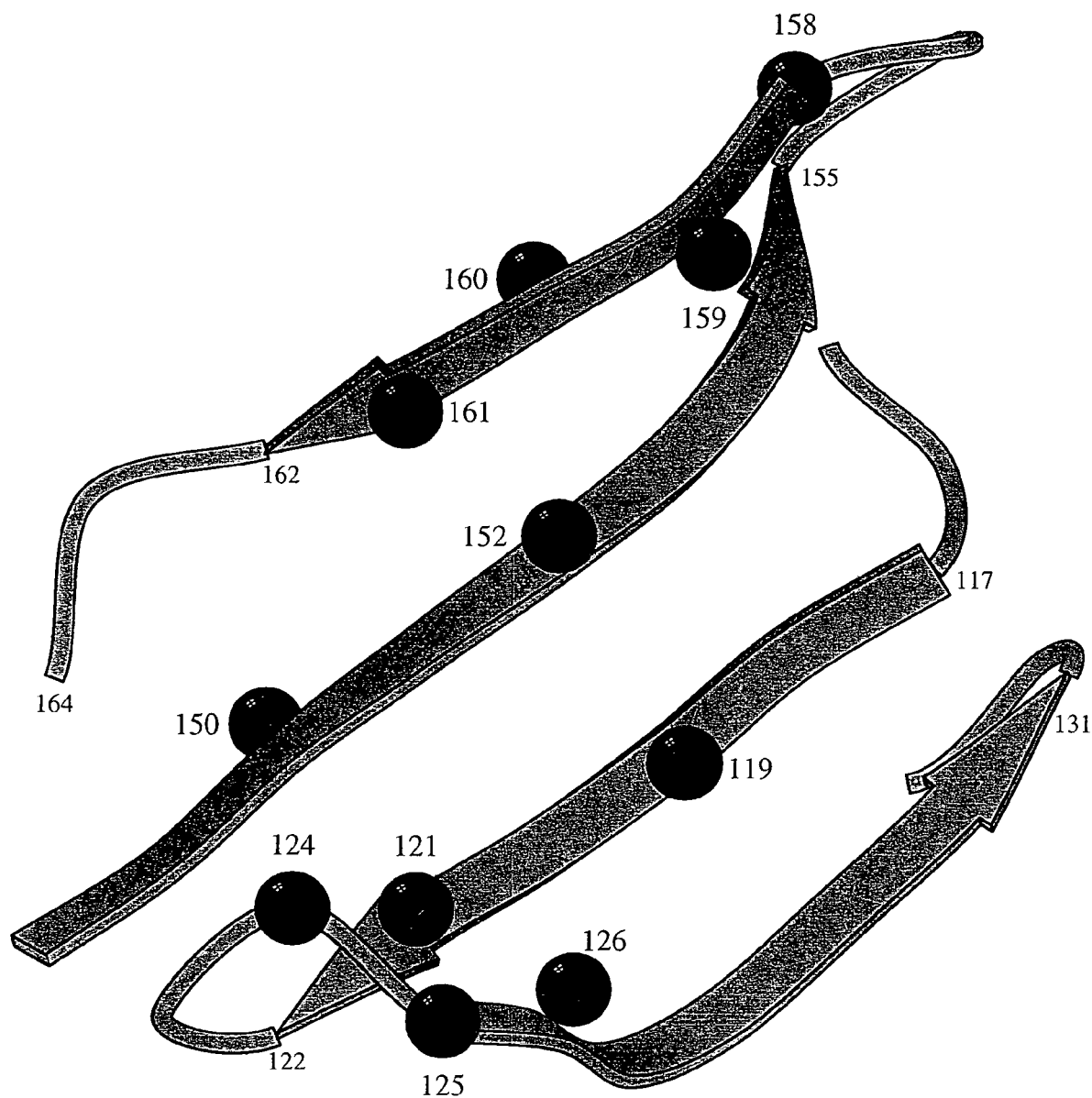

The receptor dimer interface (FIG. 17; "c") is targeted to directly affect the ability of two FcR proteins to form a dimer, thereby affecting cellular signal transduction through one or both of the FcR proteins. Without being bound by theory, the present inventors believe that dimer formation can affect cellular signal transduction or affect the conformation of the Ig binding of one or both of the FcR proteins involved in the dimer, thereby affecting cellular signal transduction. In addition, the dimer interface represents an excellent target site because one monomer provides ligand information for the other monomer and vice versa. A suitable target site for structure based drug design comprising the dimerization interface between two FcγRIIa proteins is illustrated in FIG. 10. More specifically, residues 117-131 and residues 150-164 make up the interfacial area of the FcγRIIa dimer, and peptides from these sequences or their mimics may be binding inhibitors. An examination of hydrogen bonding interactions from the crystal structure of FcγRIIa indicates relatively few interactions between the monomers in the interfacial area, but a notable cluster is spanned by the hexapeptide Phe121-Gln122-Asn123-Gly124-Lys125-Ser126. Additionally, there is a hydrogen bond between the monomers involving Gly124-Ser561 and Ser126-Leu559. There are also some hydrophobic contacts made by the Lys125 sidechain and by the Phe121 phenyl ring.

The interface between Domains 1 and 2 (FIG. 17; "d") is targeted to affect IgG binding to an FcγRIIa protein. The present inventors have discovered that in the three dimensional structure of FcγRIIa protein, Domain 1 makes close contact with Domain 2. In particular, a loop comprising residues 17-20 of SEQ ID NO:3 in Domain 1 lie close to the loops of Domain 2 to form at least a portion of the IgG-binding site. Interactions with IgG are believed to occur close to the D1D2 interface and so alterations at this site may effect Ig binding. Additionally, a cleft is defined by residues 12-14 (base), 6-10 and 77-80 (D1 face) and 93-96 and 101 (D2 face), and as such represents a potential site for inhibitor design. A suitable target site for structure based drug design comprising the interface between Domain 1 and Domain 2 of an FcγRIIa protein is illustrated in FIG. 5.

The lower groove between the two monomers of the FcR (FIG. 17; "e") is also targeted to directly affect the binding of FcR to Ig (i.e., inhibition or enhancement). A similar design strategy can be used for this site as described above for the upper groove "b", although it is less clear whether compounds binding to this site would be inhibitory, or more probably enhance IgG binding to the FcγR.

Drug design strategies as specifically described above with regard to residues and regions of the Fc.RIIa monomer and dimer can be similarly applied to the other FcR structures, including the FcγRIIIb and FcεRI structures disclosed herein. One of ordinary skill in the art, using the art recognized modeling programs and drug design methods, many of which are described herein, will be able to modify the FcγRIIa design strategy according to differences in amino acid sequence and more favored structures, for example, in the other FcR, to similarly design compounds which regulate other FcR action. In addition, one of skill in the art could use lead compound structures derived from one FcR, such as the FcγRIIa protein, and taking into account differences in amino acid residues in another FcR protein, such as FcεRI, modify the FcγRIIa lead compound to design lead compound structures for regulation of the FcεRI protein. For example, His131>Tyr131 in the upper groove pharmacophore could be accommodated by changing an acidic moiety in an FcγRIIa lead compound structure to an electron deficient ketone moiety.

In the present method of structure based drug design, it is not necessary to align a candidate chemical compound (i.e., a chemical compound being analyzed in, for example, a computational screening method of the present invention) to each residue in a target site. Suitable candidate chemical compounds can align to a subset of residues described for a target site. Preferably, a candidate chemical compound comprises a conformation that promotes the formation of covalent or noncovalent crosslinking between the target site and the candidate chemical compound. Preferably, a candidate chemical compound binds to a surface adjacent to a target site to provide an additional site of interaction in a complex. When designing an antagonist (i.e., a chemical compound that inhibits the binding of a ligand to FcR protein by blocking a binding site or interface), the antagonist should bind with sufficient affinity to the binding site or to substantially prohibit a ligand (i.e., a molecule that specifically binds to the target site) from binding to a target area. It will be appreciated by one of skill in the art that it is not necessary that the complementarity between a candidate chemical compound and a target site extend over all residues specified here in order to inhibit or promote binding of a ligand.

In general, the design of a chemical compound possessing stereochemical complementarity can be accomplished by means of techniques that optimize, chemically or geometrically, the "fit" between a chemical compound and a target site. Such techniques are disclosed by, for example, Sheridan and Venkataraghavan, *Acc. Chem Res.*, vol. 20, p. 322, 1987: Goodford, *J. Med. Chem.*, vol. 27, p. 557, 1984; Beddell, *Chem. Soc. Reviews*, vol. 279, 1985; Hol, *Angew. Chem.*, vol. 25, p. 767, 1986; and Verlinde and Hol, *Structure*, vol. 2, p. 577, 1994, each of which are incorporated by this reference herein in their entirety.

One embodiment of the present invention for structure based drug design comprises identifying a chemical compound that complements the shape of an FcR protein or a structure that is related to an FcR protein. Such method is referred to herein as a "geometric approach". In a geometric approach of the present invention, the number of internal degrees of freedom (and the corresponding local minima in the molecular conformation space) is reduced by considering only the geometric (hard-sphere) interactions of two rigid bodies, where one body (the active site) contains "pockets" or "grooves" that form binding sites for the second body (the complementing molecule, such as a ligand).

The geometric approach is described by Kuntz et al., *J. Mol. Biol.*, vol. 161, p. 269, 1982, which is incorporated by this reference herein in its entirety. The algorithm for chemical compound design can be implemented using the software program DOCK Package, Version 1.0 (available from the Regents of the University of California). Pursuant to the Kuntz algorithm, the shape of the cavity or groove on the surface of a structure (e.g., Fc.RIIa protein) at a binding site or interface is defined as a series of overlapping spheres of different radii. One or more extant databases of crystallographic data (e.g., the Cambridge Structural Database System maintained by University Chemical Laboratory, Cambridge University, Lensfield Road, Cambridge CB2 1EW, U.K.) or the Protein Data Bank maintained by Brookhaven National Laboratory, is then searched for chemical compounds that approximate the shape thus defined.

Chemical compounds identified by the geometric approach can be modified to satisfy criteria associated with chemical complementarity, such as hydrogen bonding, ionic interactions or Van der Waals interactions.

Another embodiment of the present invention for structure based drug design comprises determining the interaction of chemical groups ("probes") with an active site at sample positions within and around a binding site or interface, resulting in an array of energy values from which three dimensional contour surfaces at selected energy levels can be generated. This method is referred to herein as a "chemical-probe approach." The chemical-probe approach to the design of a chemical compound of the present invention is described by, for example, Goodford, *J. Med. Chem.*, vol. 28, p. 849, 1985, which is incorporated by this reference herein in its entirety, and is implemented using an appropriate software package, including for example, GRID (available from Molecular Discovery Ltd., Oxford OX2 9LL, U.K.). The chemical prerequisites for a site-complementing molecule can be identified at the outset, by probing the active site of an Fc.RIIa protein, for example, (as represented by the atomic coordinates shown in Table 1) with different chemical probes, e.g., water, a methyl group, an amine nitrogen, a carboxyloxygen and/or a hydroxyl. Preferred sites for interaction between an active site and a probe are determined. Putative complementary chemical compounds can be generated using the resulting three dimensional pattern of such sites.

A therapeutic composition of the present invention can comprise one or more therapeutic compounds of the present invention. A therapeutic composition can further comprise other compounds capable of reducing Ig-mediated responses or increasing a humoral immune response. For example, a therapeutic composition of the present invention useful for reducing tissue damage can also include compounds that block recruitment of inflammatory cells, such as by, for example, blocking complement fixation, extravasation, block binding of viral proteins to FcR, block opsinization or enhance normal and passive antibody immunity. A therapeutic composition of the present invention useful for reducing Ig-mediated inflammation can include compounds that block recruitment of inflammatory cells and/or block signal transduction pathway which leads to the release of inflammatory mediators.

A therapeutic composition of the present invention useful for increasing a humoral response can also include compounds that increase antibody production against an antigen (i.e., adjuvants), including, but not limited to, cytokines, chemokines, and compounds that induce the production of cytokines and chemokines (e.g., granulocyte macrophage colony stimulating factor (GM-CSF), granulocyte colony stimulating factor (G-CSF), macrophage colony stimulating factor (M-CSF), colony stimulating factor (CSF), erythropoietin (EPO), interleukin 2 (IL-2), interleukin-3 (IL-3), interleukin 4 (IL-4), interleukin 5 (IL-5), interleukin 6 (IL-6), interleukin 7 (IL-7), interleukin 8 (IL-8), interleukin 10 (IL-10), interleukin 12 (IL-12), interferon gamma, interferon gamma inducing factor I (IGIF), transforming growth factor beta, RANTES (regulated upon activation, normal T cell expressed and presumably secreted), macrophage inflammatory proteins (e.g., MIP-1 alpha and MIP-1 beta), bacterial components (e.g., endotoxins, in particular superantigens, exotoxins and cell wall components); aluminum-based salts; calcium-based salts; silica; polynucleotides; toxoids; serum proteins, viral coat proteins; block copolymer adjuvants (e.g., Hunter's Titermaxm adjuvant (Vaxcel™, Inc. Norcross, Ga.), Ribi adjuvants (Ribi ImmunoChem Research, Inc., Hamilton, Mont.); and saponins and their derivatives (e.g., Quil A (Superfos Biosector A/S, Denmark).

A therapeutic composition of the present invention can be used to treat disease in an animal by administering such composition to an animal in such a manner that desired therapeutic results are obtained. Preferred animals to treat include mammals, marsupials, reptiles and birds, with humans, companion animals, food animals, zoo animals and other economically relevant animals (e.g., race horses and animals valued for their coats, such as chinchillas and minks). More preferred animals to treat include humans, dogs, cats, horses, cattle, sheep, swine, chickens, ostriches, emus, turkeys, koalas and kangaroos. Particularly preferred animals to protect are humans, dogs and cats.

A preferred therapeutic composition of the present invention also includes an excipient, an adjuvant and/or carrier. Suitable excipients include compounds that the animal to be treated can tolerate. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, a therapeutic composition can include a carrier. Carriers include compounds that increase the half-life of a therapeutic composition in the treated animal. Suitable carriers include, but are not limited to, polymeric controlled release vehicles, biodegradable implants, liposomes, bacteria, viruses, other cells, oils, esters, and glycols.

Acceptable protocols to administer therapeutic compositions of the present invention in an effective manner include individual dose size, number of doses, frequency of dose administration, and mode of administration. Determination of such protocols can be accomplished by those skilled in the art. Modes of administration can include, but are not limited to, subcutaneous, intradermal, intravenous, intranasal, oral, transdermal, intraocular and intramuscular routes.

Another embodiment of the present invention are diagnostic compounds capable of detecting altered FcR protein on or isolated from cells obtained from patients having abnormal immunity or inflammation. Using the methods of structure based drug design described herein, diagnostic reagents that bind to FcR protein can be developed using the three dimensional structure of FcR protein. Preferred diagnostic reagents of the present invention include molecules capable of binding to the Ig binding site of an FcR protein capable of binding to Ig and molecules capable of binding to circulating FcR protein obtained from patients with inflammation. Preferred diagnostic reagents include molecules that are immunogenic or can be chemically coupled to detectable compounds, such as radioisotopes, enzymes, dyes or biotin.

In a preferred embodiment, a therapeutic compound or diagnostic compound of the present invention comprises a protein engineered by recombinant DNA methods.

Lengthy table referenced here

US07553809-20090630-T00001

Please refer to the end of the specification for access instructions.

Lengthy table referenced here

US07553809-20090630-T00002

Please refer to the end of the specification for access instructions.

Lengthy table referenced here

US07553809-20090630-T00003

Please refer to the end of the specification for access instructions.

Lengthy table referenced here

US07553809-20090630-T00004

Please refer to the end of the specification for access instructions.

Lengthy table referenced here

US07553809-20090630-T00005

Please refer to the end of the specification for access instructions.

The present invention provides a variety of compounds which can modulate the interaction between Fc receptors and immunoglobulins. Without being bound by any theory, it is believed that particularly useful compounds target the region C (see FIG. 19) of Fc receptors, e.g., FcγRII. Thus, it is believed that these compounds interfere with the dimerization interface between two FcγRII proteins, thereby affecting cellular signal transduction through one or both of the FcR proteins. Specifically, it is believed that peptide residues 117-131 and 150-164 of FcγRII make up the interfacial area of the FcγIIa dimer, and compounds which can mimic or bind to these regions are believed to be good binding modulators. For example, native hexapeptide Phe121 to Ser126 or shorter segments span a region with significant hydrogen bonding interaction and therefore, are suitable modulators of dimerization between two FcγRIIa molecules.

The compounds of the present invention are derived from a random screening as well as a rational drug design to modulate Fc receptors. FcγR are expressed on most hematopoietic cells, and through the binding of IgG play a key role in homeostasis of the immune system and host protection against infection. FcγRII is a low affinity receptor for IgG that essentially binds only to IgG immune complexes and is expressed on a variety of cell types including, for example monocytes, macrophages, neutrophils, eosinophils, platelets and B lymphocytes. FcγRII is involved in various immune and inflammatory responses including antibody-dependent cell-mediated cytotoxicity, clearance of immune complexes, release of inflammatory mediators and regulation of antibody production.

The binding of IgG to a FcγR can lead to disease indications that involve regulation by FcγR. For example, the autoimmune disease thrombocytopenia purpura involves tissue (platelet) damage resulting from FcγR-dependent IgG immune complex activation of platelets or their destruction by FcγR+ phagocytes. In addition, various inflammatory diseases are known to involve IgG immune complexes (e.g. rheumatoid arthritis, systemic lupus erythematosus), including type II and type III hypersensitivity reactions. Type II and type III hypersensitivity reactions are mediated by IgG, which can activate either complement-mediated or phagocytic effector mechanisms, leading to tissue damage.

Knowledge of the three dimensional structure of FcγRIIa or indeed any FcR can facilitate the formulation of therapeutic and diagnostic reagents for disease management. For example, by knowing the structure of a binding region of FcγRIIa, one can design compounds that can modulate the binding of immunoglobulins to FcγRIIa. The structure of a number of Fc receptors, including FcγRIIa, FcεRI and FcγRIIIb, are disclosed in provisional U.S. patent application Ser. No. 60/073,972, filed Feb. 6, 1998, which is incorporated by reference herein in its entirety, and the above mentioned U.S. patent application Ser. No. 09/245,764, filed Feb. 5, 1999, entitled "3 Dimensional Structure and Models of Fc Receptors and Uses Thereof."

Figure 19:
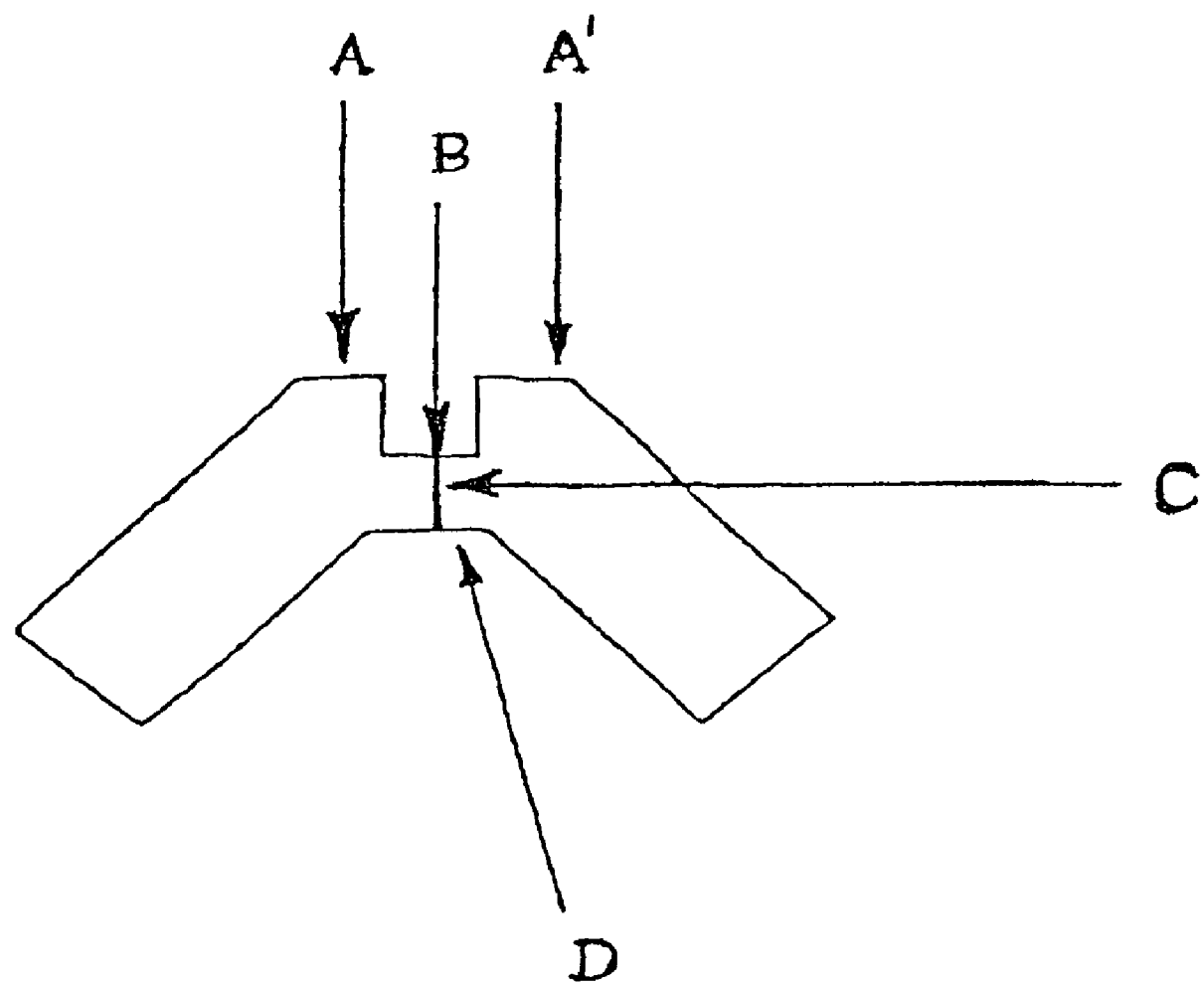

FcγRIIa is a protein dimer and has a C2 axis of symmetry. A schematic structure of the binding region of FcγRIIa based on the X-ray crystal structure is shown in FIG. 19. Without being bound by any theory, it is believed that sites A and A' are believed to be the Fc-antibody interface regions; therefore, a compound which binds to or impinges on sites A or A' is likely to interfere with the normal binding of this receptor to IgG. In addition, a compound that binds to sites B, C and/or D may interfere with or facilitate antibody binding if the compound alters the structure of the receptor so as to destabilize antibody binding or encourage dimerization of the receptors, respectively.

Figure 20:
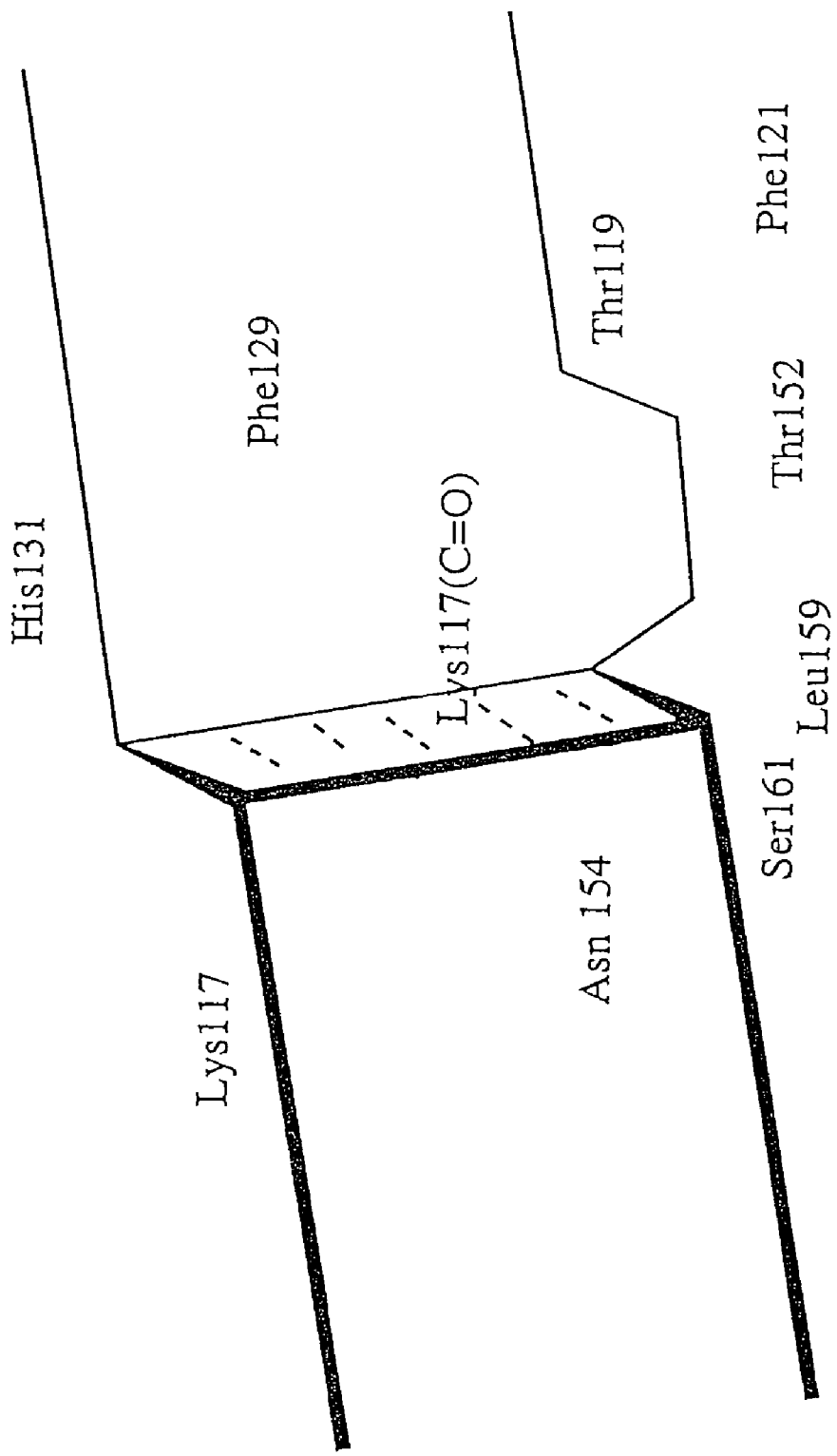

FIG. 20 shows a lateral schematic view of site B, i.e., the groove, illustrating only one face, with the protein residues of interest in modulator design. The lip of the groove contains lysine and histidine residues and represents a target for interaction with hydrogen-bonding and/or acidic groups in a suitable modulator. The wall of the groove contains a phenylalanine benzene ring and may be a target for a hydrophobic interaction, particularly π-π interactions. The "floor" of the groove includes Phe121, Thr152, Leu159 and Ser161 and together with Asn154, Lys117 (backbone carbonyl) and Thr119. These proteins are believed to be arranged to form a pocket that is capable of strong hydrogen bonding and/or Van der Waals interactions with a modulator or a ligand.

Figure 21:
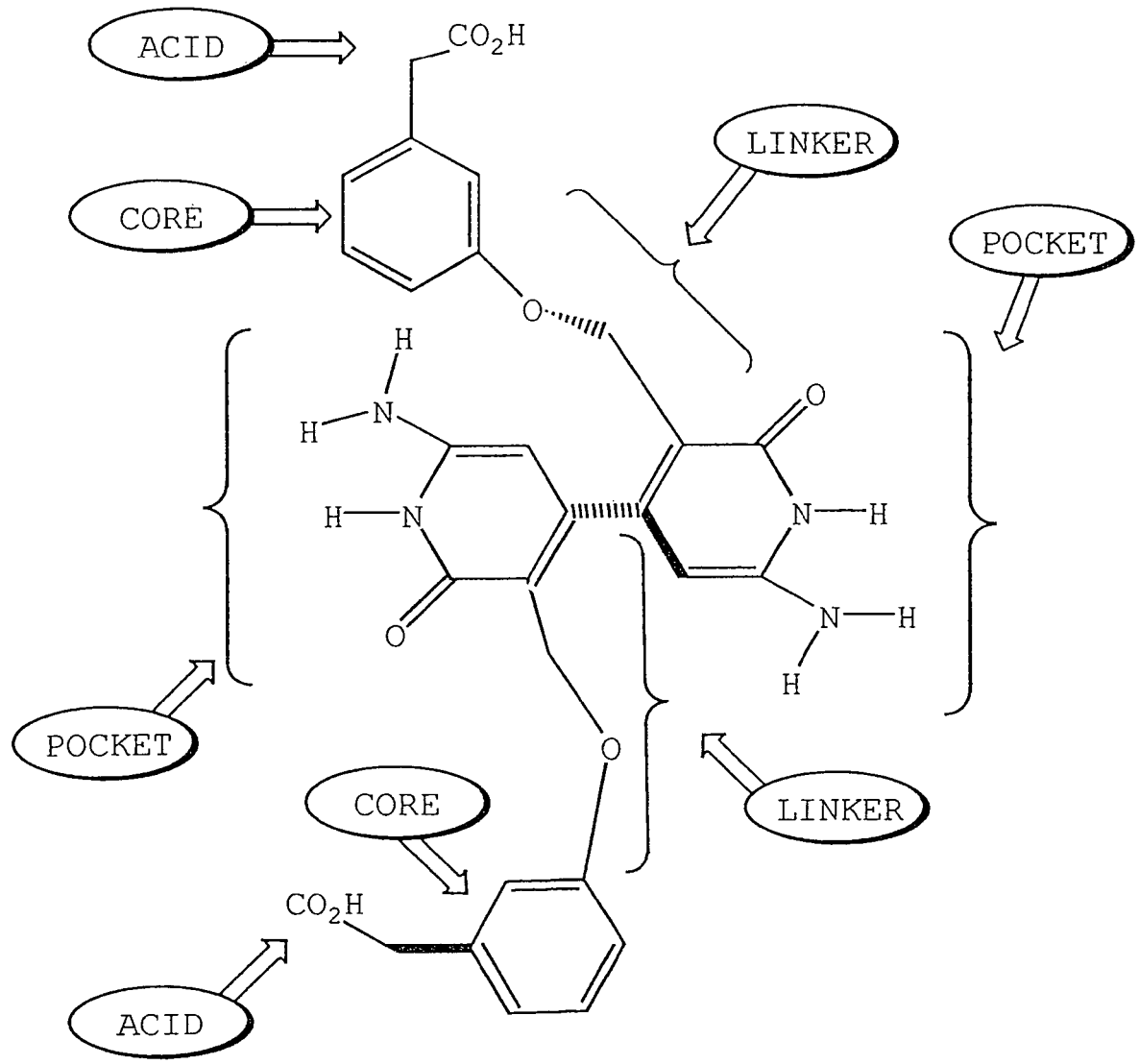
Figure 22:
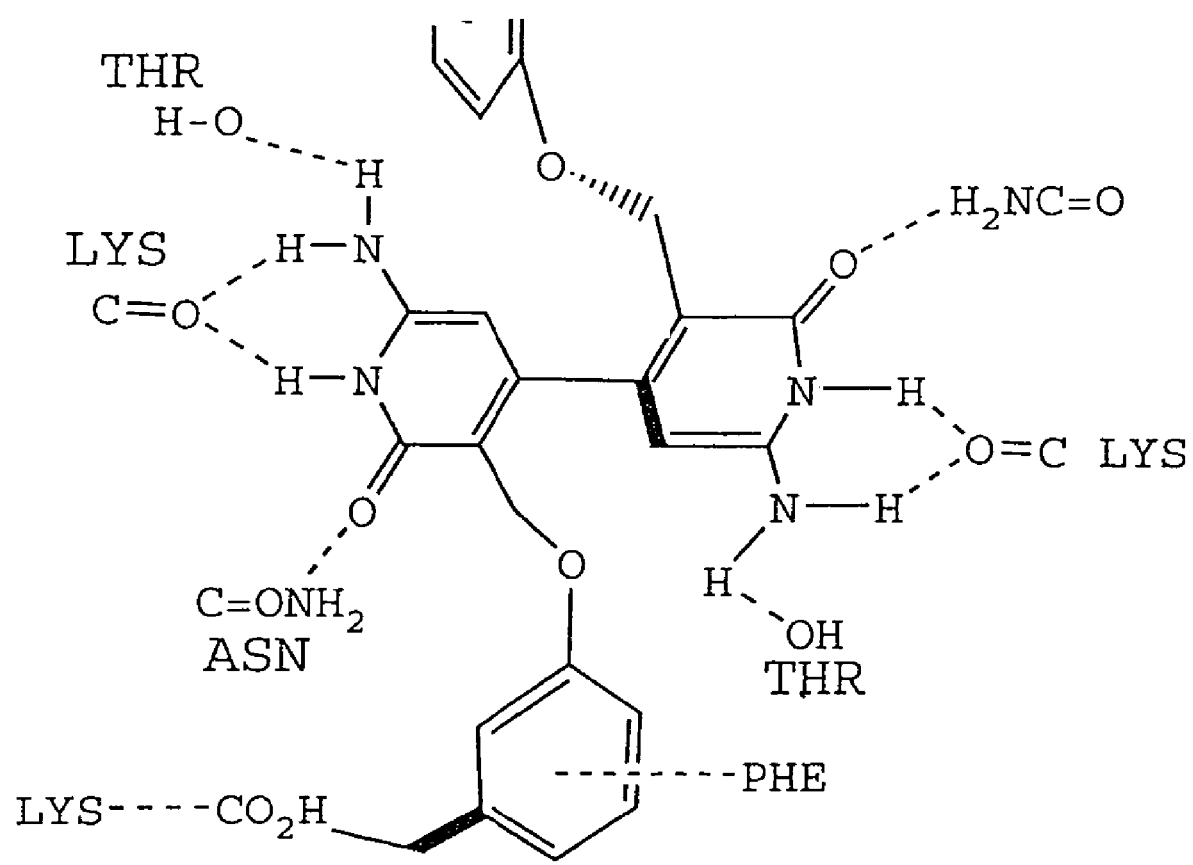

The features of the groove detailed above have lead to the design and synthesis of compounds depicted generally as:

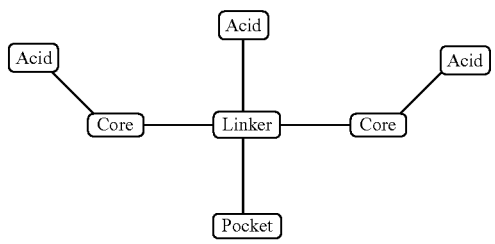

where the "core" is a lipophilic group, such as an aromatic ring, and "linker" represents connectivity of from 1 to about 20 atoms, preferably from 1 to about 10 atoms, and more preferably from 2 to about 8 atoms. The presence of the acid and the pocket groups which are directly linked to the linker group is optional. In order to interact favorably with the basic groups, e.g., Lys117 and His131, at the lip of the groove, acidic groups ("acid") can be branched from the "core" and/or the "linker". "Pocket" represents that portion of the molecule which fills the pockets at the floor of the groove. Alternatively, the modulator can bind or occupy only the pocket of the receptor. These principles are specifically exemplified in FIG. 21 which depicts how a particular modulator relates to the general design illustrated above and in FIG. 22 which illustrates the points of interaction between this modulator and the Fc□RIIa protein.

An exemplary compound containing a "pocket" residue is shown in FIG. 23, where a cytosine-like ring moiety is present in the linker portion of the compound. Other suitable pocket binders include nucleic acids and related structures such as hydrazides and amidoureas as shown below or their derivative.

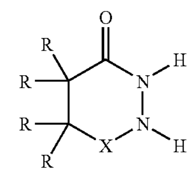

hydrazides 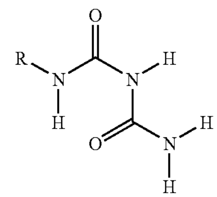 amidoureas

X is C═O or $CH_2$

Preferably, these pocket residues consist of a dimer of a compound, e.g., a dimer of nucleic acids, hydrazides, amidoureas or their derivatives.

Compounds of the present invention which have the above described general features include an aromatic compound of the formula:

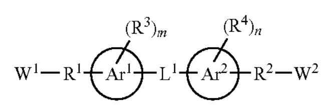

a heteroaromatic compound of the formula:

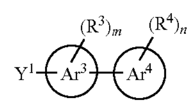

a cyclic compound of the formula:

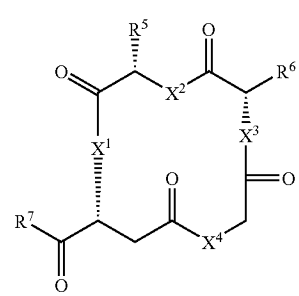

a bicyclic compound of the formula:

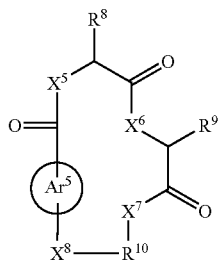

and an amino acid derivative of the formula:

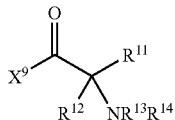

or salts thereof, where each of $W^1$ and $W^2$ is independently $CO_2R^{15}$, $C(=NH)NH(OH)$, $SO_3R^{15}$, $C(=NH)NH_2$, $OPO(OR^{15})_2$, $C(=O)CF_3$ or $PO(OR^{15})_2$; each of $Ar^1$, $Ar^2$, $Ar^4$ and $Ar^5$ is independently $C_6$-$C_{20}$ aryl or $C_1$-$C_{20}$ heteroaryl; $Ar^3$ is $C_1$-$C_{20}$ heteroaryl; each of $X^1$, $X^2$, $X^3$, $X^4$, $X^5$, $X^6$, $X^7$ and $X^8$ is independently methylene, O, S or $NR^{16}$; each of $R^1$ and $R^2$ is independently a bond, $C_1$-$C_6$ alkylene, or halogenated $C_1$-$C_6$ alkylene; each of $R^3$ and $R^4$ are independently halogen, $-Z^1$ or $C_1$-$C_6$ alkyl; each of $X^9$, $Y^1$ and $Z^1$ is independently $OR^1$, $SR^{17}$ or $NR^{17}R^{18}$, each of $R^5$ and $R^6$ is independently amino acid side chain residue or a moiety of the formula $-R^{19}-W^3$; each of $R^8$, $R^9$ and $R^{11}$ is independently an amino acid side chain residue, provided $R^{11}$ is not H or $CH_3$; $R^7$ is $OR^{20}$, $NR^{21}R^{22}$, or from about 1 to about 10 amino acids; $R^{10}$ is $C_1$-$C_6$ alkylene; R is $C_1$-$C_6$ alkyl or $C_6$-$C_{20}$ aralkyl; $W^3$ is $C(=O)X^{10}$; $X^{10}$ is $OR^{23}$ or $NR^{24}R^{25}$; each of $R^{13}$, $R^{15}$, $R^{16}$, $R^{18}$, $R^{20}$, $R^{21}$, $R^{23}$ and $R^{24}$ is independently hydrogen or $C_1$-$C_6$ alkyl; each $R^{16}$ is independently H, $C_6$-$C_{20}$ aryl or an amide protecting group; $R^{19}$ is $C_1$-$C_6$ alkylene; each of $R^{22}$ and $R^{25}$ is independently H, $C_1$-$C_6$ alkyl or an amide protecting group; $R^{14}$ is H, $C_1$-$C_6$ alkyl or an amine protecting group; L is a linker comprising from 1 to about 20 atoms; and each of m and n is independently an integer from 0 to 2.

"Alkyl" groups according to the present invention are aliphatic hydrocarbons which can be straight or branched chain groups. Alkyl groups optionally can be substituted with one or more substituents, such as a halogen, alkenyl, alkynyl, aryl, hydroxy, amino, thio, alkoxy, carboxy, oxo or cycloalkyl. There may be optionally inserted along the alkyl group one or more oxygen, sulfur or substituted or unsubstituted nitrogen atoms. Exemplary alkyl groups include methyl, ethyl, i-propyl, n-butyl, t-butyl, fluoromethyl, difluoromethyl, trifluoromethyl, chloromethyl, trichloromethyl, methoxy ethyl, aminomethyl, and pentafluoroethyl.

"Aryl" groups are monocyclic or bicyclic carbocyclic or heterocyclic aromatic ring moieties. Aryl groups can be substituted with one or more substituents, such as a halogen, alkenyl, alkyl, alkynyl, hydroxy, amino, thio, alkoxy or cycloalkyl.

"Mono-aryl or heteroaryl" refers to a monocyclic carbocyclic or heterocyclic aromatic ring. Exemplary mono-aryl or heteroaryl rings include pyrrole, thiophene, furan, imidazole, pyrazole, 1,2,4-triazole, pyridine, pyrazine, pyrimidine, pyridazine, thiazole, isothiazole, oxazole, isoxazole, s-triazine and benzene. Preferred group is phenyl.

"Di-aryl or heteroaryl" means a bicyclic ring system composed of two fused carbocyclic and/or heterocyclic aromatic rings. Exemplary di-aryl or heteroaryl rings include indene, isoindene, benzofuran, dihydrobenzofuran, benzothiophene, indole, 1H-indazole, indoline, azulene, tetrahydroazulene, benzopyrazole, benzoxazole, benzoimidazole, benzothiazole, 1,3-benzodioxole, 1,4-benzodioxan, purine, naphthalene, tetralin, coumarin, chromone, chromene, 1,2-dihydrobenzothiopyran, tetrahydrobenzothiopyran, quinoline, isoquinoline, quinazoline, pyrido[3,4-b]-pyridine, and 1,4-benisoxazine.

"Aralkyl" refers to an alkyl group substituted with an aryl group. Suitable aralkyl groups include, without limitation, benzyl, 2-phenylethyl and picolyl. Aryl groups may also be substituted with other suitable functional groups. Aralkyl groups include those with heterocyclic and carbocyclic aromatic moieties.

A "linker" ($L^1$) refers to a chain of atoms which links $Ar^1$ to $Ar^2$ with the number of atoms as specified. The number associated with the linker refers to only the number of atoms which directly link $Ar^1$ and $Ar^2$. The $L^1$ moiety can contain groups that can participate in hydrogen bonding and/or Van der Waals interactions with amino acid residues in the groove of the receptor, for example, trifluoroacetyl, imide, urea, amidine, amidoxime or their derivatives.

An "amino acid sidechain residue" refers to an amino acid side chain which is found on the α-carbon of an α-amino acids of naturally occurring and commercially available amino acids. Typical amino acid sidechain residues include hydrogen (glycine), methyl (alanine), $—CH_2CH_2CH_2NHC(=NH)NH_2$ (arginine), $—CH_2C(=O)NH_2$ (asparagine), $—CH_2CO_2H$ (aspartic acid), $—CH_2SH$ (cysteine), $—CH_2CH_2C(=O)NH_2$ (glutamine), $—CH_2CH_2CO_2H$ (glutamic acid), $—CH_2—$(4-imidazole) (histidine), $—CH(Et)CH_3$ (isoleucine), $—CH_2CH(CH_3)$ (leucine), $—(CH_2)_4NH_2$ (lysine), $—(CH_2)_2SCH_3$ (methionine), $—CH_2Ph$ (phenylalanine), $—CH_2—CH_2—CH_2—$ (proline), $—CH_2OH$ (serine), $—CH(OH)CH_3$ (threonine), $—CH_2$-(3-indole) (tryptophan), $—CH_2$-(4-hydroxyphenyl) (tyrosine) and $—CH(CH_3)_2$ (valine) The pKa of corresponding acid group of $W^1$ and $W^2$ are less than about 9, more preferably less than about 7 and most preferably less than about 5. The "corresponding acid group of $W_1$, and $W_2$" refers to the parent acid group of $W^1$ and $W^2$, for example, when $W^1$ and $W^2$ are esters the corresponding acid refers to the carboxylic acid, and when $W^1$ and $W^2$ are alkyl phosphonates the corresponding acid refers to the phosphonic acid. It will be appreciated that the pKa of $W^1$ and $W^2$ depends not only on the identity of $W^1$ and $W^2$ but also on the type of substituents present near the $W^1$ and $W^2$ groups and/or in the mono- or di-aryl or heteroaryl group to which $W^1$ and $W^2$ are attached. Thus, for example, a presence of one or more electron withdrawing groups such as nitro, nitroso, carbonyl, cyano and halogen groups reduces the pKa of the corresponding $W^1$ and $W^2$ acid group. The pKa is defined as -log(Ka) where Ka is a dissociation constant. The strength of an acid or base in a given medium is indicated by the value of its dissociation constant. For example, strong bases are strong proton acceptors (or an electron-pair donor) and have high pKa values. pKa values depend on a variety of factors such as solvent and temperature. For example, water ($H_2O$), not the conjugate acid of water which is $H_3O+$, has pKa of 15.7 at 25° C. in water, 16.7 at 0° C., and 14.7 at 60° C. In addition, its pKa is 27.5 in dimethyl sulfoxide (DMSO)

at 25° C. The pKa values in the present application refer to the pKa values relative to pKa value of water at about 15.7, unless otherwise stated.

With reference to the formulas described herein:

Preferably, $W^1$ and $W^2$ are independently $CO_2R^5$, $C(=NH)NH(OH)$ $OPO(OR^5)_2$, $C(=O)CF_3$ or $PO(OR^5)_2$.

Preferably, $R^1$ and $R^2$ are independently a bond, $C_1$-$C_6$ alkylene or fluorinated $C_1$-$C_6$ alkylene. More preferably, $R^1$ and $R^2$ are independently a bond, methylene or difluoromethylene.

Preferably, each of $Ar^1$, $Ar^2$ and $Ar^5$ are independently mono-aryl or heteroaryl. More preferably $Ar^1$, $Ar^2$ and $Ar^5$ are phenyl.

Preferably, $Ar^3$ is 2-pyridonyl, and more preferably $Ar^3$ is 4-$Ar^4$-(2-pyridonyl), i.e., the 4-position of the 2-pyridone moiety is attached to the $Ar^4$ moiety.

Preferably, $Ar^4$ is $C_1$-$C_{20}$ heteroaryl. More preferably, $Ar^4$ is pyridyl. Most preferably $Ar^4$ is 4-pyridyl, i.e., the 4-position of the pyridine moiety is attached to the $Ar^3$ moiety.

Preferably, $Y^1$ is $NR^{17}R^{18}$. More preferably, $Y^1$ is $NH_2$.

Preferably, each $R^{15}$ is independently hydrogen, methyl or ethyl.

Preferably, $L^1$ is $C_1$-$C_6$ alkylene; $C_1$-$C_6$ alkenylene, including αβ-unsaturated carbonyl moieties (e.g., —CH=CH—C(=O)—); or a moiety of the formula —$R^{33}$—$X^{14}$—, —$R^{34}$—$X^{15}$—$R^{35}$— or —$X^{16}$—$R^{36}$—$Ar^6$—$Ar^7$—$R^{37}$—$X^{17}$—. Each of $R^{33}$, $R^{34}$, $R^{35}$, $R^{36}$ and $R^{37}$ is independently $C_1$-$C_6$ alkylene (including a substituted alkylene), preferably methylene. Each of $X^{14}$, $X^{15}$, $X^{16}$ and $X^{17}$ is independently O, S or $NR^{38}$, preferably O or $NR^{38}$. Each of $Ar^6$ and $Ar^7$ is independently $C_6$-$C_{20}$ aryl or $C_1$-$C_{20}$ heteroaryl, preferably 2-pyridone. And $R^{38}$ is H, $C_1$-$C_6$ alkyl or an amine protecting group, preferably —$CH_2CO_2H$.

More preferably, $L^1$ is sulfonamide (—$SO_2NH$—), ethylene (—$CH_2CH_2$—), —$CH_2O$—, —CH=CHC(=O)—, —$CH_2CH_2CH(OH)$—, —CH=CH—, —CH(OH)CH(OH)—, —$CH_2N(R^{38})CH_2$—, a moiety of the formula:

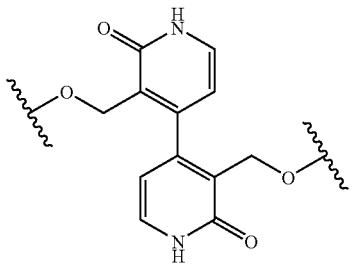

or a moiety of the formula:

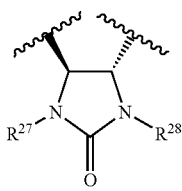

where each of $R^{27}$ and $R^{28}$ is independently H, $C_1$-$C_6$ alkyl, $C_6$-$C_{10}$ aralkyl or a protecting group. Preferably $R^{27}$ and $R^{28}$ are independently H or a protecting group. More preferably, $R^{27}$ and $R^{28}$ are independently H or 4-methoxybenzyl.

Preferably m and n are 0.

Alternatively, $R^1$ and $W^1$ and/or $R^2$ and $W^2$ together form —$(CH_2)_aCH(NHR^{29})CO_2R^{39}$ and —$(CH_2)_bCH(NHR^{30})CO_2R^{40}$, respectively, where a and b are independently an integer from 0 to 2, $R^{29}$ and $R^{30}$ are independently H or an amine protecting group, and $R^{39}$ and $R^{40}$ are independently H or $C_1$-$C_6$ alkyl. Preferably, a and b are 1. Preferably, $R^{29}$ and $R^{30}$ are independently H, $C_1$-$C_6$ alkyl or an amine protecting group.

Preferably, $R^5$ is asparagine sidechain residue.

Preferably, $R^6$ is glutamine sidechain residue.

Preferably, $R^7$ is from about 1 to about 10 amino acids or derivatives thereof, more preferably from about 1 to about 5 amino acids or derivatives thereof, still more preferably at least about 2 amino acid residues or derivatives thereof, and most preferably -lys-ser-$CONHCH_3$ moiety, i.e., a moiety of the formula —$NHCH[(CH_2)_4NH_2]CONHCH(CH_2OH)CONHCH_3$.

Preferably, $X^1$, $X^2$, $X^3$, $X^4$, $X^5$, $X^6$, $X^7$ and $X^8$ are independently O or $NR^{16}$. More preferably, $X^1$, $X^2$, $X^3$, $X^4$, $X^5$, $X^6$, $X^7$ and $X^8$ are $NR^{16}$.

Preferably, $X^9$ is $OR^{17}$ or $NR^{17}R^{18}$, more preferably $NR^{17}R^{18}$, and most preferably $NH_2$.

Preferably, $R^8$ is glycine sidechain residue (i.e., H).

Preferably, $R^9$ is tyrosine sidechain residue (i.e., 4-hydroxybenzyl).

Preferably, $R^{10}$ is propylene.

Preferably, $R^{11}$ is lysine side chain residue, i.e., a moiety of the formula —$(CH_2)_4NH_2$.

Preferably $R^{12}$ is $C_6$-$C_{20}$ aralkyl, and more preferably 2-phenylethyl.

Preferably $R^{13}$ is H.

Preferably $R^{14}$ is H or an amine protecting group, more preferably an amine protecting group, and most preferably an acetyl group, i.e., a moiety of the formula —C(=O)$CH_3$.

Preferably, each $R^{16}$ is independently H or $C_6$-$C_{20}$ aryl. More preferably each $R^{16}$ is independently H or phenyl.

In one particular embodiment of the present invention, the aromatic compound described above is of the formula:

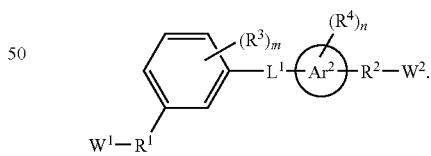

More preferably, the aromatic compound is of the formula:

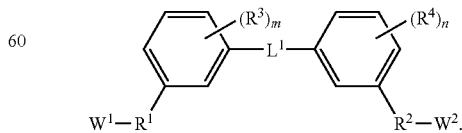

In another particular embodiment of the present invention, the aromatic compound described above is of the formula:

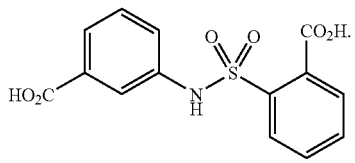

In one particular embodiment of the present invention, the heteroaromatic compound described above is of the formula:

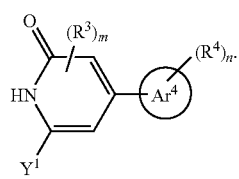

More preferably, the heteroaromatic compound described above is of the formula:

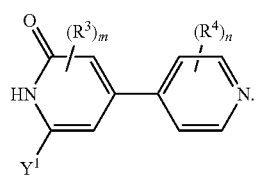

In another particular embodiment of the present invention, the cyclic compound described above is of the formula:

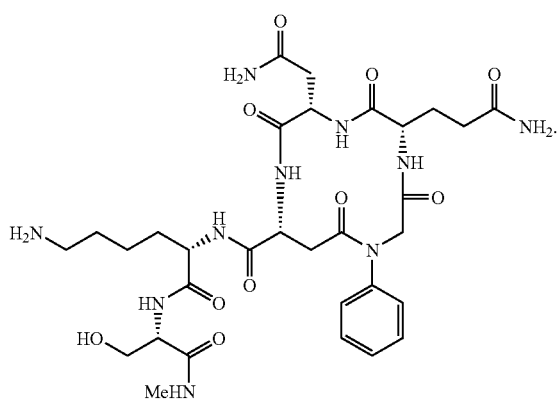

In still another particular embodiment of the present invention, the bicyclic compound described above is of the formula:

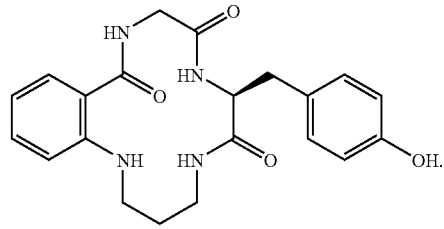

In yet another particular embodiment of the present invention, the amino acid derivative described above is of the formula:

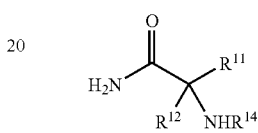

or its salt thereof. Preferably, the amino acid derivative described above is of the formula:

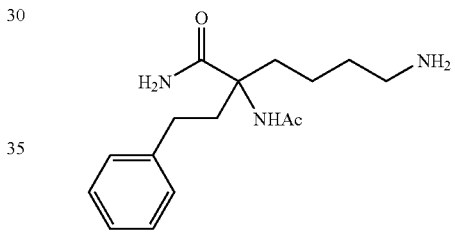

or its salt thereof.

The Fc receptor modulating compounds of the present invention can also include nucleosides or derivatives thereof. Preferably, the nucleosides of the present invention have the formula:

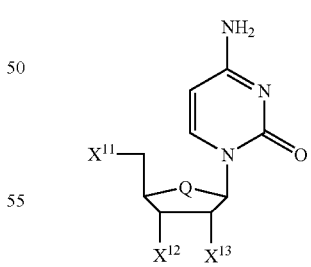

where Q is O or methylene. Preferably, Q is O. $X^{11}$ is $OR^{31}$ or $OPO(OR^{31})_2$. Preferably $X^{11}$ is OH or $OPO_3H_2$. Each of $X^{12}$ and $X^{13}$ is independently H or $OR^{15}$. Preferably, each of $X^{12}$ and $X^{13}$ is independently H or OH. Each of $R^{31}$ and $R^{32}$ is independently H or $C_1$-$C_6$ alkyl.

The Fc receptor modulating compounds of the present invention can further include folic acid or its derivatives.

Figure 29:
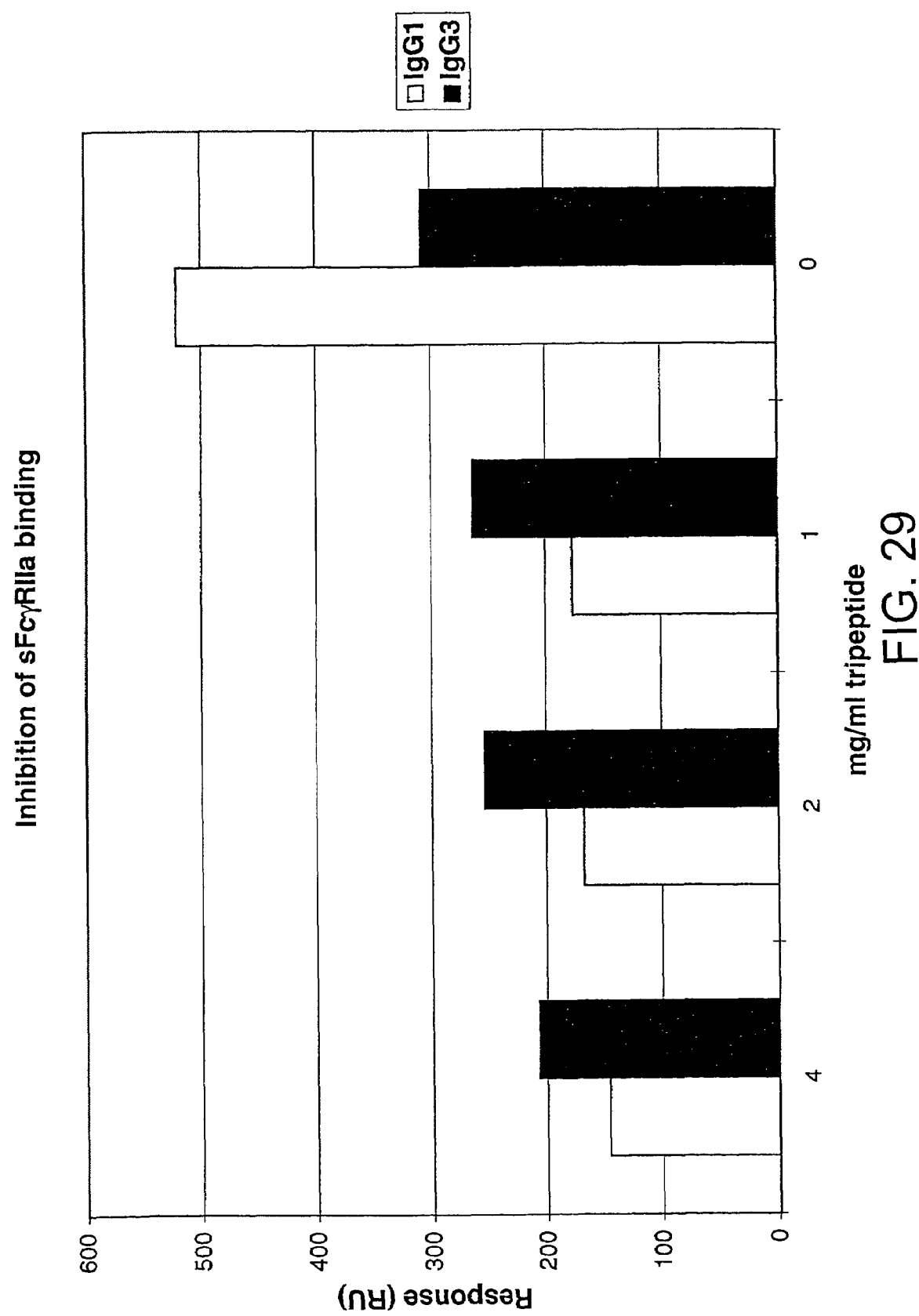

The Fc receptor modulating compounds of the present invention can also include peptides which can modulate the interaction between Fc receptors and immunoglobulins. Without being bound by any theory, it is believed that particularly useful peptides target the region C (see FIG. 19) of Fc receptors, e.g., FcγRII. Thus, it is believed that these peptides interfere with the dimerization interface between two FcγRII proteins, thereby affecting cellular signal transduction through one or both of the FcR proteins. Specifically, residues 117-131 and residues 150-164 make up the interfacial area of the FcγIIa dimer, and peptides from these sequences or their mimics are binding inhibitors. For example, native hexapeptide Phe121 to Ser126 or shorter segments spans a region with significant hydrogen bonding interaction and therefore, is a suitable modulator of dimerization between two FcγRIIa molecules. Such a protein segment is disclosed as part of SEQ ID No. 3 in the above mentioned U.S. patent application Ser. No. 09/245,764, now U.S. Pat. No. 6,675,105 filed Feb. 5, 1999, entitled "3 Dimensional Structure and Models of Fc Receptors and Uses Thereof." Thus, the present inventors have discovered that a tripeptide of sequence GKS (gly-lys-ser) or its derivatives and hexapeptides of sequence FQNGKS (phe-gln-asn-gly-lys-ser) (SEQ ID NO:16) or derivatives thereof modulate binding of FcγRII to IgG. See Example 24 and FIGS. 29 and 30.

The present inventors have also found that conformationally constrained macrocyclic compounds modulate FcR protein activities. As used herein a "macrocyclic compound" refers to a compound containing a ring moiety which is comprised of from about 8 atoms to about 18 atoms. Preferably, the ring structure of the macrocyclic compound of the present invention comprises from about 10 to about 16 atoms, more preferably from about 12 to about 14 atoms, and most preferably from about 13 to about 14 atoms. A particularly useful macrocyclic compound of the present invention is a cyclic peptide or derivatives thereof. Such cyclic peptide having the formula:

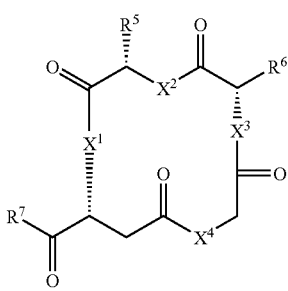

is described above.

The top of the FG loop of FcR has been shown by mutagenesis studies to be important in Ig binding. The FG peptide strand contains an extended β-sheet which projects the amino acid sidechains in the FG loop in a defined orientation. Such Fc protein orientation is described in the above mentioned U.S. patent application Ser. No. 09/245,764, filed Feb. 5, 1999, now U.S. Pat. No. 6,675,105 entitled "3 Dimensional Structure and Models of Fc Receptors and Uses Thereof." Molecules which can act as β-turn mimics so as to present its sidechains at the top of the FG loop in the same way as those in the receptor have also been found to be effective in modulating the FcR receptor activities. Thus, in another embodiment of the present invention, the Fc receptor modulating compound of the present invention also includes a compound of the formula:

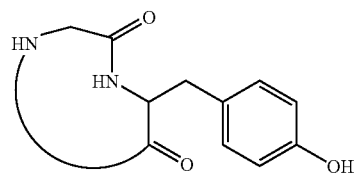

where the macrocyclic portion contains the same number of atoms as described above. One particular embodiment of such β-turn mimic is the compound described above having the formula:

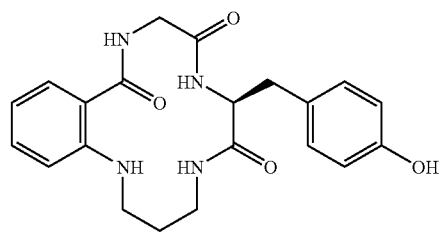

The compounds of the present invention can be synthesized from readily available starting materials. Various substituents on the compounds of the present invention can be present in the starting compounds, added to any one of the intermediates or added after formation of the final products by known methods of substitution or conversion reactions. If the substituents themselves are reactive, then the substituents can themselves be protected according to the techniques known in the art. A variety of protecting groups are known in the art, and can be employed. Examples of many of the possible groups can be found in "Protective Groups in Organic Synthesis" by T. W. Green, John Wiley and Sons, 1981, which is incorporated herein in its entirety. For example, nitro groups can be added by nitration and the nitro group can be converted to other groups, such as amino by reduction, and halogen by diazotization of the amino group and replacement of the diazo group with halogen. Acyl groups can be added by Friedel-Crafts acylation. The acyl groups can then be transformed to the corresponding alkyl groups by various methods, including the Wolff-Kishner reduction and Clemmenson reduction. Amino groups can be alkylated to form mono- and di-alkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product, including isolated products.

Since the compounds of the present invention can have certain substituents which are necessarily present, the introduction of each substituent is, of course, dependent on the specific substituents involved and the chemistry necessary for their formation. Thus, consideration of how one substituent would be affected by a chemical reaction when forming a second substituent would involve techniques familiar to one of ordinary skill in the art. This would further be dependent on the ring involved.

It is to be understood that the scope of this invention encompasses not only the various isomers which may exist but also the various mixtures of isomers which may be formed.

If the compound of the present invention contains one or more chiral centers, the compound can be synthesized enantioselectively or a mixture of enantiomers and/or diastereomers can be prepared and separated. The resolution of the compounds of the present invention, their starting materials and/or the intermediates may be carried out by known procedures, e.g., as described in the four volume compendium *Optical Resolution Procedures for Chemical Compounds*: Optical Resolution Information Center, Manhattan College, Riverdale, N.Y., and in *Enantiomers, Racemates and Resolutions*, Jean Jacques, Andre Collet and Samuel H. Wilen; John Wiley & Sons, Inc., New York, 1981, which are incorporated herein in their entirety. Basically, the resolution of the compounds is based on the differences in the physical properties of diastereomers by attachment, either chemically or enzymatically, of an enantiomerically pure moiety results in forms that are separable by fractional crystallization, distillation or chromatography.

When the compound of the present invention contains an olefin moiety and such olefin moiety can be either cis- or trans-configuration, the compound can be synthesized to produce cis- or trans-olefin, selectively, as the predominant product. Alternatively, the compound containing an olefin moiety can be produced as a mixture of cis- and trans-olefins and separated using known procedures, for example, by chromatography as described in W. K. Chan, et al., *J. Am. Chem. Soc.*, 1974, 96, 3642, which is incorporated herein in its entirety.

The compounds of the present invention form salts with acids when a basic amino function is present and salts with bases when an acid function, e.g., carboxylic acid or phosphonic acid, is present. All such salts are useful in the isolation and/or purification of the new products. Of particular value are the pharmaceutically acceptable salts with both acids and bases. Suitable acids include, for example, hydrochloric, oxalic, sulfuric, nitric, benzenesulfonic, toluenesulfonic, acetic, maleic, tartaric and the like which are pharmaceutically acceptable. Basic salts for pharmaceutical use include Na, K, Ca and Mg salts.

In addition to and/or instead of a rational drug design, other Fc receptor modulators can be identified by a screening process, where a variety of compounds are tested to determine their Fc receptor modulating activity. In this manner, a variety of Fc receptor modulators have been identified. Thus, compounds of the present invention include substituted and unsubstituted benzoic acids, in particular, 4-methyl benzoic acid and 3-methyl benzoic acid; nucleosides and analogs thereof; and folic acid and its derivatives.

The compounds of the present invention are Fc receptor modulators, e.g., they modulate Fc receptor binding of immunoglobulins. Preferably, the compounds of the present invention modulate Fc receptors selected from the group consisting of FcαR, FcεR, FcγR and mixtures thereof, more preferably from the group consisting of FcγRI, FcγRII, FcγRIII and mixtures thereof, still more preferably from the group consisting of FcγRIIa, FcγRIIb, FcγRIIc and mixtures thereof, and most preferably FcγRIIa receptor. The compounds of the present invention can be used in a variety of applications including treatment or diagnosis of any disease where aggregates of antibodies are produced and where immune complexes are produced by contact of antibody with intrinsic or extrinsic antigen. Exemplary treatments and diagnosis applicable by the compounds of the present invention include immune complex diseases; autoimmune diseases including but not limited to rheumatoid arthritis, systemic lupus erythematosus, immune thrombocytopenia, neutropenia, hemolytic anaemias; vasculitities including but not limited to polyarteritis nodosa, systemic vasculitis; xenograft rejection; and infectious diseases where FcR uptake of virus enhances infection including but not limited to flavivirus infections such as Dengue virus-dengue hemorrhagic fever and measles virus infection. The compound of the present invention can also be used to reduce IgG-mediated tissue damage and to reduce inflammation.

The compounds of the present invention can also enhance leukocyte function by enhancing FcR function. These functions include antibody dependent cell mediated cytotoxicity, phagocytosis, release of inflammatory cytokines. Exemplary treatments and diagnosis for enhanced FcR function include any infection where normal antibodies are produced to remove the pathogen; and any disease requiring FcR function where natural or recombinant antibodies can be used in treatment such as cancer and infections, for example, the antibody can be administered in combination with the compound of the present invention to enhance the effect of the antibody treatment.

The compounds of the present invention can be administered to a patient to achieve a desired physiological effect. Preferably the patient is an animal, more preferably a mammal, and most preferably a human. The compound can be administered in a variety of forms adapted to the chosen route of administration, i.e., orally or parenterally. Parenteral administration in this respect includes administration by the following routes: intravenous; intramuscular; subcutaneous; intraocular; intrasynovial; transepithelially including transdermal, ophthalmic, sublingual and buccal; topically including ophthalmic, dermal, ocular, rectal and nasal inhalation via insufflation and aerosol; intraperitoneal; and rectal systemic.

The active compound can be orally administered, for example, with an inert diluent or with an assimilable edible carrier, or it can be enclosed in hard or soft shell gelatin capsules, or it can be compressed into tablets, or it can be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparation can contain at least 0.1% of active compound. The percentage of the compositions and preparation can, of course, be varied and can conveniently be between about 1 to about 10% of the weight of the unit. The amount of active compound in such therapeutically useful compositions is such that a suitable dosage will be obtained. Preferred compositions or preparations according to the present invention are prepared such that an oral dosage unit form contains from about 1 to about 1000 mg of active compound.

The tablets, troches, pills, capsules and the like can also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin can be added or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar or both. A syrup or elixir can contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound can be incorporated into sustained-release preparations and formulation.

The active compound can also be administered parenterally. Solutions of the active compound as a free base or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It can be stable under the conditions of manufacture and storage and must be preserved against the contaminating action of microorganisms such as bacterial and fungi. The carrier can be a solvent of dispersion medium containing, for example, water, ethanol, polyol (e.g., glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, e.g., sugars or sodium chloride. Prolonged absorption of the injectable compositions of agents delaying absorption, e.g., aluminum monostearate and gelatin.

Sterile injectable solutions are prepared by incorporating the active compound in the required amount in the appropriate solvent with various other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

The therapeutic compounds of the present invention can be administered to a mammal alone or in combination with pharmaceutically acceptable carriers, as noted above, the proportion of which is determined by the solubility and chemical nature of the compound, chosen route of administration and standard pharmaceutical practice.

The physician will determine the dosage of the present therapeutic agents which will be most suitable for prophylaxis or treatment and it will vary with the form of administration and the particular compound chosen, and also, it will vary with the particular patient under treatment. The physician will generally wish to initiate treatment with small dosages by small increments until the optimum effect under the circumstances is reached. The therapeutic dosage can generally be from about 0.1 to about 1000 mg/day, and preferably from about 10 to about 100 mg/day, or from about 0.1 to about 50 mg/Kg of body weight per day and preferably from about 0.1 to about 20 mg/Kg of body weight per day and can be administered in several different dosage units. Higher dosages, on the order of about 2× to about 4×, may be required for oral administration.

Additional objects, advantages, and novel features of this invention will become apparent to those skilled in the art upon examination of the following examples thereof, which are not intended to be limiting.

EXAMPLES

Example 1

This example describes the construction of a recombinant baculovirus expressing soluble FcγRIIa protein and the production of such protein.

Recombinant molecule pFcγRIIa, containing a nucleic acid molecule encoding a soluble form of human FcγRII (sFcγRIIa) operatively linked to baculovirus polyhedron transcription control sequences was produced as follows. The nucleic acid molecule sFcγRIIa was polymerase chain reaction (PCR) amplified from about 10 nanogram (ng) of Fc RIIa$^{LR}$ cDNA (described in detail in Ierino, et al., *J. Exp. Med.*, vol. 178, pp. 1617-1628, 1993) using about 100 ng of primer NRI having the nucleic acid sequence 5'-TAC GAA TTC CTA TGG AGA CCC AAA TGT CTC-3' (denoted SEQ ID NO:1) and primer FI2 having the nucleic acid sequence 50-CAT TCT AGA CTA TTG GAC AGT GAT GGT CAC-3' (denoted SEQ ID NO:2), using standard PCR methods. The resulting PCR product is 510 base pairs (referred to herein as sFcγRIIa(a)) and encodes the amino acid sequence represented herein by SEQ ID NO:3. Based on the results obtained in the Mass Spectroscopy experiment described in Example 7, a second protein product is present upon expression of a recombinant molecule comprising a PCR product of this Example. This data suggests that two PCR products were produced from the present method. The second PCR product is predicted to be 513 base pairs (referred to herein as sFc.RIIa (b)) and encodes the amino acid sequence represented herein by SEQ ID NO:12. The PCR products were digested with restriction endonucleases EcoRI and XbaI and ligated into unique EcoRI and XbaI sites of pVL1392 baculovirus shuttle plasmid (available from Pharmingen, San Diego, Calif.) to produce recombinant molecules referred to herein as pVL-sFc.RIIa (a) and pVL-sFc.RIIa (b).

The recombinant molecules pVL-sFc.RIIa (a) and pVL-sFc.RIIa (b) were co-transfected with baculovirus strain AcMNPV (available from Pharmingen) into *Spodoptera frugiperda* 21 (Sf-21) cells (available from Invitrogen Corp., San Diego, Calif.) to produce *S. frugiperda*:pVL-sFc.RIIa (a)/sFc.RIIa (b) cells. Putative recombinant virus isolates were selected by screening on X-galactosidase plates for occlusion of b-galactosidase. Selected isolates were grown on monolayers of Sf-21 cells for infection using serum-free Sf900-II media (available from Gibco, N.Y.) and the supernatant harvested about 40 hours post-infection. The presence of recombinant protein, referred to herein as PsFc.RIIa, in the supernatants was determined by ELISA using anti-Fc.RII monoclonal antibodies 8.26 and 8.7 (described in detail in Ierino, et al., *ibid.*) using standard methods. Based on the results described in Example 7, recombinant protein PsFc.RIIa includes the two species of protein having SEQ ID NO:3 and SEQ ID NO:12.

Example 2

This example describes the purification of PsFcγRIIa for crystallization of the protein.

Supernatant from *S. frugiperda*: pVL-sFcγRIIa(a)/sFc-γRIIa(b) cells described above in Example 1 was harvested and then centrifuged at about x2000 rpm to remove cellular debri. Supernatant from the centrifugation was concentrated about five-fold using a Minitan$^a$ ultrafiltration system (available from Millipore, Bedford, Mass.) and then extensively dialyzed against a buffer containing 10 mM Tris-HCl pH 8.5, and 50 mM NaCl. The dialyzed solution was applied to a Q-Sepharose fast-flow ion exchange column (available from Pharmacia, Uppsala, Sweden). The column was washed with 10 mM Tris-HCl, pH 8.5, and then protein was eluted from the column using a salt gradient from about of 0 to about 500 mM NaCl, passed over the column over 4 hours. PsFc.RIIa was eluted from the column at approximately 150 mM NaCl. The partially purified product was dialyzed against a buffer containing 20 mM Tris-HCl pH 7.4, and 30 mM NaCl. The dialysate was applied to a HAGG immuno-affinity chromatography column (described in detail in Ierino, et al., ibid.). The column was washed with a buffet containing 20 mM Tris-HCl pH 7.4, and 30 mM NaCl. PsFc.RIIa was eluted from the column using a buffer containing 0.1 M sodium acetate pH 4.0, and 0.5 M NaCl. The eluant was neutralized using 3m Tris pH 8.0 and the dialysed against PBS (3.5 mM $NaH_2PO_4 2H_2O$, 16 mM $Na_2HPO_4$, 150 mM NaCl). The dialysate was then concentrated approximately fifty-fold using macro and nanosep-10 ultra-filtration concentration devices (available from Filtron, Northborough, Mass.) and the applied to a G75 Superdex gel filtration column equilibrated in PBS (available from Pharmacia, Uppsala, Sweden). Filtered PsFc.RIIa was dialyzed against 1 mM Tris-HCl pH 7.4 and concentrated to about 6 milligram per milliliter (mg/ml) of protein using macro and nanosep-10 ultra-filtration concentration devices. The purity of PsFcγRIIa was assessed by resolving the concentrated protein by SDS-PAGE and staining the protein with crocein scarlet.

An electronic scan of the resulting gel is shown in 9 1, in which lane A contains supernatant harvested from a *S. frugiperda*:pVL-sFcγRIIa(a)/sFc.RIIa (b) cell culture prior to the ion-exchange step, lane B contains protein eluted from the affinity column, lane C contains protein isolated from the gel filtration chromatography step and lane D contains a sample of the PsFcγRIIa concentrated to 6 mg/ml and that was used for further crystallization studies. The molecular weight markers are shown on the left side of the figure. The results indicate that the purified PsFcγRIIa was about 90% pure with apparent molecular weights of 25,000 daltons.

Example 3

This example describes two-dimensional non-equilibrium pH gel electrophoresis analysis of purified PsFcγRIIa.

Supernatant from *S. frugiperda*: pVL-sFcγRIIa(a)/sFc-γRIIa(b) was incubated with about 20 microliter (ml) of packed Sepharose 4B beads conjugated with F(ab') fragments of anti-FcγRII monoclonal antibody 8.26 (IgG2b) (the production of which is described in J. Immunol., vol. 150, pp. 1-10, 1993) for about 1 hour at 4 C. The beads were then washed with buffer containing 10 mM Tris-HCl pH 7.4, 2% wt/vol bovine serum albumin (available from Commonwealth Serum Laboratories, Melbourne, Australia), 1 mM PMSF (available from Sigma Chemical Co., St. Louis, Mo.), 0.1% vol/vol Aprotinin (available from Sigma Chemical Co.), and then with 10 mM Tris-HCl, pH 7.4. The beads were resuspended in about 50 ml isoelectric focusing denaturation buffer (9.5 M urea, 4% acrylamide, 2% wt/vol NP-40, 2% total ampholines and 50 mM dithiothreitol), spun at about x13,000 rpm for about 2 minutes, loaded onto 4% tube gels and overlaid with about 10 ml of overlay buffer (9 M urea, 1% total ampholines) and anode buffer (0.01 M phosphoric acid), and electrophoresed for about 5 hours at about 550 Volts. The gels were then removed from the glass tubes, equilibrated in SDS-PAGE sample buffer (62.5 mM Tris-HCl, pH 6.8, 50 mM dithiothreitol and 10% glycerol) for about 2 hours at room temperature and attached to the top of a 13% slab gel for SDS-PAGE.

The electrophoresed proteins were transferred to Immobilon-P$^-$ PVDF membrane (available from Millipore) using a semi-dry transfer cell (Biorad, Australia) under a 20 mA current for about 30 minutes. The membrane was blocked in PBS buffer containing 5% wt/vol skim milk for about 1 hour. The membrane was then incubated overnight with a rabbit anti-Fc.RII polyclonal antisera (diluted 1:10,000 in PBS containing 5% wt/vol skim milk) and then washed extensively with buffer (10 mM Tris-HCl, pH 8.0, 150 mM NaCl, 0.05% Tween-20). The polyclonal antisera was raised in rabbits by immunization with recombinant FcγRII protein. The animals were immunized with about 1 mg of FcγRII protein. For the first immunization, FcγRII protein was emulsified in complete Freunds adjuvant. Subsequent immunizations were performed using FcγRII protein emulsified in incomplete Freunds adjuvant. The membrane was then incubated with peroxidase-linked swine anti-rabbit antisera (available from Dako Corp., Denmark) (diluted 1:5000 in 10 mM Tris-HCl, pH 8.0, 150 mM NaCl and 0.05% Tween-20) for about 1 hour at room temperature. The membrane was washed before detection of the transferred protein using the enhanced chemiluminescence system (available from Amersham International, Australia).

Figure 2A:
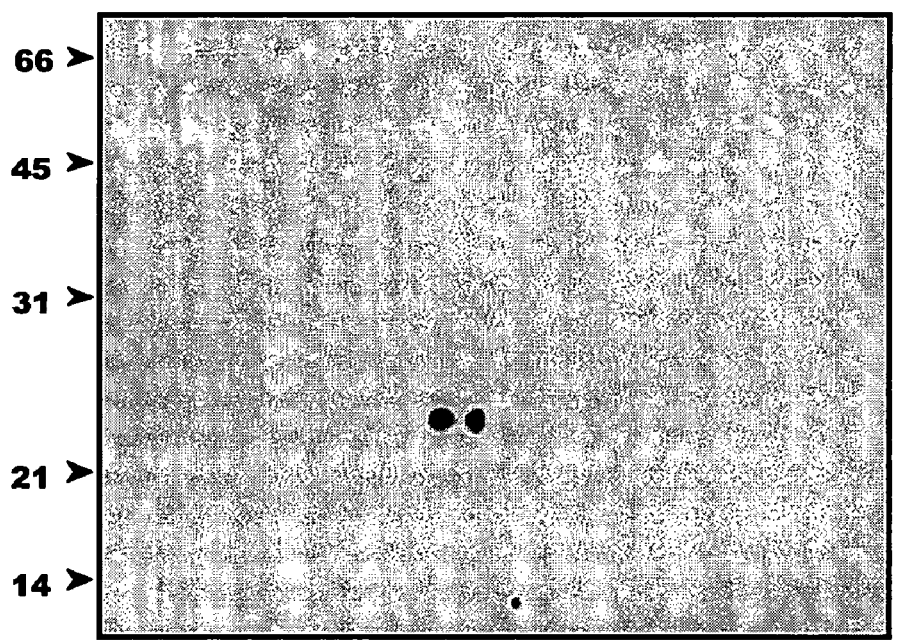
Figure 2B:
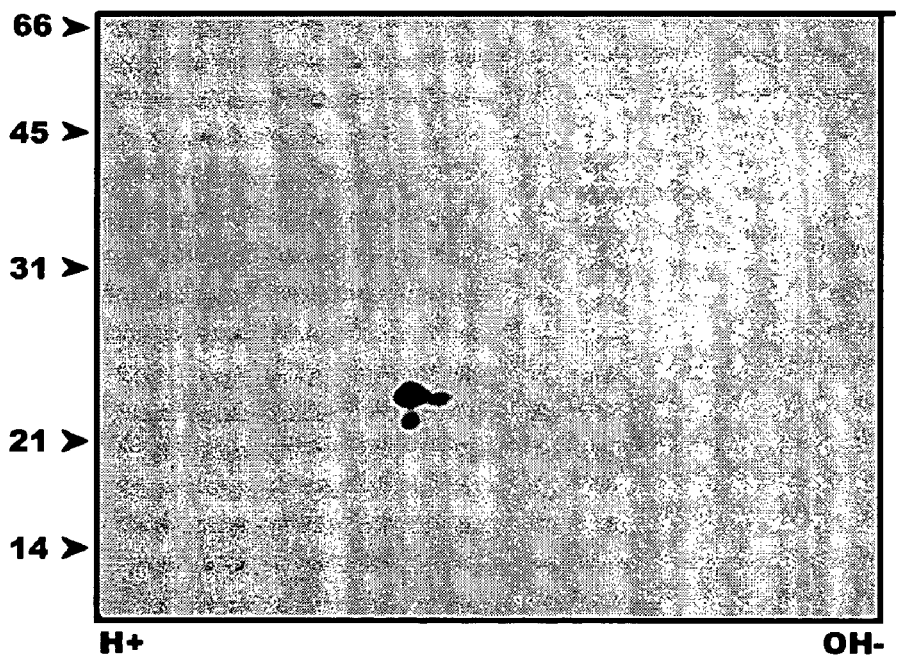

An electronic scan of the resulting gels are shown in FIGS. 2A and 2B. FIG. 2A illustrates the migration of protein isolated from supernatant harvested from *S. frugiperda*: pVL-sFcγRIIa(a)/sFcγRIIa(b) cell cultures after 34 hours. FIG. 2B illustrates the migration of protein isolated from supernatant harvested from *S. frugiperda*: pVL-sFcγRIIa (a)/sFcγRIIa(b) cell cultures after 73 hours. The molecular weight markers are shown on the left side of the figure. The results indicate that the purified PsFcγRIIa has an apparent molecular weight of 25,000 daltons and a pI at about pH 6.

Example 4

This example describes N-terminal peptide sequence of PsFcγRIIa. Amino acid sequencing of purified PsFc.RIIa described in Example 2 using standard sequential Edman degradation method using an Applied Biosystem 470A gas phase sequenator coupled to an Applied Biosystem 130 separation system for automatic on-line analysis of the first eight amino acids (available from Applied Biosystems, CA). The n-terminal sequence was determined to be Ala-Pro-Pro-Lys-Ala-Val-Leu-Lys (denoted as SEQ ID NO:4).

Example 5

This example describes the binding of PsFcγRIIa to monomeric immunoglobulin.

Analysis of the interaction between PsFcγRIIa and monomeric immunoglobulin was performed using a BIAcore$^a$ 2000 biosensor (available from Pharmacia Biotech, Uppsala, Sweden) at about 22 C in Hepes buffered saline (HBS; 10 mM Hepes [N-2-hydroxyethylpiperazine-N'-2-ethanesulfonic acid, available from Commonwealth Serum Laboratories, Parkville, Australia], pH 7.4, 150 mM NaCl, 3.4 mM EDTA and 0.005% Surfactant, available from Pharmacia). About 4000 to about 6000 response units (RU) of monomeric human immunoglobulin subclasses IgG1, IgG2, IgG3, and IgE (50 ug/ml of each) were covalently coupled to separate carboxymethylated dextran surface of each CM5 sensor-chips (available from BIAcore, Uppsala, Sweden) using a amine coupling kit (available from BIAcore), according to manufacturer's methods. A series of PsFcγRIIa concentrations (about 0.001 to about 1 mg/ml protein) was injected over each sensor-chip surface for about 1 minute at about 20 ul/min followed by about 3 minute dissociation phase. Following administration of the protein, the immunoglobulin surface was regenerated on each chip using a buffer containing 50 mM diethylamine pH 11.5, and 1 M NaCl. The equilibrium dissociation constants ($K_D$) for the interaction between PsFcγRIIa and immunoglobulin were obtained by non-linear curve fitting of a single site binding equation [Bound RU= $(B1_{max}.C)/(K_{D1}+C)$]; or a two site binding equation [Bound RU=$((B1_{max}.C)/(K_{D1}+C))+((B2_{max}.C)/(K_{D2}+C))$], where ($B1_{max}$ refers to the maximum binding capacity of the surface at site 1; $B2_{max}$ refers to the maximum binding capacity of the surface at site 2; C refers to the concentration of PsFcγRIIa) and by linear curve fitting to Scatchard plots. Data points obtained from the IgE channels were subtracted to correct for refractive index differences. Data points between 50 and 60 seconds were averaged to obtain the amount of PsFcγRIIa bound at equilibrium for each PsFc.RIIa concentration.

To determine the specificity of the interaction between PsFcγRIIa and immobilized immunoglobulin, the interaction between PsFcγRIIa with monomeric immunoglobulin was inhibited by the presence of excess monomeric IgG (Sandaglobulin, available from Sandoz, Basel, Switzerland). Using a fixed, half maximal dose of PsFcγRIIa (50 ug/ml), increasing concentrations of monomeric IgG (0 to 2 mg/ml IgG) were mixed with the PsFcγRIIa, at about 22 C for about 1 hour before passing the PsFcγRIIa over a sensor-chip surface coated with IgG1.

Figures 3A, 3B, 3C:
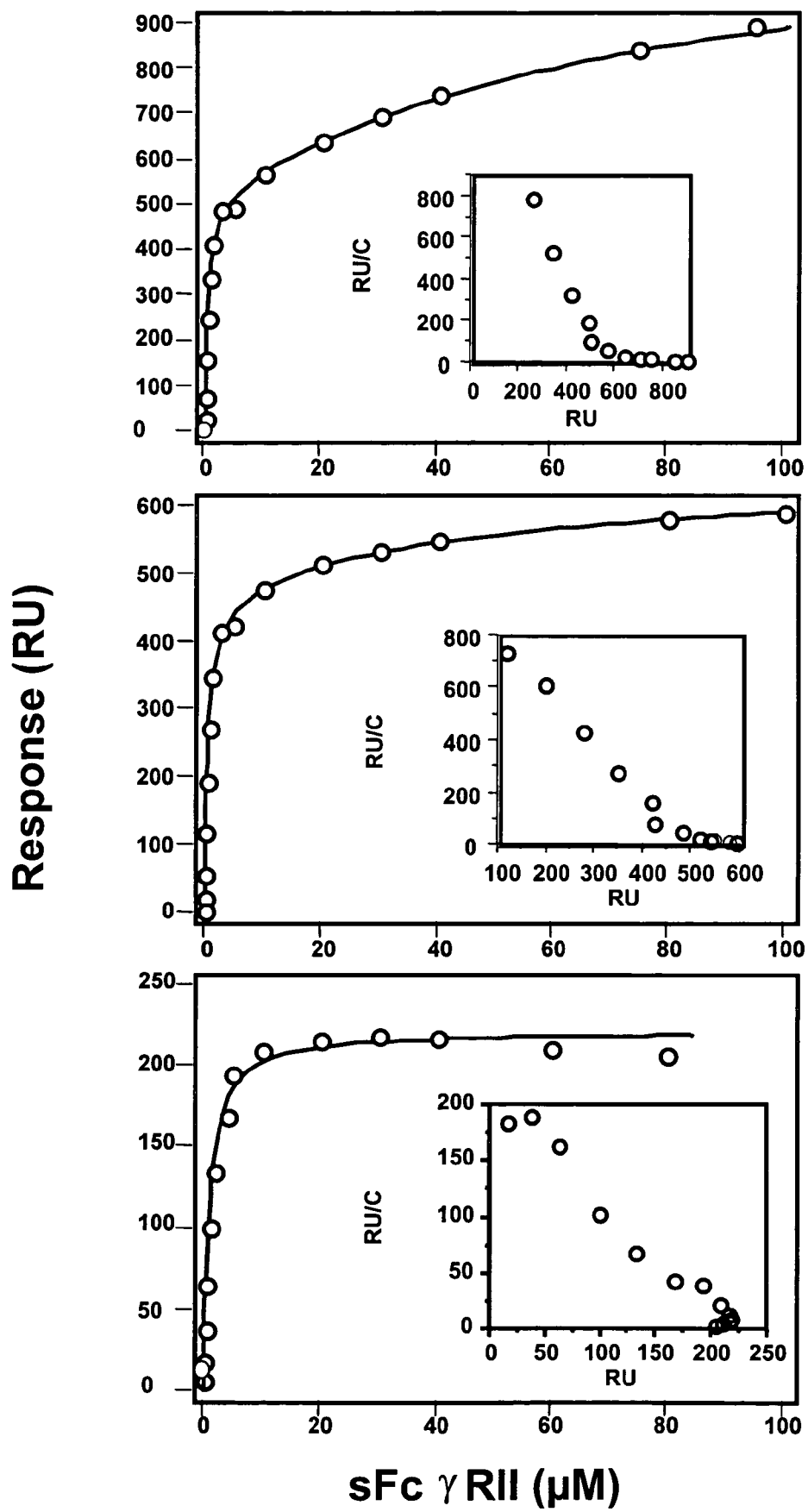

The results indicated that the binding of PsFcγRIIa to IgG3 and IgG1 was saturable over a broad range of protein concentrations. The maximum response units per protein concentration were plotted against the molar concentration of protein and curve fitting analyses undertaken. The curve of best fit suggests that there are two regions of PsFcγRIIa that interact with IgG3. At 50% of the sites, the affinity for IgG3 was about $2.7 \times 10^6 M^{-1}$ and at the remaining 50% of the sites the affinity was about $1.2 \times 10^4 M^{-1}$ (FIG. 3A). The interaction between PsFcγRIIa and IgG1 also occurred in two regions but the interaction was different from IgG3. Moreover, at about 90% of the ligand binding sites, the affinity of PsFcγRIIa for IgG1 was about $2.1 \times 10^6 M^{-1}$ and at the remaining 10% of sites the affinity was about $2.3 \times 10^4 M^{-1}$ (FIG. 3B). The interaction was specific for PsFcγRIIa since a six-fold molar excess of IgG completely inhibited binding of PsFcγRIIa to IgG. Analysis of IgG2 binding was also performed and a Kd value of about $8 \times 10^{-5} M^{-1}$ was obtained (FIG. 3C).

Example 6

This example describes crystallization and X-ray diffraction of PsFcγRIIa.

A. Production of Crystalline PsFcγRIIa

A series of alternative buffers were used to attempt to produce crystals of PsFcγRIIa by hanging drop vapor diffusion. Table 8 summarizes the different mother-liquor formulations used and the results obtained.

TABLE 6

Mother-liquor conditions and results of crystallization trial 3 mg/ml PsFcγRIIa.

| No. | SALT | BUFFER | PRECIPITANT[a] | pH | RESULT |
|---|---|---|---|---|---|
| 1 | 0.2M Calcium Chloride | 0.1 M Acetate | 30% MPD | 4.6 | clear drop |
| 2 | — | — | 0.4M Na K Tartrate | — | fine precipitation |
| 3 | — | — | 0.4M Amm. Phosphate | — | clear drop |
| 4 | — | 0.1M Tris | 2.0M Amm. Sulphate | 8.5 | clear drop |
| 5 | 0.2M Sodium Citrate | 0.1M Hepes | 40% MPD | 7.5 | phase separation |
| 6 | 0.2M Mg Chloride | 0.1M Tris | 30% PEG 4000 | 8.5 | dried up |
| 7 | — | 0.1M Cacodylate | 1.4M Sodium Acetate | 6.5 | clear drop |
| 8 | 0.2M Sodium Citrate | 0.1M Cacodylate | 30% Isopropanol | 6.5 | clear drop |
| 9[b] | 0.2M Amm. Acetate | 0.1M Sodium Citrate | 30% PEG 4000 | 5.6 | phase separation & crystal |
| 10 | 0.2M Amm. Acetate | 0.1M Acetate | 30% PEG 4000 | 4.6 | clear drop |
| 11 | — | 0.1M Citrate | 1.0M Amm. Phophate | 5.6 | clear drop |
| 12 | 0.2M Mg Chloride | 0.1M Hepes | 30% Isopropanol | 7.5 | clear drop |
| 13 | 0.2M Sodium Citrate | 0.1M Tris | 30% PEG 400 | 8.5 | phase separation |
| 14 | 0.2M Calcium Chloride | 0.1M Hepes | 28% PEG 400 | 7.5 | precipitation |
| 15 | 0.2M Amm. Sulphate | 0.1M Cacodylate | 30% PEG 8000 | 6.5 | precipitation |
| 16[c] | — | 0.1M Hepes | 1.5M Lithium Sulphate | 7.5 | splinters |

TABLE 6-continued

Mother-liquor conditions and results of crystallization trial 3 mg/ml PsFcγRIIa.

| No. | SALT | BUFFER | PRECIPITANT[a] | pH | RESULT |
|---|---|---|---|---|---|
| 17 | 0.2M Lithium Sulphate | 0.1M Hepes | 30% PEG 4000 | 7.5 | phase separation |
| 18 | 0.2M Mg Acetate | 0.1M Cacodylate | 20% PEG 8000 | 6.5 | clear drop |
| 19 | 0.2M Amm. Acetate | 0.1M Tris | 30% Isopropanol | 8.5 | clear drop |
| 20 | 0.2M Amm. Sulphate | 0.1M Acetate | 25% PEG 4000 | 4.6 | heavy precipitation |
| 21 | 0.2M Mg Acetate | 0.1M Cacodylate | 30% MPD | 6.5 | fine precipitation |
| 22 | 0.2M Sodium Acetate | 0.1M Tris | 30% PEG 4000 | 8.5 | fine precipitation |
| 23 | 0.2M Mg Chloride | 0.1M Hepes | 30% PEG 400 | 7.5 | skin over drop |
| 24 | 0.2M Calcium Chloride | 0.1M Acetate | 20% Isopropanol | 4.6 | clear drop |
| 25[d] | — | 0.1M Imidazole | 1.0M Sodium Acetate | 7.5 | crystal |
| 26 | 0.2M Amm. Acetate | 0.1M Citrate | 30% MPD | 5.6 | clear drop |
| 27 | 0.2M Sodium Citrate | 0.1M Hepes | 20% Isopropanol | 7.5 | clear drop |
| 28 | 0.2M Sodium Acetate | 0.1M Cacodylate | 30% PEG 8000 | 6.5 | clear drop |
| 29 | — | 0.1M Hepes | 0.8M Na K Tartrate | 7.5 | clear drop |
| 30 | 0.2M Amm. Sulphate | — | 30% PEG 8000 | — | precipitation |
| 31 | 0.2M Amm. Sulphate | — | 30% PEG 4000 | — | precipitation |
| 32 | — | — | 2.0M Amm. Sulphate | — | clear drop |
| 33 | — | — | 4.0M Sodium Formate | — | precipitation |
| 34 | — | 0.1M Acetate | 2.0M Sodium Formate | 4.6 | precipitation |
| 35 | — | 0.1M Hepes | 2.0M Na K Phosphate | 7.5 | precipitation |
| 36 | — | 0.1M Tris | 8% PEG 8000 | 8.5 | precipitation |
| 37 | — | 0.1M Acetate | 8% PEG 4000 | 4.6 | aggregation |
| 38 | — | 0.1M Hepes | 1.4M Na Citrate | 7.5 | heavy precipitation |
| 39 | — | 0.1M Hepes | 2.0M Amm. Sulphate 2% PEG 400 | 7.5 | fine precipitation |
| 40 | — | 0.1M Citrate | 20% PEG 4000, 20% Isopropanol | 5.6 | fine aggregation |
| 41 | — | 0.1M Hepes | 20% PEG 4000, 10% Isopropanol | 7.5 | clear drop |
| 42 | 0.05M K Phosphate | — | 20% PEG 8000 | — | clear drop |
| 43 | — | — | 30% PEG 1500 | — | clear drop |
| 44 | — | — | 0.2M Mg Formate | — | clear drop |
| 45 | 0.2M Zn Acetate | 0.1M Cacodylate | 18% PEG 8000 | 6.5 | heavy precipitation |
| 46 | 0.2M Ca Acetate | 0.1M Cacodylate | 18% PEG 8000 | 6.5 | fine precipitation |
| 47 | — | 0.1M Acetate | 2.0M Amm. Sulphate | 4.6 | heavy precipitation |
| 48 | — | 0.1M Tris | 2.0M Amm. Sulphate | 8.5 | fine precipitation |
| 49 | 1.0M Li Sulphate | — | 2% PEG 8000 | — | med precipitation |
| 48 | — | 0.1M Tris | 2.0M Amm. Sulphate | 8.5 | fine precipitation |
| 49 | 1.0M Li Sulphate | — | 2% PEG 8000 | — | med precipitation |
| 50 | 1.0M Li Sulphate | — | 15% PEG 8000 | — | heavy precipitation |

[a]Final concentration of precipitant used to achieve the result listed.
[b]Condition 9 produced two crystals in the single droplet.
[c]Condition 16 produced a shower of splinters that have arisen from numerous nucleation points within the droplet.
[d]Condition 25 produced an unusual crystal. Numerous crystalline plates appear to be joined together to form this crystal. X-ray diffraction analysis of this crystal was not successful.

A rapid screening method (generally described in McPherson, 1982, In: Preparation and Analysis of Protein Crystals, 1982, pp. 94-97, John Wiley and Sons, pub.; and *J. Crystal Growth*, vol. 122, pp. 161-167, 1992) was used. Briefly, hanging drop vapor diffusion experiments were performed using 24-well culture plates. Droplets (about 3 Ul) containing about 3 mg/ml of PsFc.RIIa in an equal volume of a mother-liquor were suspended from siliconized coverslips inverted into 24-well tissue culture plates well. The droplets were equilibrated at about 22 C against about 1 ml mother-liquor. Controlled temperature incubation was performed in chambers (available from Linbro Inc, distributed by ICN Inc, Costa Mesa Calif.) at about 22 C. Successful PsFc RIIa crystallization was performed using the mother-liquor 0.2 M ammonium acetate, 0.1 M citrate pH 5.6 and 30% PEG 4000, at 22 C for between about 3 to about 9 days, or up to 9 months depending upon the purity and concentration of the PsFc-γRIIa, resulting in the production of orthorhombic crystals.

Successful PsFcγRIIa crystallization was also performed using the mother-liquor 0.1 M HEPES pH 7.5 with 1.5 M lithium sulphate, at 22 C for between about 3 to about 9 days, or up to 9 months depending upon the purity and concentration of the PsFcγRIIa, resulting in the production of a series of rod-like splinters of defined structure. The rod-like splinters were analyzed by X-ray diffraction.

B. X-ray Diffraction of Crystalline PsFcγRIIa and Determination of Electron Density Map The PsFcγRIIa crystals produced as described above in section A were mounted in rayon loops and cryo-cooled to −165° C. in mother liquor containing 20% glycerol. Twelve heavy atom compounds which sampled a broad range of activities were tested for binding to PsFcγRIIa. PIP (Di-u-iodo bis[ethylenediamine] di Platinum(II) nitrate) was found to be reactive. Crystals were derivatized by soaking overnight in mother liquor containing about 5 mM PIP. Diffraction measurements were made with a M18XHF rotating anode generator (Siemens, Germany) operating at about 40 KV and about 50 mA and using Ni filtered CuK radiation. The generator was equipped with Franks mirrors (Molecular Structure Corporation, USA), a low-temperature system (Molecular Structure Corporation, USA) and RAXIS IIC and IV image plate detectors (Rigaku, Japan).

The crystals belong to the space group $P2_12_12$ ($a$=78.80 Å, $b$=100.55 Å, $c$=27.85 Å) and diffracted to about 2.4 Å resolution with an R(merge) of 0.065. R(merge)=$S(I_i-(IS))/I_i$ summed over all independent reflections where I=intensity. Native and derivative data were collected at 45 minute exposures with an oscillation range of about 1°. Diffraction intensities were integrated using DENZO (Otwinowski, et al., Methods in Enzymology, vol. 276, p. 307, 1996) and scaled with SCALEPACK (Otwinowski, et al., ibid.). A single heavy atom binding site was located by inspection of isomorphous and anomalous difference Patterson maps (Blundell, et al., In: Protein Crystallography., Horecker, B., Kaplan, N. O., Marmur, J., Scheraga, H. A., Eds., Academic Press, New York, 1976) calculated with the PROTEIN system (Steigeman, Ph.D. Thesis, Technical University, Munich, 1974). Heavy atom parameters were refined and phases were determined in a method of Single Isomorphous Replacement with Anomalous Scattering using the program SHARP (Statistical Heavy-Atom Refinement and Phasing (de La Fortelle, et al., Methods in Enzymology, vol. 276, p. 472, 1996). Merged data in the range of about 18 to about 2.7 Å resolution had an isomorphous R-factor of about 0.162, figure of merit for centric reflections 0.308 and acentric reflections 0.247 and phasing power of 1.127 for centric reflections and 1.081 for acentric reflections (Blundell, ibid.). Phases were modified in a protocol of solvent flattening (Wang, Methods in Enzymology, vol. 115, p. 90, 1985) and histogram mapping (Zhang, et al., Acta Crystallography, vol. A46, p. 377, 1990) in the density modification package DM (Cowtan, Joint CCP4 and ESF-EACBM Newsletter on Protein Crystallography, vol. 31, p. 34, 1994) in the CCP4 suite of programs (Cowtan, ibid.). 2Fo-Fc electron-density maps were displayed using the graphical display program 0 (Jones et. al., Acta Crystallography, vol. A47, p. 110, 1991). Secondary structural features could be identified at this stage, however the map was difficult to fully interpret and trace of the polypeptide. To produce a simplified representation of the electron density, the map was skeletonised (Greer, J. Mol. Biol., vol. 82, p. 279, 1974) using the program BONES (Jones, et al., ibid.). Coordinates of Killer Inhibitory receptor (Fan, et. al., Nature, vol. 389, p. 96, 1997) and were used as a reference to trace the polypeptide and generate a partial model. To calculate subsequent maps density modified phases and phases calculated from the model were combined by the Free-Sim method (Sim, Acta Crystallography, vol. 13, p. 511, 1960).

Additional data for structure refinement were collected at beam line X4A of the National Synchrotron Light Source at Brookhaven National Laboratory (Upton, N.Y.). Using radiation with a wavelength of about 1.058 Å, data were collected on Fuji image plates as exposures of about 100 seconds and oscillation ranges of about 10. Diffraction images were digitized with a BAS 2000 scanner (Fuji, Japan) and processed as described above, giving an R(merge) of 0.038 for data between about 10 Å and about 1.7 Å resolution. Structure refinement was performed with the XPLOR system (Brunger, et al., Science, vol. 235, p. 458, 1987) using protocols including individual temperature factor, energy minimization and slow-cool simulated annealing refinement with bulk solvent correction.

Figure 4:
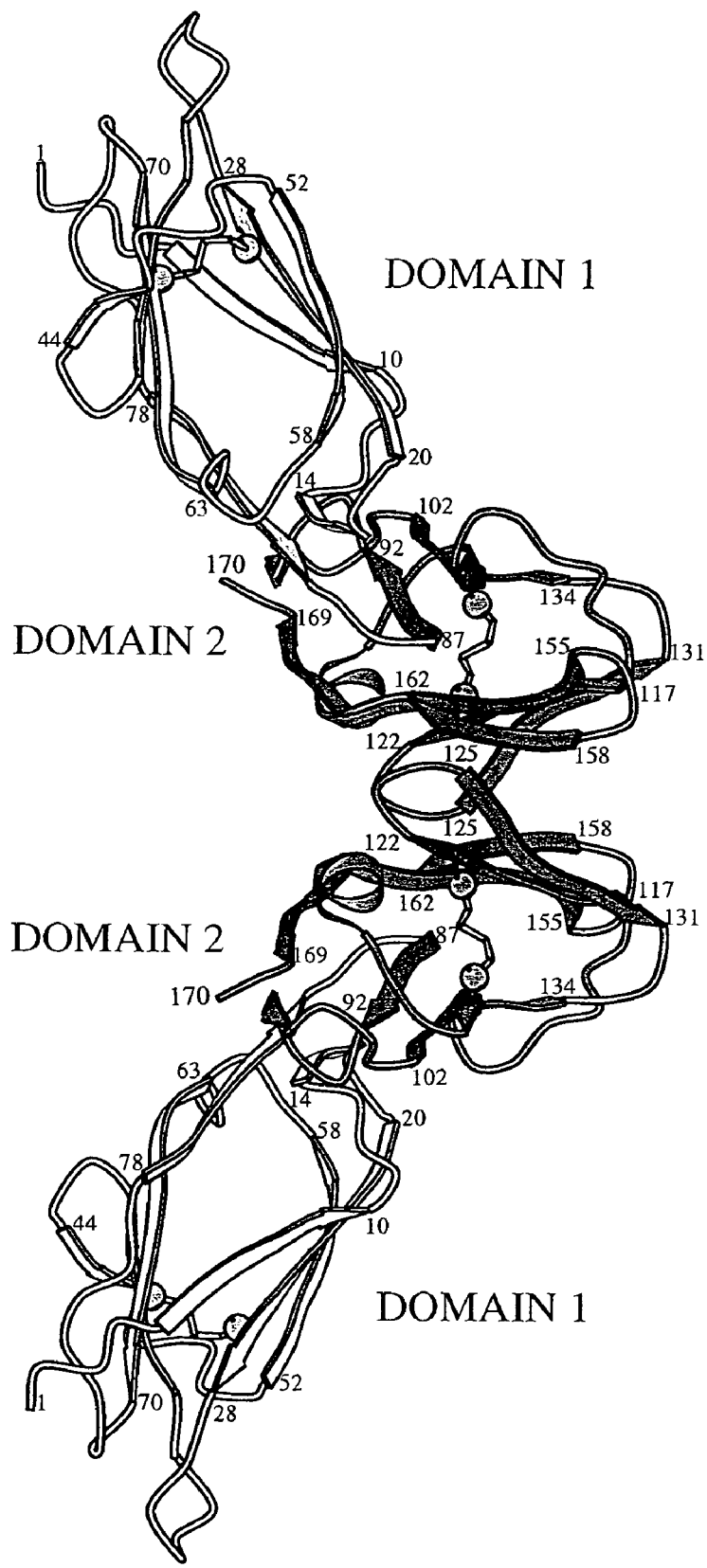

The refined structure of PsFcγRIIa contains all amino acid residues from 1 to 170, together with 33 solvent molecules. The crystallographic residual R-factor and Free R-factor are about 0.253 and about 0.326 respectively for data of from about 7 Å to about 2.0 Å resolution (Brunger, 1987, ibid.). Root mean squared deviations from ideality for bond lengths was about 0.01 Å and about 1.45° for angles (Brunger, et al., Nature, vol. 355, p. 472, 1992). The resulting data set of the atomic coordinates for PsFcγRIIa is shown in FIG. 4.

C. PsFcγRIIa Structure

Using the atomic coordinates listed in Table 3, a structure of a dimer of PsFcγRIIa was derived. The structures were computer generated using MOLSCRIPT 2.0 program (available from Avatar Software AB, Heleneborgsgatan 21 C, SE-11731 Stockholm, Sweden) The crystal structure reveals PsFcγRIIa in a dimeric form having two 170 amino acid monomers. The two monomers are structurally identical.

The structure of the PsFcγRIIa residues 1 to 170 consists of two immunoglobulin constant region 2 (C2) type immunoglobulin domains and each domain is comprised of two antiparallel b-sheets, pinned together by a disulfide bond. The first strand of each domain (A strand) is broken in the middle with part forming sheet I (ABE strands) and part forming sheet II (A'GFCC' strands). This structural feature occurs in immunoglobulin variable region (V) type domains and in the natural killer inhibitory receptor (KIR) but not in other C2 domains. The two immunoglobulin-like domains of PsFc-γRIIa are quite similar to each other with the rms difference in Cα positions of 1.28 Å for 68 residues. Major differences are in the loops at the N-terminal end of the molecule (BC, C'E and FG loops) and in the position on the C' strand. Some of these loops have been implicated in binding Fc.

The region of association of the two domains in the PsFc-γRIIa structure is quite bent, with the angle between the major axes of the domains being approximately 52°. This bend is more severe than other immunoglobulin super family members including 60° for KIR. The domain interface is composed of strands A' from Domain 1 and A & B from Domain 2, where sheet II from each domain forms the interface.

Residues whose non-hydrogen atoms lie within 4 Å of the other domain. Water molecules 201, 211, 217-220, 227 and 232 also lie in the interface region.

Certain structural characteristics indicate that dimer formation between two PsFcγRIIa molecules in the crystal is a preferred interaction. Although the structure of only one PsFcγRIIa molecule (residues 1 to 170) of the crystal has been determined, each PsFcγRIIa molecule comprising the dimer in the crystal is related to the other PsFcγRIIa molecule in the crystal by a 2-fold crystallographic axis. By applying the transformation:

(−1 0 0) (x) (0.)

(0−1 0)·(y)+(100.55)

(0 0 1) (z) (0.)

to the coordinates given in Table 1 a dimer is formed (FIG. 4), with the interface composed of sheet II from each PsFcγRIIa molecule. The coordinates of the FcγRIIa dimer are represented in Table 2. The contact area is substantial (~400 Å$^2$) and this interface has more hydrophobic character than the Domain 1-Domain 2 interface. Residues whose non-hydrogen atoms lie within 4 Å of the other molecule or water molecule 207 on the axis are 119, 121, 124-126, 150, 152 and 158-161, with residues 148, 163 and 164 also making a close approach. This type of domain interaction is not novel for immunoglobulins because V regions of antibodies pair in a similar manner. This type of interaction, however, has not been observed for C2 domains. Due to the size and character of this contact it suggests that this hitherto unforeseen interaction has physiological relevance.

Additional structural considerations support this conclusion. The crystal structure described above suggests that, if an FcγRIIa molecule is oriented with the C-terminus toward a cell membrane containing the receptor, then the putative Fc binding region of the receptor does not point away from the cell but to one side. Thus, forming a dimer between two FcγRIIa molecules in a cell membrane, the two potential Fc binding regions are brought near each other and point away from the cell because the dimer axis points away from the cell. This orientation positions the potential Fc binding sites ideally for interaction with ligand (i.e., IgG), enabling the ligand binding site to be composed of regions from two receptor molecules. Involving two receptor molecules in a binding event has implications for cellular signal transduction because dimerization of the extracellular domains would bring the cytoplasmic domains of the two receptors together to initiate a cellular signal transduction response.

Figure 6:

FIG. 4 shows a graphical representation of the dimer of PFcγRIIa. Two Ig-like domains (Domains 1 and 2) are shown in each monomer of each dimer. The first amino acid residue of the amino (NH2) terminus of the protein is indicated by residue number 0. The last amino acid residue of the carboxyl (COOH) terminus of the protein is indicated by residue 170. Numbering of amino acid residues from the NH2 terminus to the COOH terminus are shown where possible. Certain residues were omitted for clarity. FIG. 5 illustrates the amino acid residues that comprise each beta sheet of Domain 1 and Domain 2 of PFc.RIIa. In Domain 1, strand A includes residues 5-10, strand A' includes residues 14-17, strand B includes residues 20-28, strand C includes residues 37-41, strand C' includes residues 44-46, strand E includes residues 52-58, strand F includes residues 63-70 and strand G includes residues 78-84. In Domain 2, strand A includes residues 87-92, strand A' includes residues 95-97, strand B includes residues 102-110, strand C includes residues 117-122, strand C' includes residues 125-131, strand E includes residues 134-139, strand F includes residues 146-155, strand G includes residues 158-162 and strand G' includes residues 163-169. FIG. 6 shows the stereo view of the structure of the polypeptide shown in FIG. 4 in stereo.

Figure 8:
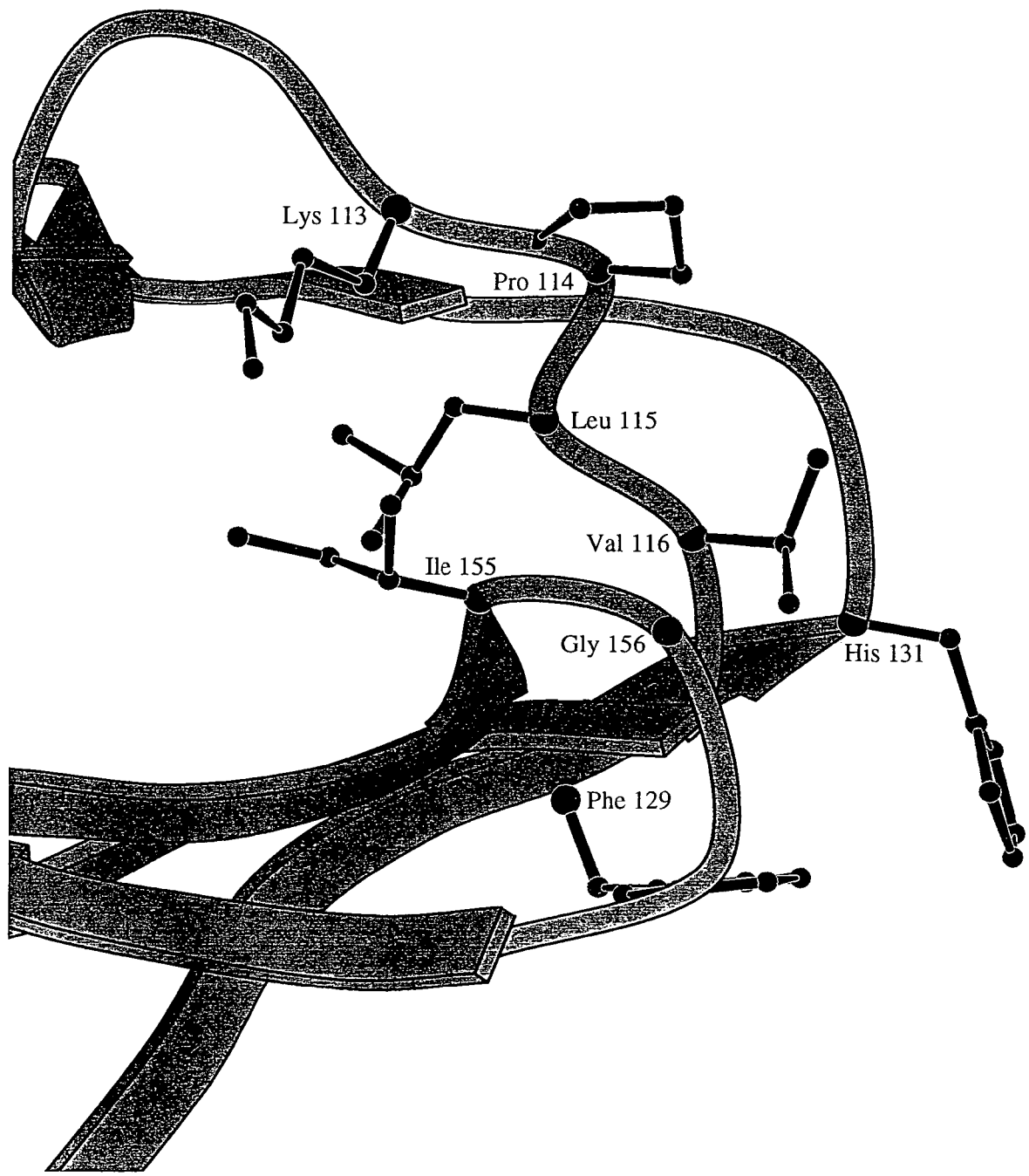

A graphical representation of the three dimensional structure shown in FIG. 4 was used to determine the location of amino acid residues involved in the binding of FcγRIIa to IgG. FIG. 7 shows the location of the mutated alanine residues (indicated by the black balls) involved in the loss of binding of FcγRIIa to IgG. The residues shown in FIG. 7 were identified using recombinant mutants of FcγRIIa, in which residues were replaced with alanine and were found to disrupt or decrease IgG binding to FcγRIIa (described in Hulett, et al., 1994, ibid.; Hulett, et al., 1995, ibid.). FIG. 8 shows an expanded view of the IgG binding region showing position and side chains of amino acids involved in IgG binding to FcγRIIa, as shown by production of nucleic acid molecules having mutations in this region that encode an FcγRIIa protein having reduced binding to IgG.

Figure 9:
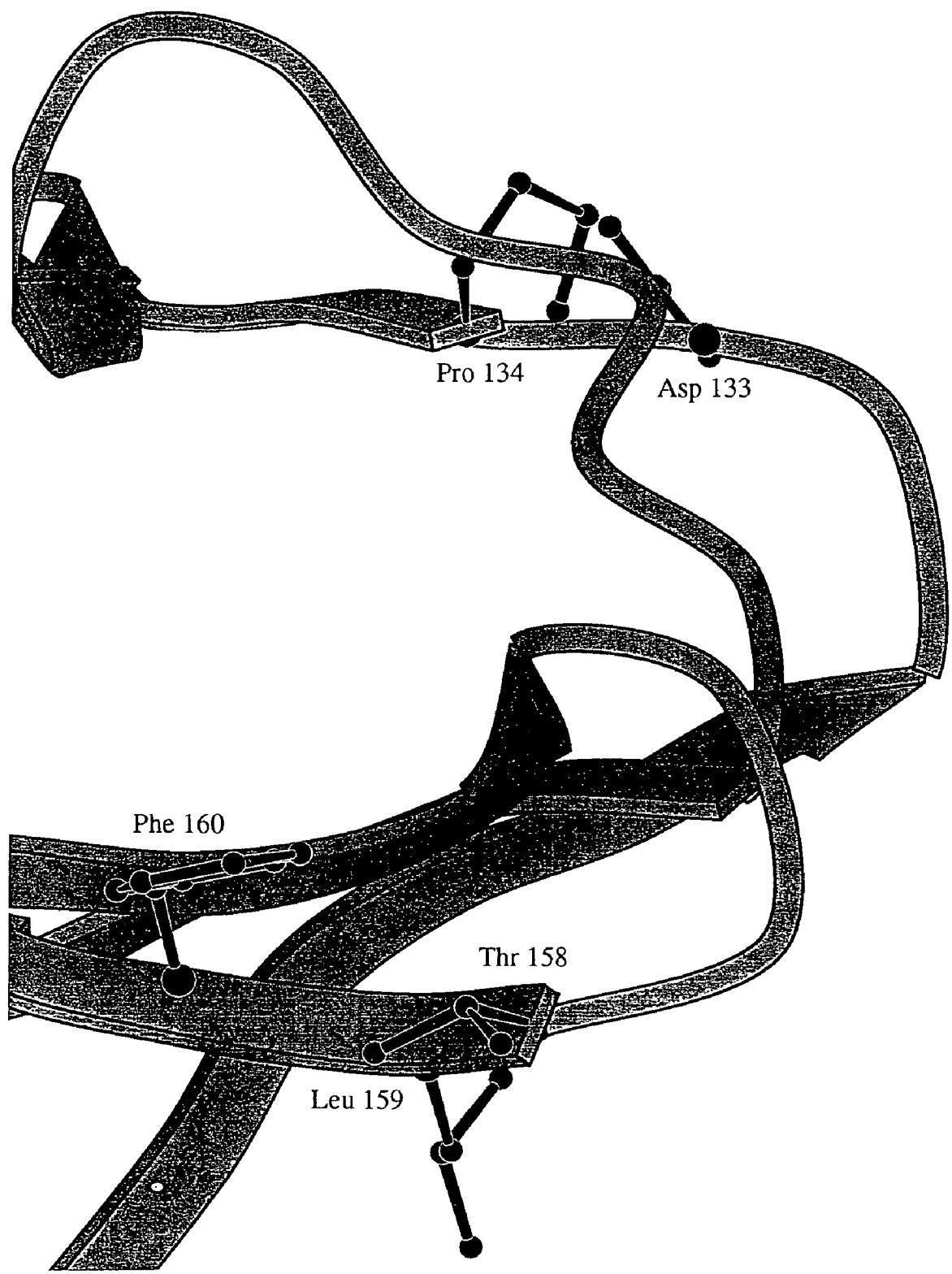

FIG. 9 shows an expanded view of the IgG binding region and the amino acid residues, which when mutated to alanine, improve IgG binding.

The interface between the two dimers illustrated in the graphical representation of the three dimensional structure shown in FIG. 4 was further analyzed. FIG. 10 shows an expanded view of the region of one FcγRIIa monomer that contributes to the dimer interface. In FIG. 10, the region has been rotated about 90° in x, where x is horizontal to the page. The a carbon of amino acid residues contributing to the interface are shown as black balls and are numbered according to the residue numbering of SEQ ID NO:3.

Example 7

This example describes analysis of N-terminal sequence of PsFcγRIIa protein by electrospray ionization mass spectrometry.

To determine the N-terminal amino acid sequence of PsFcγRIIa protein, the heterogeneity of the N-linked glycosylation mass spectrometry was carried out as follows. Various samples were prepared by combining about 1 to about 100 picomolar (pmol) of PsFcεRIIa protein in about 2 ul to about 4 ul of 50% CH$_3$CN containing 0.1% acetic acid. The samples were infused at a flow rate of about 0.2 ul/min into a Perkin Elmer Sciex API-300 triple quadrupole mass spectrometer fitted with a micro-ionspray ion source and operated in the Q1 scan mode. The mass scale was calibrated at eight points over the 3000 u mass range, to an accuracy equivalent to ±0.01%, using singly charged poly(propylene glycol) ions. Mass spectra (typically 30-100 scans) were recorded over the mass rand m/z200 u to 3000 u with a constant peak width of 0.6 u (peak width at half-height), and were processed by signal-averaging, manual mass determination and transformation using PE-Sciex Biomultiview software. The results indicated that two major species of protein having different N-terminal sequence were present in the solution of purified PsFcγRIIa protein. One species had a N-terminal sequence comprising SEQ ID NO:4 and the other species had a N-terminal sequence with an additional Ala at the 5' end of the protein (e.g., Ala-Ala-Pro-).

Example 8

This example describes the modeling of the three dimensional structure of the Fcε receptor I (FcεRI) in both monomeric and dimeric forms.

The extracellular regions of the human Fc epsilon receptor type I (FcεRI) and the human Fc gamma Receptor type II a (FcγRIIa) show a sequence identity of about 38% (for 172 residues). The final sequence alignment used in this modeling work is shown in FIG. 13. The X-ray crystallographic structure of the human FcγRIIa was determined by the present inventors (Table 1). The 3-dimensional coordinates of FcγRIIa in Table 1 differ from those used as the template to build a 3-dimensional model of the human FcεRI by orientation of the imidazole ring of His 108 and one round of refinement.

Secondary structure prediction performed on FcεRI confirmed the validity of the alignment given in FIG. 13 and showed the pattern of β strands is the same in both FcεRI and FcγRIIa. The secondary structure prediction methods used were PHD (B. Rost et al., CABIOS, vol. 10, 266-275(1994)) and PREDATOR (D. Frishman and P. Argos, Proteins, vol. 27, 329-335 (1997)).

MODELER (A. Sali and T. L. Blundell, J. Mol. Biol., vol. 234, 779-815 (1993)) as implemented in the InsightII-Homology software package (Insight II (97.0), MSI, San Diego) was used to generate 3-dimensional models of FcεRI using a number of different initial sequence alignments and two structural templates of FcγRIIa. One of the structural templates was the 3-dimensional coordinates of FcγRIIa where, for the residues that had alternative side-chain conformations (residue numbers 10, 21, 33, 57, 60, 61, 65, and 89), the conformations labeled 'A' were selected while in the other template the conformations labeled 'B' were selected. In each Modeler run 5 structural models of FcεRI were generated. The following parameter values or options were used: 'library-schedule' of 1, 'max-var-iterations' of 300, 'md-level' of 'refine1', 'repeat-optimization' of 3, and 'max-molpdf' of 1e6. The best model from these runs had the sequence alignment given in FIG. 13, and used the structural template of FcγRIIa, where residues 10, 21, 33, 57, 60, 61, 65, and 89 had side-chains in the 'A' conformation. The criteria for judging the 'best' model included the lowest value of the Modeler objective function (or $-1.0 \times \ln$(Molecular probability density function=Mpdf)), 'well-behaved' PROSAII (M. Sippl, Proteins, vol. 17, 355-362 (1993)) residue energy plot for the model (for example, negative residue energy scores throughout the sequence), and 'well-behaved' PROFILES-3D (J. U. Bowie et al., Science, vol. 253, 164-170 (1991)) local 3D-1D compatibility score plot (for example, positive plot scores throughout the sequence).

Figure 14:
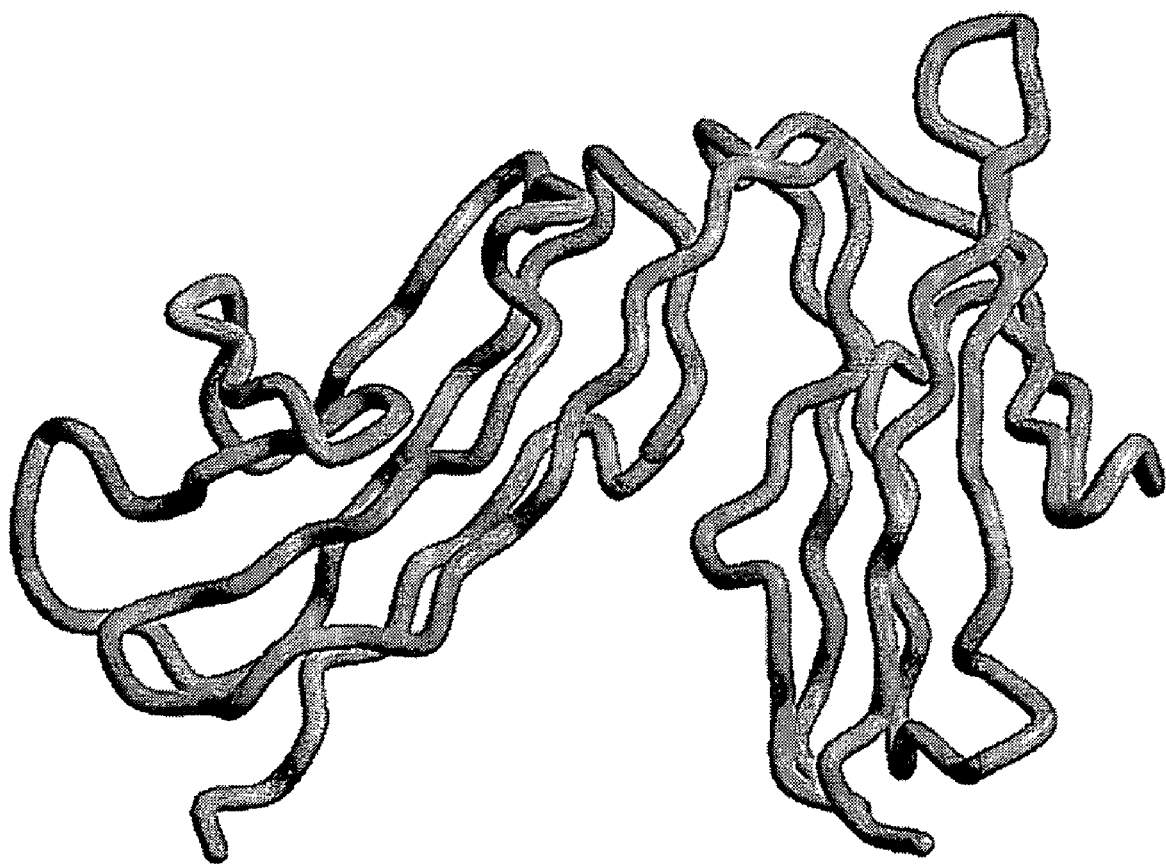

Next, Modeler was used to generate 20 different structural models of FcεRI using the sequence alignment and template selected above, and using the parameter values and options listed above. The model with the lowest $-\ln$(Mpdf) value (i.e. 957.2) was then selected as the template to generate structural models of the FcεRI sequence in the next cycle of Modeler runs. At the end of four such cycles, the 'best' 3-dimensional model of the FcεRI structure had a $-\ln$(Mpdf) value of 643.2. This was selected as the final structural model of the FcεRI monomer, and the corresponding heavy (non-hydrogen) atom Cartesian coordinates are represented in Table 3. A 'worm' representation of the structure is shown in FIG. 14. This structure was validated with the programs PROSAII, PROFILES-3D, and PROCHECK (R. M. Laskowski et al., J. Appl. Cryst. vol. 26, 283-291 (1993)).

Figure 15:
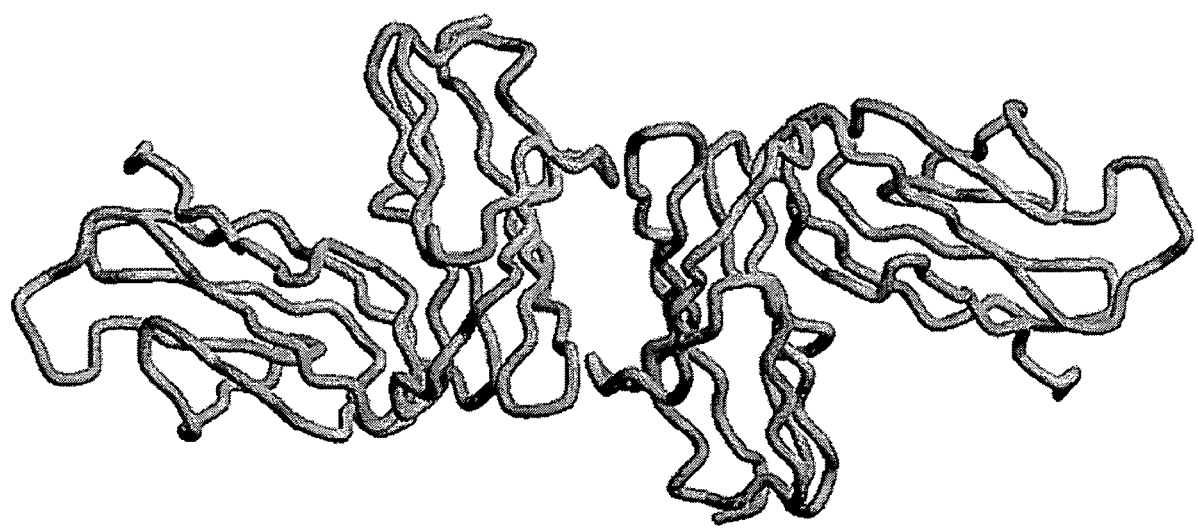
Figure 16:
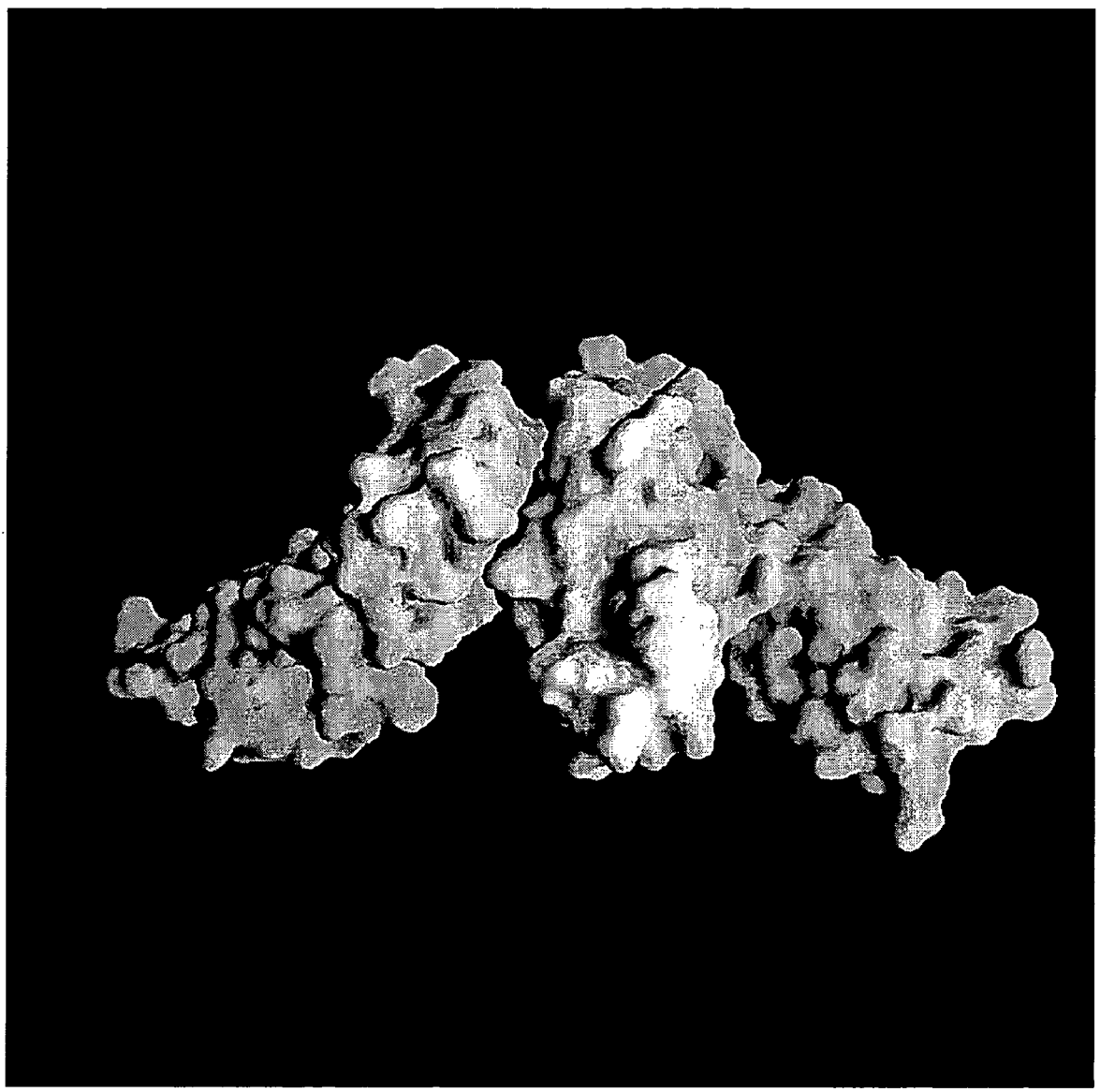

Finally, the same coordinate transformation that generates a dimer from the FcγRIIa monomer was applied to the above model of the FcγRI monomer. The interface of the resultant dimer was optimized by selecting alternative rotamers for the Glu 161 and Tyr 150 residues with the Auto-Rotamer option of the InsightII-Homology module (MSI, San Diego), and then adding hydrogen atoms to the dimer model and energy minimizing it keeping all heavy atoms fixed, except for Tyr 150 and Glu 161 where only the backbone atoms were kept fixed. The program Discover v. 2.98 (MSI, San Diego) was used for the energy minimization with the CFF91 force field and a distance-dependent dielectric constant of $1.0 \times r$, and the minimization was done with the conjugate gradients method until the maximum energy gradient was less than 0.10 kcal/Å. The Cartesian coordinates of the resultant model of the FcεRI dimer are represented in Table 4 and a 'worm' representation of the dimer model is shown in FIG. 15. This model of the Fc RI dimer has a shape complementarity or Sc value (see M. C. Lawrence and P. M. Colman, J. Mol. Biol., vol. 234, 946-950 (1993)) at the monomer-monomer interface of 0.64 and an electrostatic complementarity value—for the fully solvated case, using the Spearman correlation coefficient—(see A. J. McCoy, V. C. Epa, and P. M. Colman, J. Mol. Biol., vol. 268, 570-584 (1997)) or ECSFS at the monomer-monomer interface of 0.08. These compare with 0.80 and 0.32, respectively, for the FcγRIIa dimer. These reduced complementarity values for the FcεRI dimer compared to the FcγRIIa dimer indicates that formation of the FcεRI dimer, as built herein, is energetically less favored than it is in the FcγRIIa case. However, we note that the interaction with the β or γ chains of the FcεRI has not been taken into consideration. FIG. 16 shows a molecular surface representation of the FcεRI dimer model.

The model of the 3-dimensional structure of FcεRI monomer represented by the coordinates in Table 3 or the FcεRI dimer represented by the coordinates in Table 4 may be used as a basis for drug design in the same manner as that described for the crystallographic coordinates of FcγRIIa herein.

Example 9

The following example demonstrates the crystallization of the Fc. receptor I (FcεRI) Recombinant molecule pFcERI, containing a nucleic acid molecule encoding a soluble form of human FcεRI (sFcεRI) operatively linked to baculovirus polyhedron transcription control sequences was produced as described for the pFcγRIIa molecule in Examples 1-3. Briefly, the recombinant soluble FcεRI was generated by placing a translation termination codon at the position 173 which normally encodes a Pro in the sequence Ile, Lys, Ala, Pro, at the C-terminal end of the second domain as set forth in the sequence represented in FIG. 13. Soluble FcεRI was expressed in baculovirus expression system 'Bac to Bac' supplied by GIBCO. Infections of SF21 or Sf9 cells were performed as described by the manufacturer. Briefly, the recombinant FcγRIIa molecule was ligated into pVL1392 baculovirus shuttle plasmid (available from Pharmingen, San Diego, Calif.) to produce a recombinant molecule referred to herein as pVL-sFcεRI. The recombinant molecule pVL-sFcεRI was subsequently co-transfected with baculovirus strain AcMNPV (available from Pharmingen) into Spodoptera frugiperda 21 (Sf-21) cells (available from Invitrogen Corp., San Diego, Calif.) to produce S. frugiperda: pVL-sFcεRI cells. 65-70 hours following infection, supernatants were harvested and soluble receptor was purified by affinity chromatography on an anti-FcεRI antibody (3B4) monoclonal antibody-sepharose 4B affinity column, similar to the processes described for FcγRIIa in Example 5. The column was washed with 10 mM Tris pH 7.5 and eluted with 0.1 M sodium acetate, 0.5M sodium chloride, pH4.0. The purified protein was concentrated and used in crystallization trials as described above for FcγRIIa (Example 6). Crystals were produced under several conditions as follows:

(a) 0.2M calcium acetate; 0.1M sodium cacodylate, pH6.5; 18% w/v polyethylene glycol (PEG) 8000;

(b) 0.1M sodium cacodylate, pH6.0 or pH5.5; 10% v/v 2-propanol; 20% w/v PEG 4000;
(c) 0.2M tri sodium citrate dihydrate; 0.1M sodium cacodylate pH6.5; 30% v/v 2-propanol.

The structure of the FcεRI crystals obtained by these experiments can be used in X-ray diffraction analysis and/or in molecular replacement and modeling strategies as described herein.

Example 10

This example describes the modeling of the three dimensional structure of the Fcγ receptor III (FcγRIIIb) in monomeric form.

The extracellular regions of the human Fc gamma receptor type III (FcγRIIIb) and the human Fc gamma Receptor type II a (FcγRIIa) show a sequence identity of about 53% (for 174 residues). The final sequence alignment used in this modeling work is shown in FIG. 18. The X-ray crystallographic structure of the human FcγRIIa was determined by the present inventors (Table 1) as described in Examples 1-7. The 3-dimensional coordinates of FcγRIIa in Table 1 differ from those used as the template to build a 3-dimensional model of the human FcγRIIIb by orientation of the imidazole ring of His 108 and one round of refinement.

MODELER (A. Sali and T. L. Blundell, J. Mol. Biol., vol. 234, 779-815 (1993)) as implemented in the InsightII-Homology software package (Insight II (97.0), MSI, San Diego) was used to generate 3-dimensional models of FcγRIIIb using a number of different initial sequence alignments and two structural templates of FcγRIIa. The structural template that was used was the 3-dimensional coordinates of FcγRIIa where, for the residues that had alternative side-chain conformations (residue numbers 10, 21, 33, 57, 60, 61, 65, and 89), the conformations labeled 'A' were selected. In each Modeler run 5 structural models of FcγRIIIb were generated. The following parameter values or options were used: 'library-schedule' of 1, 'max-var-iterations' of 300, 'md-level' of 'refine1', 'repeat-optimization' of 3, and 'max-molpdf' of 1e6. The best model from these runs had the sequence alignment given in FIG. 18, and used the structural template of Fc.RIIa, where residues 10, 21, 33, 57, 60, 61, 65, and 89 had side-chains in the 'A' conformation. The criteria for judging the 'best' model included the lowest value of the Modeler objective function (or −1.0×ln(Molecular probability density function=Mpdf)), 'well-behaved' PROSAII (M. Sippl, Proteins, vol. 17, 355-362 (1993)) residue energy plot for the model (for example, negative residue energy scores throughout the sequence), and 'well-behaved' PROFILES-3D (J. U. Bowie et al., Science, vol. 253, 164-170 (1991)) local 3D-1D compatibility score plot (for example, positive plot scores throughout the sequence).

Next, Modeler was used to generate 20 different structural models of FcγRIIIb using the sequence alignment and template selected above, and using the parameter values and options listed above. The model with the lowest −ln(Mpdf) value (i.e. 933.3) was then selected as the final structural model of the Fc RIIIb monomer, and the corresponding heavy (non-hydrogen) atom Cartesian coordinates are represented in Table 5. This structure was validated with the programs PROSAII, PROFILES-3D, and PROCHECK (R. M. Laskowski et al., J. Appl. Cryst. vol. 26, 283-291 (1993)).

The model of the 3-dimensional structure of FcγRIIIb monomer represented by the coordinates in Table 5 may be used as a basis for drug design in the same manner as that described for the crystallographic coordinates of FcγRIIa herein.

Example 11

Experimental

The following abbreviations and terms are used herein:

| | |
|---|---|
| rt | room temperature |
| Et₂0 | diethyl ether (i.e., ether or ethyl ether) |
| MS (APCI) | atmospheric pressure chemical ionization |
| THF | Tetrahydrofuran |
| EtOAc | Ethyl acetate |
| TMSCl | Trimethylsilyl chloride |
| CH₃CN | Acetonitrile |
| DMF | Dimethylformamide |

Experiment 1

This experiment illustrates a synthesis of 1,2-Bis(m-carboxyphenyl)ethane:

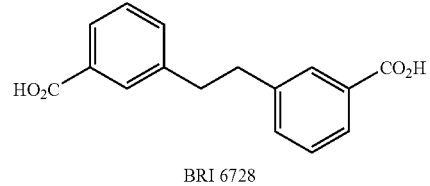

BRI 6728

Step 1: 1,2-Bis(m-bromophenyl)ethane was prepared by the method of Lindsay et al (JACS, 1961, 83, 943) as follows. Magnesium (0.05 g, 2.0 mmol) was added to a solution of 3-bromobenzylbromide (1.0 g, 4.0 mmol) in $Et_2O$ (10 mL) at rt. After 20 min at room temperature all the magnesium had dissolved and anhydrous ferric chloride (5 mg) was added. The reaction was heated to reflux for 1 hour, cooled, acidified to about pH 1 with 1 M aqueous $H_2SO_4$ and extracted with $Et_2O$ (3×50 mL). The combined organic extracts were washed with water (50 mL), dried ($Na_2SO_4$), filtered and concentrated in vacuo to give a yellow solid. Recrystallization from petroleum ether gave 1,2-bis(m-bromophenyl)ethane as a colorless solid. MS (APCI) m/z 338 (50%), 340 (100), 342 (50). $^1H$ NMR (200 MHz, $CDCl_3$): δ 2.85, s, 2H, 7.02-7.25, m, 2H, 7.30-7.39, m, 2H.

Step 2: tert-Butyl lithium (2.1 mL of 1.7 M solution in pentane, 3.60 mmol) was added dropwise to a solution of 1,2-bis(m-bromophenyl)ethane (305 mg, 0.90 mmol) in THF (10 mL) at −78° C. After 20 min at this temperature, $CO_2$ was bubbled through the reaction mixture while the cooling bath was removed and the reaction mixture reach rt. The reaction mixture was partitioned between water (50 mL) and $Et_2O$ (50 mL) and aqueous phase was separated and acidified to about pH 1 with concentrated aqueous HCl keeping the internal temperature below 25° C. The aqueous phase was extracted with EtOAc (3×50 mL) and the combined organic extracts dried ($Na_2SO_4$), filtered and concentrated in vacuo to give 1,2-bis(m-carboxyphenyl)ethane as a white solid. MS (APCI) m/z 269 (M+1, 100%) $^{13}C$ NMR (50 MHz, $d_6$-DMSO): δ 38.4, 128.8, 130.3, 131.1, 132.5, 134.8, 143.5, 169.2. The melting point agreed with that reported by Lindsay et al (JACS, 1961, 83, 943).

Experiment 2

This experiment illustrates a synthesis of 3-[(m-carboxyphenyl)methoxy]benzoic acid:

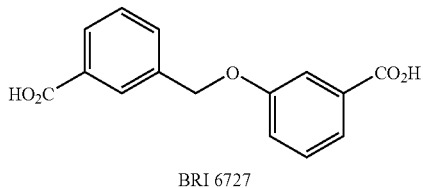

BRI 6727

Step 1: A mixture of 3-bromophenol (13.8 g, 80 mmol), 3-bromobenzyl bromide (10 g, 40 mmol), K$_2$CO$_3$ (16.6 g. 120 mmol) and 12 hours. The reaction mixture was cooled to rt, concentrated in vacuo and partitioned between Et$_2$O (300 mL) and water (300 mL). The organic phase was washed with aqueous NaOH (1 M, 300 mL), dried (Na$_2$SO$_4$), filtered and concentrated in vacuo to give 3-[(m-bromophenyl)methoxy]bromobenzene as a clear oil. MS (APCI) m/z 339 (M$^+$–3, 50%), 341 (M$^+$–1, 100%), 343 (M++3, 50%), $^{13}$C NMR (50 MHz, CDCl$_3$); δ 68.9, 113.4, 117.9, 122.5, 122.6, 124.1, 125.6, 129.9, 130.0, 130.4, 130.9, 138.4, 158.9.

Step 2: Using 3-[(m-bromophenyl)methoxy]bromobenzene and the method described in Example 1, step 2 gave 3-[(m-carboxyphenyl)methoxy]-benzoic acid as a white solid. MS (APCI) m/z 271 (M$^+$–1, 100%). $^{13}$C NMR (50 MHz, d$_6$-DMSO): δ 68.3, 114.5, 119.3, 121.5, 127.8, 128.3, 129.3, 130.5, 131.5, 131.8, 137.0, 157.7, 166.6, 166.7.

Experiment 3

This experiment illustrates a synthesis of 1,2-bis(3-phosphono-phenyl)ethane:

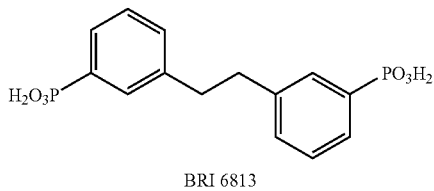

BRI 6813

Step 1: 1,2-Bis(3-bromophenyl)ethane (obtained using the method of Example 1, step 1) (440 mg., 1.29 mmol), diethyl phosphite (0.46 mL, 3.59 mL) and triethylamine (0.5 mL, 3.59 mmol) were dissolved in toluene and degassed. Pd(PPh$_3$)$_4$ (185 mg, 0.16 mmol) was added in one portion and the reaction heated to 90 C for 16 hours. The reaction was cooled to room temperature and purified by column chromatography (SiO$_2$, 50% EtOAc in petroleum ether →100% EtOAc →100% EtOH) to give 1,2-bis[3-(diethoxyphosphono)phenyl]-ethane as a white solid. MS (APCI) m/z 455 (M$^+$+1, 100%). $^{31}$p NMR (81 MHz, proton decoupled, CDCl$_3$): δ+19.5.

Step 2: Trimethylsilylbromide (1.03 mL, 7.8 mmol) was added dropwise to a solution of the above ester (586 mg, 1.30 mmol) in CH$_2$Cl$_2$ (10 mL) at rt. The reaction was stirred for 16 hours at room temperature and concentrated in vacuo. MeOH (5 mL) was added and the solution concentrated in vacuo. This procedure was repeated a further two times to give 1,2-bis(3-phosphonophenyl)ethane as a white solid. MS (APCI) m/z. 341 (M$^+$–1, 100%). $^{31}$P NMR (81 MHz, proton decoupled, CDCl$_3$): δ+14.6.

Experiment 4

This experiment illustrates a synthesis of 3,3'-Dicarboxychalcone:

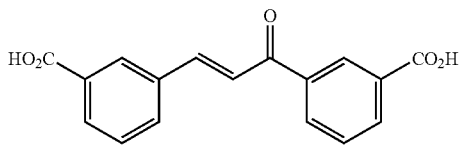

BRI 6734

Step 1: 3-Cyanobenzaldehyde (3.0 g, 23.0 mmol) and 3-cyanoacetophenone (3.34 g, 23.0 mmol) in glacial acetic acid (5 mL) and concentrated H$_2$SO$_4$ (3.66 mL, 69 mmol) was stirred at room temperature for 72 hours. Water (200 mL) was added and the reaction filtered. The precipitate was washed with water (2×200 mL) and dried in vacuo to give 3,3'-dicyanochalcone as an off-white solid. MS (APCI) m/z 258 (M$^+$–1, 100%). $^{13}$C NMR (50 MHz, d$_6$-DMSO): δ 111.7, 117.8, 118.0, 123.0, 129.7, 131.6, 132.1, 132.4, 133.3, 133.5, 135.3, 136.1, 137.4, 142.1, 187.3.

Step 2: A solution of 3,3'-dicyanochalcone from step 1 (2.0 g, 7.75 mmol) in glacial acetic acid (30 mL) was treated with a mixture of concentrated H$_2$SO$_4$ (10 mL) and water (10 mL). The reaction mixture was heated to 130 C for 12 hours, cooled to room temperature and filtered. The precipitate was washed with water (3×100 mL) and dried in vacuo to give 3,3'-dicarboxychalcone as a yellow solid. MS (APCI) m/z 295 (M$^+$–1, 100%). $^{13}$C NMR (50 MHz, d$_6$-DMSO); δ 122.5, 128.6, 128.7, 129.2, 130.8, 131.0, 131.2, 132.4, 132.5, 133.1, 134.5, 137.2, 143.1, 166.3, 166.5, 188.2

Experiment 5

This experiment illustrates a synthesis of 1,3-bis(m-carboxy-phenyl)-1-propanol:

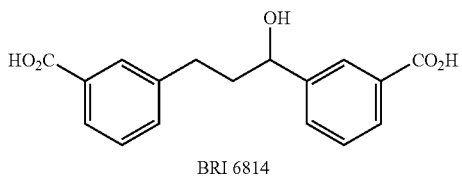

BRI 6814

3,3'-Dicarboxychalcone (Example 4, step 2) (430 mg, 1.45 mmol) in ethanol (10 mL) containing aqueous NaOH (1 M, 2.90 mmol) was hydrogenated at 45 psi for 48 hours in the presence of Wilkinson's catalyst (67 mg, 0.07 mmol). The reaction mixture was filtered and concentrated in vacuo. The residue was dissolved in methanol (10 mL) and treated with NaBH$_4$ (220 mg, 5.8 mmol) at rt. The reaction mixture was stirred for 16 hours at rt, quenched with the cautious addition of saturated aqueous NH$_4$Cl and partitioned between EtOAc (50 mL) and aqueous HCl (1 M, 50 mL). The organic extract was dried (Na$_2$SO$_4$), filtered and concentrated in vacuo to give 1,3-bis(m-carboxyphenyl)-1-propanol as a viscous oil. MS (APCI) m/z 299 (M$^+$–1, 100%). $^1$H NMR (200 MHz, CDCl$_3$); δ 1.95-2.10, m, 2H, 2.68-2.83, m, 2H, 4.62-4.78, m, 1H, 7.03-7.60, m, 4H, 7.75-8.03, m, 4H.

Experiment 6

This experiment illustrates a synthesis of trans-3,3'-bis-carboxystilbene:

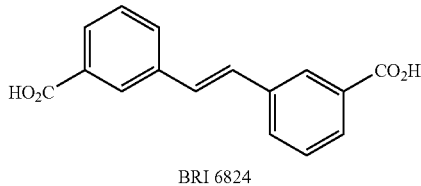

BRI 6824

Step 1: Methyl 3-bromobenzoate (21.5 g, 100 mmol), Pd(OAc)$_2$ (224 mg, 1 mmol), tri-o-tolylphosphine (608 mg, 2 mmol) and tributylamine (26.2 mL, 110 mmol) in DMF (100 mL) was degassed with argon and heated to 130 C for 6 hours while a stream of ethylene was bubbled through the solution. The reaction mixture was cooled to room temperature and filtered. The precipitated was washed with cold Et$_2$O (2×50 mL) and dried in vacuo to give trans-3,3'-bis-carboxystilbene dimethyl ester as an off-white solid. $^{13}$C NMR (50 MHz, CDCl$_3$): δ 52.2, 127.5, 128.8, 130.6, 130.9, 137.2, 166.9.

Step 2: The above diester (500 mg, 1.7 mmol) in the THF (10 mL) was treated at room temperature with aqueous LiOH (1 M, 10 mL). After stirring for 16 hours at rt, the reaction mixture was partitioned between Et$_2$O (50 mL) and water (50 mL). The aqueous phase was separated and the organic phase was extracted with water (25 mL). The combined aqueous extracts were acidified with concentrated aqueous HCl while maintaining the internal temperature below 10 C. The aqueous phase was extracted with CH$_2$Cl$_2$ (3×50 mL) and the combined organic extracts dried (Na$_2$SO$_4$), filtered and concentrated in vacuo to give trans-3,3'-Biscarboxystilbene as a white solid. MS (APCI) m/z 267 (M$^+$–1, 100%). $^1$H NMR (200 MHz, d$_6$-DMSO): δ 7.28-7.56, m, 2H, 7.78-7.90, m, 2H, 8.20, s, 1H.

Experiment 7

This experiment illustrates a synthesis of (S,S)-1,2-bis-(3-carboxyphenyl)ethane-1,2-diol:

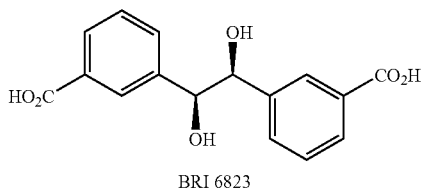

BRI 6823

Step 1: trans-3,3'-Biscarboxystilbene dimethyl ester (Example 6, step 1) (5.0 g, 16.9 mmol) and N-methylmorpholine-N-oxide (2.2 g, 18.6 mmol) in acetone (50 mL) and water (20 mL) were treated at room temperature with an aqueous solution of OsO$_4$ (4.3 mL, 39.4 mM, 0.17 mmol). The reaction mixture was stirred for 16 hours at rt, quenched by addition of sodium metabisulfite (3.0 g) and the pH adjusted to about pH 7 with 2 M aqueous sulfuric acid. The acetone was removed in vacuo and the remaining solution acidified to about pH 2, saturated with NaCl and extracted with EtOAc (3×100 mL). The combined organic extracts were dried (Na$_2$SO$_4$), filtered and concentrated in vacuo to give (R,R)-1,2-bis-[3-(carbomethoxy)-phenyl]ethane-1,2-diol as a white solid. $^1$H NMR (200 MHz, CDCl$_3$): δ 3.2, bs, 1H, 3.82, s, 3H, 4.77, s, 1H, 7.20-7.31, m, 2H, 7.80-7.89, m, 2H.

Step 2: The above diester (500 mg, 1.5 mmol) was hydrolyzed using the procedure described in Example 6, step 2 to give (S,S)-1,2-bis-(3-carboxyphenyl)ethane-1,2-diol as a white solid. MS (APCI) m/z 301 (M$^+$–1,100%). $^1$H NMR (200 MHz, d$_6$-DMSO): δ 3.40, bs, 1H, 4.76, s, 1H, 5.56, bs, 1H, 7.20-7.29, m, 2H, 7.80-7.91, m, 2H.

Experiment 8

This experiment illustrates a synthesis of 3,3'-bis-(carboxy-methyl) stilbene:

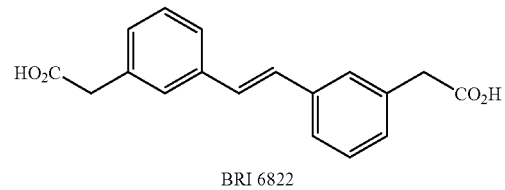

BRI 6822

Step 1: Methyl 3-bromophenylacetate (8.0 g, 34.9 mmol) was reacted with ethylene using the procedure described in Example 6, step 1. The crude reaction product was purified by column chromatography (SiO$_2$, 5% EtOAc in petroleum ether) to give 3,3'-bis-[(carbo-methoxy)methyl]stilbene and methyl 3-(ethenyl)phenyl-acetate as a white solid mixture.

3,3'-Bis-[(carbo-methoxy)methyl]stilbene: $^1$H NMR (200 MHz, CDCl$_3$): δ 3.65, s, 2H, 3.70, s, 3H, 7.1, s, 1H, 7.15-7.50, m, 4H. $^{13}$C NMR (50 MHz, CDCl$_3$): δ 41.2, 52.1, 125.3, 127.4, 128.6, 128.7, 128.9, 134.4, 137.6, 171.9

Methyl 3-(ethenyl)phenylacetate: $^1$H NMR (200 MHz, CDCl$_3$): δ 3.63, s, 2H,; 3.68, s, 3H, 5.28, d, J=10.9 Hz, 1H, 5.78, d, J=18.8 Hz, 1H, 6.72, d, J=10.9, 18.8 Hz, 1H, 7.18-7.41, m, 4H Step 2: 3,3'-Bis-[(carbomethoxy)methyl]stilbene was hydrolyzed using the procedure described in Example 6, step 2 to give 3,3'-bis-[(carboxy)methyl]stilbene as a white solid. MS (APCI) m/z 295 (M$^+$–1, 100%). $^1$H NMR (200 MHz, d$_6$-DMSO): δ 3.60, s, 2H, 7.00-7.62, m, 5H.

Experiment 9

This experiment illustrates a synthesis of 1,2-bis-[m-(carboxymethyl)phenyl]ethane:

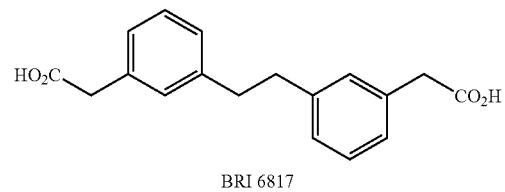

BRI 6817

Step 1: 3,3'-Bis-[(carbomethoxy)methyl]stibene (Example 8, step 1) (500 mg, 1.5 mmol) and palladium on carbon (10%, 200 mg) in methanol (20 mL) was hydrogenated under an atmosphere of hydrogen for 16 hours at rt. The reaction was filtered and concentrated in vacuo to give 1,2-bis-[m-(carbomethoxymethyl)phenyl]ethane as a colorless oil. $^1$H NMR (200 MHz, CDCl$_3$): δ 2.91, s, 2H, 3.63, s, 2H, 3.72, s, 3H, 7.08-7.31, m, 4H.

Step 2: The above ester was hydrolyzed using the procedure described in Example 6, step 2 to give 1,2-bis-]$_m$-(carboxymethyl] ethane as a white solid. MS (APCI) m/z 297 (M$^+$–1, 100%). $^1$H NMR (200 MHz, d$_6$-DMSO): δ 2.82, s, 2H, 3.56, s, 2H, 7.06-7.06-7.27, m, 4H, 12.25, bs, 1H.

Experiment 10

This experiment illustrates a synthesis of 1-[m-(carboxymethyl)phenyl]-2-[m-(carboxyhenyl)]ethane:

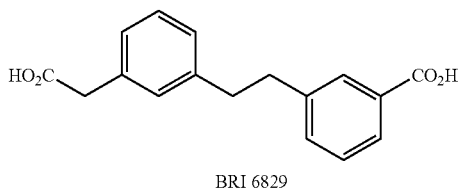

BRI 6829

Step 1: Methyl 3-(ethenyl)phenylacetate (Example 8, step 1) (1.1 g, 6.25 mmol), methyl 3-bromobenzoate (960 mg, 4.46 mmol), palladium acetate (20 mg, 0.09 mmol), N,N-dimethylglycine hydrochloride (249 mg, 1.78 mmol) and sodium acetate (731 mg, 8.92 mmol) were dissolved in N-methylpyrrolidinone, degassed with argon and heated to 130 C for 5 hours. The reaction was cooled to rt, diluted with EtOAc (100 mL) and the organic phase washed with water (100 mL), aqueous HCl (1 M, 100 mL) and saturated aqueous NaHCO$_3$ (100 mL). The organic extracts were dried (Na$_2$SO$_4$), filtered and concentrated in vacuo to give trans-1-[m-(3-carbomethoxymethyl)-phenyl]-2-[3-(carbomethoxy-phenyl)]ethane as a colorless oil. MS (APCI) m/z 309 (M$^+$-1, 100%). $^1$H NMR (200 MHz, CDCl$_3$): δ 3.64, s, 2H, 3.68, s, 3H, 7.16-7.56, 6H, 7.63-7.71, m, 1H, 7.90-7.98, m, 1H, 8.20, m, 1H.

Step 2: The above compound was hydrogenated according to the method described in Example 9, step 1 to give 1-[m-(carbomethoxymethyl)-phenyl]-2-[m-(carbomethoxyphenyl)]ethane as a colorless oil. $^1$H NMR (200 MHz, CDCl$_3$): δ 2.87, m, 4H, 3.56 s, 2H; 3.60, s, 3H, 3.84, s, 3H, 6.95-7.36, 6H, 7.77-7.90, m, 2H.

Step 3: The ester in Step 2 was hydrolyzed using the procedure described in Example 6, step 2 to give 1-[m-(carboxymethyl)phenyl]-2-[m-(carboxyphenyl)]ethane as a white solid. MS (APCI) m/z 283 (M$^+$-1, 100%). $^1$H NMR (200 MHz, d$_6$-DMSO) δ 2.92, m, 4H, 3.55, s, 2H, 7.02-7.35, m, 4H, 7.36-7.60, m, 2H; 7.71-7.93, m, 2H. $^{13}$C NMR (50 MHz, d$_6$-DMSO): δ 38.6, 38.7, 40.9, 128.5, 128.8, 130.0, 130.3, 131.0 131.2, 132.6, 134.8, 136.7, 143.1, 143.8, 169.2, 174.5.

Experiment 11

This experiment illustrates a synthesis of N,N-bis(m-carboxybenzyl)glycine:

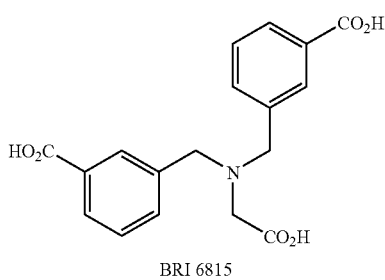

BRI 6815

Step 1: m-Cyanobenzyl bromide (2.35 g, 12.0 mmol) was slowly added to a solution of glycine methyl ester hydrochloride (0.63 g, 5.0 mmol), NaHCO$_3$ (1.4 g, 17.0 mmol) and NaI (0.37 g, 2.4 mmol) in DMSO (5 mL) and THF (20 mL). The reaction was heated to reflux for 2 hours, cooled to room temperature and diluted with EtOAc (50 ml) and water (40 mL). The organic phase was washed with water (3×40 mL), saturated aqueous NaCl (40 mL), dried (Na$_2$SO$_4$), filtered and concentrated in vacuo to give N,N-Bis(m-cyanobenzyl)glycine methyl ester as a colorless oil of sufficient purity for subsequent reactions. Additional purification can be achieved by extraction into dilute aqueous acid, basification and extraction in an organic solvent. $^1$H NMR (200 MHz, CDCl$_3$): δ 3.39, s, 2H, 3.71, s, 3H, 3.86, s, 4H, 7.39-7.73, m, 10H.

Step 2: The above nitrile (1.5 g, 5.02 mmol) was hydrolyzed according to the method described in Example 4, step 2 to give N,N-bis(m-carboxybenzyl)glycine (sulfate salt) as an off-white solid. MS (APCI) m/z 342 (M$^+$-1, 100%). $^{13}$C NMR (50 MHz, d$_4$-MeOH): δ 53.8, 59.0, 130.2, 131.5, 132.7, 132.8, 134.2, 136.1, 169.1, 170.7.

Experiment 12

This experiment illustrates a synthesis of (3R,4R)-1,3-bis-(p-methoxybenzyl)-4,5-bis(m-phosphonophenyl)-imidazolid-2-one:

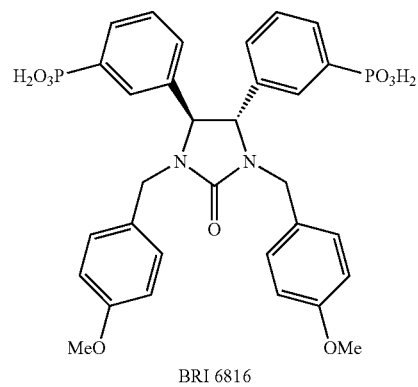

BRI 6816

Step 1: p-Methoxybenzylamine (7.42 g, 54 mmol) in CH$_2$Cl$_2$ (100 mL) containing anhydrous MgSO$_4$ was treated with m-bromobenzaldehyde (10.0 g, 54 mmol) at OC. The reaction was allowed to stir at room temperature for 16 hours, filtered and concentrated in vacuo to give N-p-methoxybenzyl imine of m-bromobenzaldehyde as a colorless oil. $^1$H NMR (200 MHz, CDCl$_3$): δ 3.82, s, 3H, 4.78, s, 2H, 6.92, d, J=7.5 Hz, 2H, 7.16, d, J=7.5 Hz, 2H;.7.52-7.60, m, 1H, 7.62-7.72, m, 1H, 7.98, m, 1H, 8.29, m, 1H.

Step 2: 1,2-Dibromoethane (0.5 mL) was added to zinc (1.31 g, 20.0 mmol) in CH$_3$CN (5 mL) and the mixture heated to reflux for 1 minute. Once the reaction had cooled to rt, TMSCl (1 mL) was added and the reaction stirred at room temperature for 1 hour. The above imine (6.08 g, 20 mmol) in CH$_3$CN (20 mL) was added in one portion, followed by TMSCl (3.8 mL) over 30 mins. The reaction was then stirred for 4 hours at 35-40 C. The reaction was quenched with aqueous NH$_4$OH (6 mL) and saturated aqueous NH$_4$Cl (14 mL) and filtered. The aqueous phase was separated and the aqueous phase extracted with Et$_2$O (50 mL). The combined organic extracts were dried (Na$_2$SO$_4$), filtered and concentrated in vacuo to give an orange oil. Column chromatography (SiO$_2$, 25% Et$_2$O in petroleum ether) gave (1R,2R)—N,N'-(p-methoxybenzyl)-1,2-(m-bromophenyl)ethane-1,2-diamine as a colorless oil. $^{13}$C NMR (50 MHz, CDCl$_3$): δ 50.5, 55.3, 67.4, 113.8, 122.4, 126.7, 129.2, 129.6, 130.3, 130.7, 132.1, 143.4, 158.7.

Step 3: N,N'-Disuccinimidyl carbonate (160 mg, 0.64 mmol) was added to a solution of the above diamine (260 mg, 0.43 mmol) in CH$_3$CN (10 mL). The reaction was heated to reflux for 2 hours. A further charge of N,N'-disuccinimidyl carbonate (160 mg, 0.64 mmol) was added and the reaction heated to reflux for a further 2 hours. The reaction was concentrated and partitioned between EtOAc (40 mL) and aqueous HCl (1 M, 40 mL). The organic phase was washed with saturated aqueous NaHCO$_3$ (40 mL), saturated NaCl (40 mL), dried (Na$_2$SO$_4$), filtered and concentrated in vacuo to give an orange oil. Column chromatography (SiO$_2$, 25% Et$_2$O in petroleum ether→EtOAc) gave (3R,4R)-1,3-bis-(p-methoxybenzyl)-4,5-bis(m-bromophenyl)-imidazolid-2-one as a white solid. $^{13}$C NMR (50 MHz, CDCl$_3$): δ 45.3, 55.2, 65.0, 111.4, 123.1, 125.9, 128.1, 129.8, 130.2, 130.5, 131.7, 140.7, 159.1, 159.9.

Step 4: The above urea (200 mg, 0.31 mmol) was treated with diethyl phosphite under the conditions described in Example 3, step 1 to give (3R,4R)-1,3-bis-(p-methoxybenzyl)-4,5-bis[m-(diethoxy-phosphono)phenyl]-imidazolid-2-one as a colorless oil. MS (APCI) m/z 750 (M$^+$+1, 100%). $^{31}$P NMR (81 MHz, proton decoupled, CDCl$_3$): δ+18.4.

Step 5: The above phosphonate (340 mg, 0.45 mmol) was treated with trimethylsilyl bromide under the conditions described in Example 3, step 2 to give (3R,4R)-1,3-bis-(p-methoxybenzyl)-4,5-bis(m-phosphonophenyl)-imidazolid-2-one as an off white solid. $^{31}$P NMR (81 MHz, proton decoupled, CDCl$_3$): δ+11.5.

Experiment 13

This experiment illustrates a synthesis of 6-amino-4-(4'-pyridyl)-2-(1H)-pyridone:

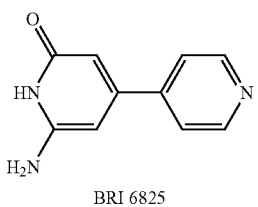

BRI 6825

Step 1: Reaction of 4,4'-bipyridine with NaNH$_2$ according to JOC, 1997, 62, 2774 gave, in addition to the reported 2,2'-diamino-4,4'-bipyridine, the previously unreported 2-amino-4,4'-bipyridine. $^{13}$C NMR (50 MHz, d$_6$-DMSO): δ 105.0, 109.5, 120.9, 145.4, 148.9, 150.3, 160.5.

Step 2: The above amino-pyridine (1.5 g, 10.5 mmol) was dissolved in acetic anhydride (20 mL) and heated to 60 C for 3 hours. The reaction was cooled to room temperature and filtered. The solid was washed with Et$_2$O (2×50 mL) and dried in vacuo to give 2-(acetylamino)-4-(4'-pyridyl)-pyridine as a light brown solid. $^1$H NMR (200 MHz, d$_6$-DMSO): δ 2.12, s, 3H, 7.40-7.58, m, 1H; 7.60-7.83, m, 2H, 8.30-8.58, m, 2H, 8.62-8.88, m, 2H.

Step 3: The above pyridine (0.9 g, 4.2 mmol) was dissolved in CH$_2$Cl$_2$ (50 mL) and treated with m-chloroperbenzoic acid (4.86 g, 60% wt) and the reaction heated to reflux for 16 hours. The reaction was cooled to rt, filtered and the precipitate was washed with Et$_2$O (2×50 mL). The precipitate was added to acetic anhydride (25 mL) and heated to reflux for 4 hours, cooled to room temperature and the precipitate collected. The precipitate was added to methanol (5 mL) and treated with Na$_2$CO$_3$ (50 mg) and heated to reflux for 5 hours. The reaction was cooled to rt, filtered and the filtrate concentrated in vacuo. Trituration with Et$_2$O gave 6-amino-4-(4'-pyridyl)-2-(1H)-pyridone as a yellow solid. MS (CI) m/z 188 (M$^+$+1, 100%). $^1$H NMR (200 MHz, d$_4$-MeOH): δ 5.83, d, J=1 Hz, 1H, 5.90, d, J=1 Hz, 1H, 7.67, d, J=7 Hz, 2H; 8.16, d, J=7 Hz, 2H.

Experiment 14

This experiment illustrates Fc receptor modulating activity of some of the compounds of the present invention.

The interaction between recombinant soluble FcγRIIa and human immunoglobulin in the presence of small compounds shown in FIGS. 23A and 23B were investigated using a BIAcore 2000 biosensor (Pharmacia Biotech, Uppsala, Sweden) at 22 C in Hepes buffered saline [HBS: 10 mM Hepes (pH 7.4), 150 mM NaCl, 3.4 mM EDTA, 0.005% Surfactant P20 (Pharmacia)]. Monomeric human IgG1, IgG3, and IgE (50 µg/mL) (non-specific binding control) were covalently coupled to the carboxymethylated dextran surface of the CM-5 sensor-chip (BIAcore, Uppsala, Sweden) using the amine coupling protocol (BIAcore, Uppsala, Sweden). An additional channel was chemically treated using the coupling protocol. Recombinant soluble FcγRIIa was used as a concentration of 125 µg/mL which was equivalent to 50% binding capacity. Recombinant soluble FcγRIIa was preincubated with each of the compounds at room temperature for 30 minutes before being injected over the sensor-chip surface for 1 minute at 10 µL/min followed by a 3 minute dissociation phase. All surfaces were regenerated with 50 mM diethylamine (about pH 11.5), 1 M NaCl between each of the compounds being analyzed. The maximum response for each interaction was measured. Non-specific binding responses (IgE channel) were subtracted from binding to IgG1 and IgG3. Measurements were corrected for differences in buffer composition between the compounds and receptor.

Figure 24:
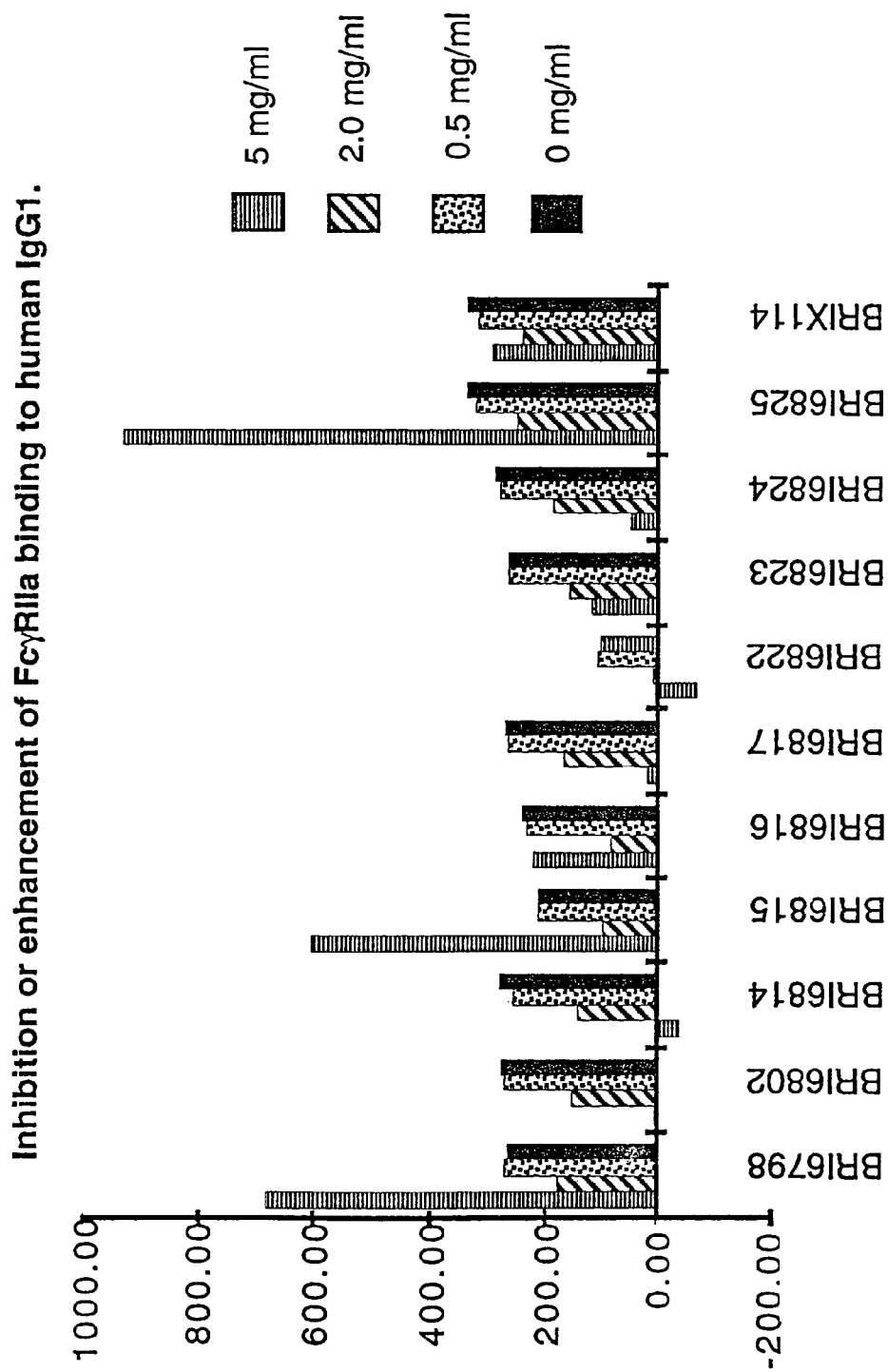
Figure 25:
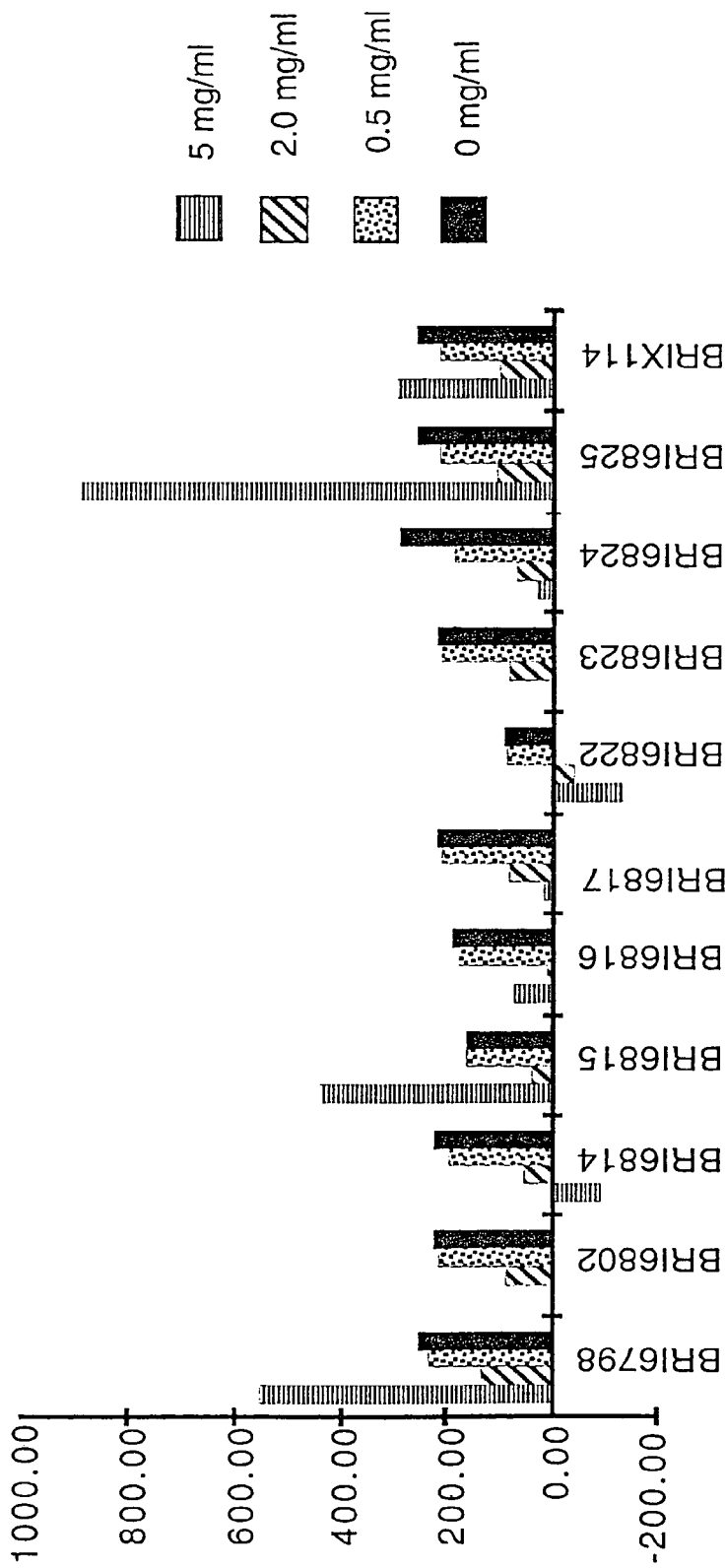
Figure 26:
Figure 27:
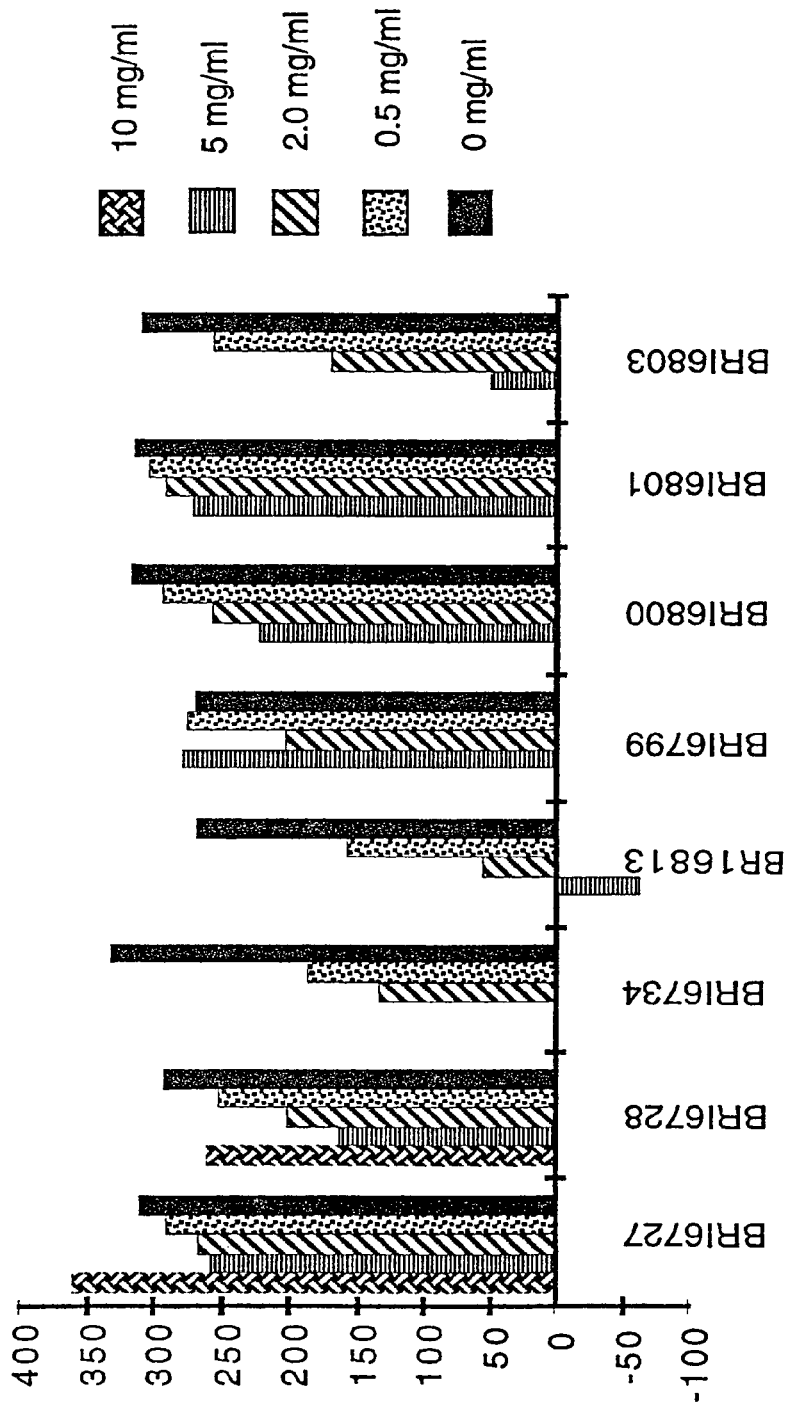

Using the sensitivity of surface plasmon resonance the interaction of IgG1 (FIGS. 24 and 26) and IgG3 (FIGS. 25 and 27) with soluble FcγRIIa in the presence of compounds was measured. Compounds BRI6728, BRI6734, BRI6813, BRI6800, BRI6801, BRI6802, BRI6803, BRI6814, BRI6817, BRI6822, BRI6823, and BRI6824 all inhibited the interaction of soluble FcγRIIa with IgG1 (25 and 27). At concentrations of 5 mg/mL, compounds BRI6798, BRI6799, BRI6815, and BRI6825 enhanced the interaction between soluble FcγRIIa with IgG1 (FIGS. 24 and 26). Compounds BRI6728, BRI6734, BRI6813, BRI6800, BRI6801, BRI6802, BRI6803, BRI6814, BRI6816, BRI6817, BRI6822, BRI6823 and BRI6824 inhibited the interaction of soluble FcγRIIa with IgG3 (FIGS. 25 and 27). Compounds BRI6727, BRI6798, BRI6815 and BRI6825 all enhanced the interaction between soluble FcγRIIa with IgG3 at concentration of about 5 mg/mL and 10 mg/mL.

Experiment 15

This experiment illustrates a synthesis of N-(3'-carboxyphenyl)-2-(carboxybenzene)sulfonamide:

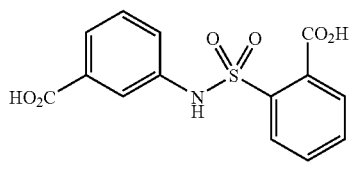

BRI 6855

Step 1: Methyl 2-(chlorosulfonyl)-benzoate (2.25 g, 8.73 mmol) in methylene chloride (20 mL) was added dropwise to a solution of ethyl 3-aminobenzoate (1.44 g, 8.73 mmol) and triethylamine (1.21 mL, 8.73 mmol) in methylene chloride (10 mL) at 0 C. The reaction was allowed to warm to room temperature and stirred overnight. The reaction mixture was washed with water (20 mL), aqueous HCl (1 M, 20 mL) and aqueous NaOH (1 M, 20 mL), dried (MgSO$_4$, filtered and concentrated in vacuo to give an orange oil. Trituration with ethyl ether gave N-(3'-carboethoxyphenyl)-2-(carbomethoxy)benzenesulfonamide as white solid. $^1$H NMR (200 MHz, CDCl$_3$): δ 1.31, t, J=6.0 Hz, 3H, 4.00, s, 3H, 4.29, q, J=6.0 Hz, 2H, 7.23-7.61, m, 5H, 7.66-7.92, m, 3H, 8.26, br s, 1H.

Step 2: The above diester (1.0 g, 2.75 mmol) was hydrolyzed using the procedure described in Example 6, step 2 to provide N-(3'-carboxyphenyl)-2-(carboxybenzene)sulfonamide as a white solid. MS (CI) m/z 320 (M$^+$−1, 100%). $^{13}$C NMR (50 MHz, d$_6$-DMSO): δ 168.0, 166.3, 137.3, 135.8, 133.4, 132.6, 131.3, 130.1, 129.0, 128.8, 128.0, 124.5, 123.8 and 120.5.

Experiment 16

This experiment illustrates a synthesis of trans-3,3'-bis-(N-hydroxyamidino) stilbene:

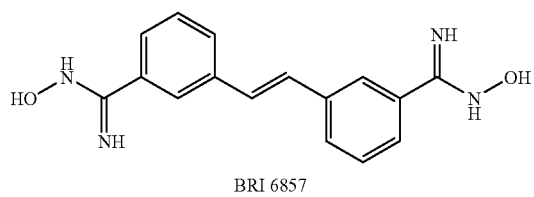

BRI 6857

Step 1: Trans-3,3'dicyanostilbene was prepared from 3-bromobenzonitrile using the method of Example 6, Step 1. MS(CI) m/z 230 (M+, 100%).

Step 2. Trans-3,3'-dicyanostilbene (1.5 g, 6.52 mmol), hydroxylamine hydrochloride (3.26 g, 50 mmol) and Na$_2$CO$_3$ (3.04 g, 30 mmol) in EtOH (40 mL) and water (15 mL) was heated to reflux for 3 h. The reaction was cooled to room temperature and the ethanol was removed in vacuo. The remaining solution was extracted with EtOAc (2×50 mL) and the combined organic extracts was washed with aqueous HCl (1 M, 2×20 mL). The combined aqueous extracts were made basic and extracted with EtOAc (3×50 mL). The combined organic extracts were dried (MgSO$_4$), filtered and concentrated in vacuo to give a colorless solid. MS(CI) m/z 297 (M$^+$+1, 100%). $^{13}$C NMR (50 MHz, d$_6$-DMSO): δ 123.3, 124.8, 127.1, 128.6, 133.8, 136.8 and 150.7.

Experiment 17

This experiment illustrates a synthesis of (d,l)-and meso-2-acetylamino-3-(3-{2-[3-(2-acetylamino-2-carboxyethyl)phenyl]ethyl}-phenyl) propionic acid:

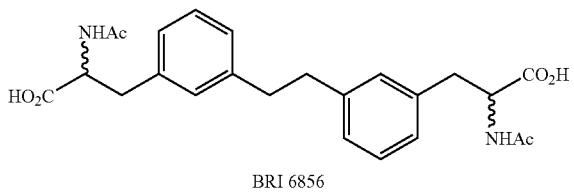

BRI 6856

Step 1: 3-Bromobenzaldehyde (23.7 g, 128.2 mmol), N-acetyl glycine (10.0 g, 85.5 mmol) and sodium acetate (5.26 g, 64.1 mmol) in acetic anhydride (60 mL) was heated to reflux for 1 h. The reaction was cooled to room temperature and water (100 mL) was added. The resulting suspension was filtered and the solid was washed with water (2×50 mL). The remaining solid was dissolved in methylene chloride (100 mL), dried (MgSO$_4$), filtered and concentrated in vacuo to give a yellow solid. The solid was suspended in dry MeOH (200 mL) and heated to reflux for 9 h. The reaction mixture was concentrated in vacuo to give a yellow solid. Recrystallization from EtOAc and petroleum ether gave methyl m-bromo-α-acetamidocinnamate as a yellow solid. MS (CI) m/z 298 (M$^+$+1 (Br=79), 100%), 300 (M$^+$+1 (Br=81), 100%). $^{13}$C NMR (50 MHz, d$_6$-DMSO): 6.23.3, 52.8, 122.5, 125.0, 128.06, 130.0, 130.2, 132.2, 132.3, 135.9, 165.4 and 168.8.

Step 2: Trans-methyl 2-acetylamino-3-(3-{2-[3-trans-(trans-2-acetylamino-2-carbomethoxyethenyl)phenyl]ethenyl}phenyl)prop-2-enoate was prepared from the above compound using the method of Example 6, step 1. MS (CI) m/z 461 (M$^+$−1,100%).

Step 3: The compound from step 2 (380 mg, 0.82 mmol) and Pd/C (300 mg, 10%) in MeOH (20 mL) was stirred under a hydrogen atmosphere at room temperature for 16 h. The reaction was filtered and concentrated in vacuo to give (d,l)- and meso-methyl 2-acetylamino-3-(3-{2-[3-(2-acetylamino-2-carbomethoxy-ethyl)-phenyl]-ethyl}-phenyl)-propanoate as a clear viscous oil which was used without further purification.

Step 4: The compound from step 3 (280 mg, 0.60 mmol) was hydrolyzed using the procedure described in Example 6, step 2 to give (d,l)-and meso-2-acetylamino-3-(3-{2-[3-(2-acetylamino-2-carboxyethyl)phenyl]ethyl}-phenyl) propionic acid as a clear viscous oil. MS (CI) m/z 440 (M$^+$−1, 100%).

Experiment 18

This experiment illustrates a synthesis of (3R,4R)-4,5-bis (m-carboxyphenyl)imidazolid-2-one:

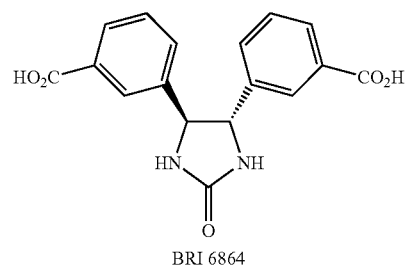

BRI 6864

Step 1: Methanesulfonyl chloride (1.01 mL, 13.1 mmol) was added dropwise to a solution of (R,R)-1,2-bis-[3-(carbomethoxy)phenyl]ethane-1,2-diol (Example 7, step 1) (1.5 g, 4.54 mmol) in pyridine (10 mL) at 0 C. The reaction was allowed to warm to room temperature and stirred overnight. The reaction was diluted with water (30 mL) and 30 mL of methylene chloride and the aqueous phase was extracted with 2×10 mL of methylene chloride. The combined organic extracts were washed with 2×20 mL of 1 M aqueous HCl, 20 mL of aqueous sodium bicarbonate, dried over magnesium sulfate, filtered and concentrated in vacuo to give di-methanesulfonate of (R,R)-1,2-bis-[3-(carbomethoxy)phenyl]ethane-1,2-diol as a yellow viscous oil.

Step 2: A solution of the above mesylate (505 mg, 1.0 mmol) and NaN$_3$ (150 mg, 2.31 mmol) in 6 mL of DMF was heated to 90 C for 17 h. The reaction mixture was cooled to rt, diluted with 50 mL of diethyl ether and washed with 3×50 mL of water. The organic phase was dried over MgSO$_4$, filtered and concentrated in vacuo to give (R,R)-1,2-bis-3-(carbomethoxy)phenyl]-1,2-diazo-ethane as a yellow viscous oil. $^1$H NMR (200 MHz, CDCl$_3$): δ3.93, s, 3H, 4.73, s, 1H, 7.17-7.39, m, 2H, 7.78-8.01, m, 2H.

Step 3: The above diazide (611 mg, 1.61 mmol) and Pd on carbon (10%, 50 mg) in methanol was treated with concentrated aqueous HCl (3.86 μL, 3.86 mmol). The reaction was placed under a hydrogen atmosphere and stirred at room temperature for 30 h. The reaction was filtered through celite and concentrated to give the hydrochloride salt of (R,R)-1,2-bis-[3-(carbomethoxy)phenyl]-1,2-diamino-ethane. MS (CI) m/z 329 (M$^+$+1 for the free amine, 70%), 312 (100%).

Step 4: The above diamine (in free base form) (280 mg, 0.85 mmol) in 5 mL of acetonitrile was treated with DMAP (104 mg, 0.85 mmol) a solution of di-tert-butyl dicarbonate (204 mg, 0.94 mmol) in 1 mL of acetonitrile at rt. The reaction methoxy]bromo-benzene (Example 2, step 1) (233 mg, 0.68 mmol) in 6 mL of THF at −78 C. After 20 min at this temperature, the solution was added dropwise to a solution of ethyl trifluoroacetate (0.35 mL, 2.94 mL) in 5 mL of THF at −78 C. The reaction mixture was stirred for 16 h during which time the reaction mixture reached rt. The reaction mixture was partitioned between 20 mL of 1 M HCl and 50 mL of ether. The organic phase was separated, dried over sodium sulfate, filtered and concentrated in vacuo to provide 3-([3'-(1"-oxo-2",2",2"-trifluoroethyl)phenoxy]methyl)phenyl trifluoromethyl ketone as a colorless oil. MS (CI) m/z 377 (M$^+$+1, 100%), $^{19}$F NMR (188 MHz, CDCl$_3$): δ −71.76 and −71.90.

Experiment 20

This experiment illustrates a synthesis of Ac-Phe-Gln-Asn-Gly-Lys-Ser-NH$_2$:

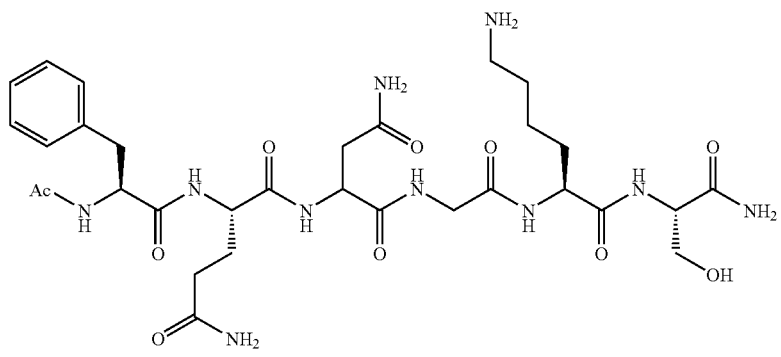

BRI 6868 was stirred for 25 min at room temperature and partitioned between 50 mL of ether and 50 mL of 1 M HCl. The organic phase was separated, dried over sodium sulfate, filtered and concentrated in vacuo. Column chromatography gave (3R, 4R)-4,5-bis-(m-carbomethoxyphenyl)imidazolid-2-one as a white solid. MS (APCI) m/z 355 (M$^+$+1, 100%). $^1$H NMR (200 MHz, d$_6$-DMSO): δ 3.86, s, 6H; 4.57, s, 2H, 7.16, br s, 2H, 7.46-7.61, m, 4H, 7.88-8.00, m, 4H.

Step 5: The above diester (68 mg, 0.19 mmol) was hydrolyzed using the procedure described in Example 6, step 2 to give (3R,4R)-4,5-bis(m-carboxyphenyl)imidazolid-2-one as a white solid. MS (electrospray) m/z 327 (M$^+$+1, 100%). $^{13}$C NMR (50 MHz, d$_6$-DMSO) δ 64.3, 127.4, 129.1, 129.3, 131.1, 131.4, 142.1, 162.5, 167.3.

Experiment 19

This experiment illustrates a synthesis of 3-([3'-(1"-oxo-2",2",2"-trifluoroethyl)phenoxy]methyl)phenyl trifluoromethyl ketone:

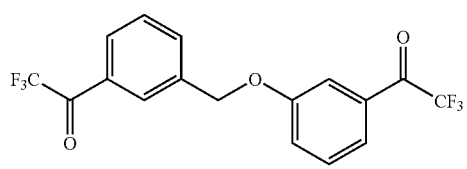

BRI 6865

Tert-butyl lithium (1.6 mL, 1.7 M in pentane, 2.72 mmol) was added dropwise to a solution of 3-[(m-bromophenyl)

The peptide was assembled using solid phase peptide synthesis techniques. N-Acylation and cleavage from the resin gave the title compound as a while sold. HPLC and MS analysis confirmed the purity and identity of this material.

Experiment 21

This experiment illustrates a synthesis of Cyclo-[N-Phenylglycine-Gln-Asn-(D)-Asp]-Lys-Ser-NH$_2$:

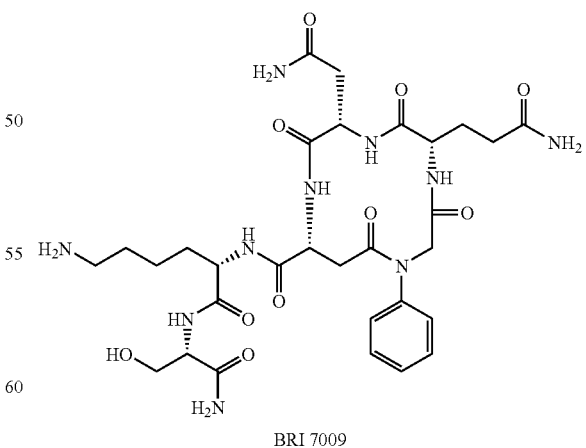

BRI 7009

Step 1: N-[(4S)-3-benzyloxycarbonyl-5-oxo-oxazolidin-4-yl-acetyl chloride (3.00 g, 10 mmol) in dichloromethane (20 mL) was added dropwise to a solution of tert-butyl-N-phenylglycinate (2.3 mg, II mmol) in pyridine (10 mL) at 0 C. The reaction was allowed to warm to room temperature and stirred overnight. The reaction was diluted with H₂O (100 mL) and EtOAc (150 mL). The organic phase was separated and washed successively with citric acid (10%, 2×100 mL) and brine (100 mL), dried (MgSO₄), filtered and concentrated in vacuo to give a yellow viscous oil. Column chromatography (SiO₂, 20-50% EtOAc in petroleum ether) gave tert-butyl N-[(4S)-3-benzyloxycarbonyl-5-oxo-oxazolidin-4-yl-acetyl]-N-phenylglycinate as a white foam. MS (APCI) m/z 467 (M⁺−1,100%).

Step 2: Aqueous NaOH (3 mL, 1 M, 3 mmol) was added dropwise to a solution of the above dipeptide (570 mg, 1.22 mmol) in methanol (20 mL) at 0 C. The reaction was allowed to warm to room temperature and monitored by TLC. The reaction was concentrated and partitioned between Et₂O (30 mL) and citric acid (10%, 30 mL) at 0 C. The aqueous phase was extracted with Et₂O (3×30 mL), and the combined organic extracts were dried (MgSO₄), filtered and concentrated in vacuo to give a white solid. Column chromatography (SiO₂, 2-5%, MeOH in dichloromethane) gave tert-butyl N-[(2S)-N-benzyloxycarbonyl-aspartyl]-β-N-phenylglycinate as a white solid. MS (APCI) m/z 456 (M⁺+1, 90%).

Step 3: The above compound (1.35 g. 2.96 mol) in MeOH (40 mL) containing palladium on carbon (10%, 500 mg) was placed under an atmosphere of hydrogen and stirred at room temperature for 16 hours. The reaction was filtered and concentrated in vacuo to give tert-butyl N-[(2S)-asparty])-β-N-phenylglycinate as an off white solid.

Step 4: The above compound (890 mg, 2.76 mmol), Fmoc-O-Su, i.e., N-(9-fluorenylmethoxycarbonyloxy) succinimide, (932 mg, 2.76 mmol), Na₂CO₃ (880 mg, 8.29 mmol) in dioxane (15 mL) and H₂O (15 mL) was stirred at room temperature for 16 hours. The reaction was diluted with Et₂O (100 mL) and H₂O (100 mL). The organic layer was separated and extracted with aqueous Na₂CO₃ (5%, 3×100 mL). The combined aqueous extracts were acidified with 10% aqueous citric acid and extracted with EtOAc (3×100 mL). The organic extracts were combined, dried (MgSO₄), filtered and concentrated in vacuo to give tert-butyl N-[(2S)—N-Fmoc-asparty])-β-N-phenylglycinate as a white solid. ¹³C NMR (50 MHz, d₆-DMSO): δ 28.0, 36.7, 47.0, 50.4, 52.4, 67.0, 67.3, 82.3, 119.9, 125.2, 125.3, 127.1, 127.7, 127.8, 128.8, 130.1, 141.2, 142.8, 143.7, 143.9, 156.1, 167.6, 171.6, 174.5.

Step 5: Solid phase amino acid synthesis using the above Fmoc protected dipeptide followed by cyclization on the resin and cleavage gave cyclo-[N-phenylglycine-Gln-Asn-(D)-Asp]-Lys-Ser-NH₂.

Experiment 22

This experiment illustrates a synthesis of 2-(2'-phenyl-ethyl)-β-N-acetyl-lysine amide and its hydrochloride salt:

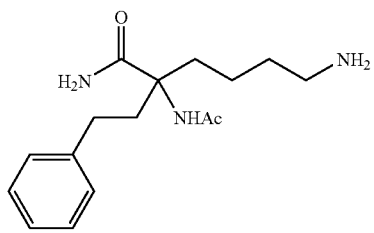

BRI 7001

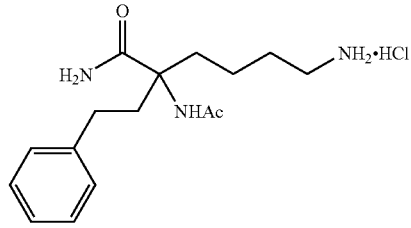

BRI 7002

Step 1: To a mixture of sodium metal (138 mg, 5.98 mmol) in dry ethanol (16 mL) was added 2-cyano-4-(phenethyl) ethylbutanoate (1.0 g, 4.6 mmol) and the mixture was stirred at room temperature for 30 min. 4-Bromo-but-1-ene (0.6 mL, 6 mmol) was then added and the mixture was heated at reflux for 16 hours. The resulting suspension was cooled to room temperature, concentrated under reduced pressure and diluted with ether (100 mL) and NH₄Cl (100 mL of a saturated aqueous solution). The aqueous layer was separated and extracted with ether (3×50 mL). The organic layers were combined, dried (MgSO₄), filtered and concentrated to give a light brown oil. Column chromatography (silica, 20% ether/petrol elution) afforded ethyl 2-cyano-2-(2'-phenethyl)-hex-5-enoate as a clear, colorless oil. ¹H NMR (200 MHz, CDCl₃): δ 1.35 (t, J=7.0 Hz, 3H), 1.82-2.45 (m, 6H), 2.65 (td, J=12.4 Hz and 7.0 Hz, 1H), 2.90 (td, J=12.4 Hz and 7.0 Hz, 1H), 4.24 (q, J=7.0 Hz, 2H), 5.00-5.13 (m, 2H), 5.67-5.76 (m, 1H), 7.15-7.35 (m, 5H).

Step 2: A mixture of the above olefin (0.72 g, 2.65 mmol), LiOH (10.6 mL, 1.0 M, 10.6 mmol) and THF (50 mL) was stirred at room temperature for 18 hours. The reaction mixture was diluted with ether (100 mL) and water (100 mL) and the phases separated. The aqueous layer was acidified to ca, pH 2 with 2 M aqueous HCl solution and transferred to a separating funnel containing ether (100 mL). The separated aqueous layer was extracted with ether (3×50 mL). The organic fractions were combined, dried (MgSO₄), filtered and concentrated under reduced pressure to afford 2-cyano-2-(2'-phenethyl)-5-hexenoic acid as a viscous, colorless oil. This material was used in the next reaction without further purification. MS (APCI) m/z 244 (M⁺+1, 55%), 242 (M⁺−1, 63%).

Step 3: Diphenyl phosphoryl azide (2.75 mL, 12.8 mmol) and triethylamine (1.75 mL, 12.6 mmol) were added to a solution of the above acid (2.6 g, 10.7 mmol) in toluene (35 mL). The solution was heated at 100 C for 1 hour after which time tert-butanol (35 mL) was added. The mixture was heated at 100 C for additional 2 hours, cooled to room temperature and concentrated under reduced pressure. The resulting yellow oil was diluted with ether (300 mL) and water (300 mL). The organic layer was separated, washed successively with citric acid (100 mL of a 5% aqueous solution), NaHCO₃ (100 mL of a 5% aqueous solution) and brine (100 mL), dried (MgSO₄), filtered and concentrated to give a yellow oil. Column chromatography (silica, 2% ethyl acetate/chloroform elution) gave 2-(N-boc-amino)-2-(2⁺-phenethyl)-5-hexeno-nitrile as a colorless oil. MS (APCI) m/z 316 (M⁺+1, 5%), 313 (M⁺−1, 2%). ¹³C NMR (50 MHz, CDCl₃): δ 28.4, 30.5, 36.3, 38.9, 54.9, 116.3, 119.7, 126.6, 128.4, 128.8, 136.3, 140.1, 153.5.

Step 4: NaOH (9.2 mL, 1.0 M) and H₂O₂ (38 mL of a 30% (v/v) aqueous solution) were added to a solution of the above nitrile compound (523 mg, 1.93 mmol) in ethanol (20 mL) at 0 C. The reaction mixture was stirred at 0 C for 30 min and at room temperature for 18 hours. The ethanol was removed under reduced pressure and the residue was diluted with ether (100 mL) and brine (100 mL). The aqueous layer was separated and extracted with ether (4×20 mL). The organic layers were combined, dried (MgSO$_4$), filtered and concentrated to afford 2-(N-Boc-amino)-2-(2'-phenethyl)-5-hexenamide as a colorless sticky foam. This material was used in the next reaction without further purification R$_f$ 0.3 (30% ethyl acetate/petrol elution). MS (APCI) m/z 333 (M$^+$+1, 5%), 233 (100%).

Step 5: Trifluoroacetic acid (2 mL) was added to a solution of the above amide (480 mg, 1.44 mmol) in dichloromethane (5 mL), and the mixture was stirred at room temperature for 35 min. The reaction mixture was concentrated to afford 2-amino-2-(2'-phenethyl)-5-hexenamide as a red-brown oil. This material was used in the next reaction without further purification. MS (APCI) m/z 233 (M$^+$+1, 100%).

Step 6: Acetic anhydride (2.5 mL) was added to a solution of the above amine (335 mg, 1.44 mmol) in pyridine (2.5 mL) and stirred at room temperature for 21 hours. The resulting red-brown reaction mixture was concentrated under reduced pressure. Column chromatography (silica, 80% ethyl acetate/petrol elution, R$_f$ 0.36) gave (N-acetyl-amino)-2-(2'-phenethyl)-5-hexenamide as a straw colored foam. $^{13}$C NMR (50 MHz, CDCl$_3$): δ 24.2, 28.3, 30.4, 35.2, 37.8, 64.0, 115.2, 126.1, 128.4, 128.5, 137.4, 141.1, 169.4, 175.3.

Step 7: 9-BBN (4.6 mL, 0.5 M solution in THF, 2.30 mmol) was added dropwise to a solution of the above olefin (130 mg, 0.47 mmol) in dry THF (2 ml). The reaction mixture was stirred at ambient temperature for 18 hours. The mixture was cooled to 0 C and water (0.5 mL), NaOAc (5 mL of a 5.0 M aqueous solution) and H$_2$O$_2$ (5 mL) were added successively. The resulting mixture was stirred at room temperature for 2 hours and diluted with ethyl acetate (30 mL) and brine (30 mL). The aqueous layer was separated and extracted with ethyl acetate (3×10 mL). The organic fractions were combined, dried (MgSO$_4$), filtered and concentrated under reduced pressure to give a light yellow oil. Column chromatography (silica, 5% MeOH/ethyl acetate elution, R$_f$ 0.4) gave 2-(N-acetyl-amino)-2-(2'-phenethyl)-6-hydroxy-hexanamide as a colorless, sticky foam. MS (APCI) m/z 293 (M$^+$+1, 35%), 291 (M$^+$–1, 35%).

Step 8: Triethylamine (0.1 mL, 0.72 mmol) and methanesulfonyl chloride (0.05 mL, 0.65 mmol) were added to a solution of the above alcohol (88 mg, 0.30 mmol) in dichloromethane (2 mL) at 0 C. The resulting mixture was stirred at ambient temperature for 19 hours and diluted with ethyl acetate (30 mL) and brine (30 mL). The aqueous layer was separated and extracted with ethyl acetate (3×10 mL). The organic layers were combined, dried (MgSO$_4$), filtered and concentrated under reduced pressure to give 2-(N-acetyl-amino)-2-(2'-phenethyl)-6-methanesulfonyloxy-hexanamide as a tan colored residue. The crude product was used in the next reaction without further purification. MS (APCI) m/z 371 (M$^+$+1, 45%), 369 (M$^+$–1, 5%).

Step 9: A solution of the above mesylate (110 mg, 0.30 mmol) and sodium azide (54 mg, 0.83 mmol) in dry DMF (2 mL) was heated at 60 C to 65 C for 19.5 hours. The orange colored suspension was cooled to room temperature, concentrated and diluted with ethyl acetate (30 mL) and brine (30 mL). The aqueous layer was separated and extracted with ethyl acetate (4×10 mL). The organic fractions were combined, dried (MgSO$_4$), filtered and concentrated to afford 2-(N-acetyl-amino)-2-(2'-phenethyl)-6-azido-hexanamide as a tan colored oil. This material was used in the next reaction without further purification. $^1$H NMR (200 MHz, CDCl$_3$): δ 1.20-1.78 (m, 6H), 1.92 (s, 3H), 2.20-3.02 (m, 1H), 3.12-3.30 (m, 2H), 5.57 (s, 1H), 5.90 (s, 1H), 6.72 (s, 1H), 7.04-7.30 (m, 5H).

Step 10: A suspension of the above azide (95 mg, 0.30 mmol) and 10% Pd on C (18.4 mg) in methanol (2 mL) was hydrogenated at room temperature and atmospheric pressure for 21 hours. The black suspension was filtered through a small plug of silica-Celite which was flushed with several portions of methanol (ca. 30 mL). Concentration of the filtrate afforded a light tan colored oil. Column chromatography (silica, 10% triethylamine/methanol elution, R$_f$ 0.22) gave 2-(2'-phenylethyl)-β-N-acetyl-lysine amide as a clear, colorless oil. MS (APCI), m/z 292 (M$^+$+1, 100%) 290 (M$^+$–1, 30%). $^1$H NMR (200 MHz, d$_4$-MeOD): δ 1.10-1.60 (m, 4H), 1.73-1.90 (m, 1H), 1.95 (s, 3H), 1.95-2.35 (m, 2H), 2.40-2.80 (m, 5H), 7.10-7.35 (m, 5H).

A small quantity of the amine was converted to the corresponding hydrochloride salt derivative by adding 0.5 M aqueous HCl solution to the amine and concentrating the mixture under reduced pressure.

Experiment 23

This experiment illustrates a synthesis of 4,4'-bis-(3-[(m-carboxyphenoxy)methyl]-2-pyridone):

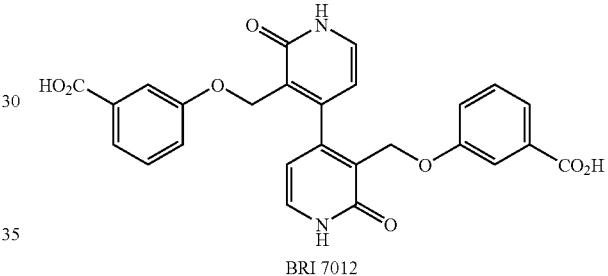

BRI 7012

Step 1: Solid NaBH$_4$ (28 mg, 0.74 mmol) was added in one portion to a solution of 3-formyl-4-iodo-2-methoxypyridine (prepared according to the method of Fang et al., *J. Org. Chem.*, 1994, 59, 6142) (98 mg, 0.37 mmol) in methanol (4 mL) at −5 C. Vigorous bubbling was observed and the yellow reaction solution turned colorless. The reaction was immediately quenched by the addition of water (2 mL) and the methanol was removed under reduced pressure. The resulting residue was diluted with ethyl acetate (20 mL) and water (20 mL). The aqueous layer was separated and extracted with ethyl acetate (3×10 mL). The organic fractions were combined, dried (MgSO$_4$), filtered and concentrated to give 3-(hydroxymethyl)-4-iodo-2-methoxypyridine as a colorless, crystalline solid. This material was used in the next reaction without further purification. R$_f$ 0.4 (30% ethyl acetate/petrol elution). MS (APCI, m/z 266 (M$^+$+1, 100%). $^1$H NMR (200 MHz, CDCl$_3$): δ 3.98 (s, 3H), 4.80 (s, 2H), 7.34 (d, J=4.0 Hz, 1H), 7.70 (d, J=4.0 Hz, 1H).

Step 2: Methanesulfonyl chloride (0.5 mL, 6.4 mmol) was added dropwise to a solution of the above alcohol (373 mg, 1.41 mmol) and triethylamine (0.95 mL, 6.8 mmol) in dichloromethane (9.4 mL) at 0 C. The resulting mixture was stirred at ambient temperatures for 15 hours and diluted with ethyl acetate (150 mL) and brine (150 mL). The aqueous layer was separated and extracted with ethyl acetate (3×50 mL). The organic fractions were combined, dried (MgSO$_4$), filtered and concentrated under reduced pressure to afford 3-(chloromethyl)-4-iodo-2-methoxypyridine as a light tan, crystalline solid. This material was used in the next step without further purification. MS (APCI) m/z 284 (M$^+$+1, 100%). $^1$H NMR (200 MHz, CDCl$_3$): δ 3.95 (s, 3H), 4.65 (s, 2H), 7.28 (d, J=4.0 Hz, 1H), 7.65 (d, J=4.0 Hz, 1H).

Step 3: The sodium salt of methyl-3-hydroxybenzoate (372 mg, 2.14 mmol) was added in one portion to a solution of the above chloride (399 mg, 1.41 mmol) in dry DMF (7 mL). The orange colored reaction mixture was stirred at room temperature for 18 hours and diluted with ethyl acetate (150 mL) and water (150 mL). The aqueous layer was separated and extracted with ethyl acetate (3×30 mL). The organic layers were combined, dried (MgSO$_4$), filtered and concentrated to give a brown oil. Column chromatography of this oil (silica, 30% ether/petrol elution, R$_f$0.35) gave 4-iodo-2-methoxy-3-{[(m-carbomethoxy)phenoxy]methyl}-pyridine as a colorless oil. MS (APCI), m/z 400 (M$^+$+1, 40%). $^1$H NMR (200 MHz, CDCl$_3$): δ 3.92 (s, 3H), 3.96 (s, 3H), 5.20 (s, 2H), 7.15-7.42 (m, 3H), 7.62-7.80 (m, 3H).

Step 4: A suspension of the above iodide (0.5 g, 1.25 mmol), Pd(PPh$_3$)$_4$ (141 mg. 0.13 mmol), K$_2$CO$_3$ (518 mg, 3.76 mmol), diboron pinacol ester (159 mg, 0.63 mmol) in DMF (7.6 mL) was heated at 80 C, protected from light, for 16 hours. The dark brown reaction mixture was cooled to room temperature and diluted with ethyl acetate (150 mL) and water (150 mL). The aqueous layer was separated and extracted with ethyl acetate (3×25 mL). The organic layers were combined, dried (MgSO$_4$), filtered and concentrated under reduced pressure to give a brown oil. Column chromatography (silica, 50% ethyl acetate/petrol elution, R/0.57) of this oil gave 4,4'-bis-2-methoxy-3-{[(m-carbomethoxy)phenoxy]methyl}-pyridine as a foam. MS (APCI) m/z 545 (M$^+$+1, 100%).

Step 5: A solution of the above dimeric diester (277 mg, 0.51 mmol) in LiOH (10 mL, 1.0 M) and THF (10 mL) was stirred at room temperature for 18 hours. The crude reaction mixture was then diluted with ether (75 mL) and the phases separated. The aqueous layer was acidified to pH 2 with 2.0 M aqueous HCl solution and then extracted with ethyl acetate (4×50 mL). The organic fractions were combined, dried (MgSO$_4$), filtered and concentrated to give 4,4'-bis-2-methoxy-3-{[(m-carboxy)phenoxy]methyl}-pyridine as a colorless solid. This material was used in the next step without further purification. MS (APCI) m/z 517 (M$^+$+1, 100%), 515 (M$^+$-1, 100%).

Step 6: Hydrolysis of the above methoxy-pyridine gave 4,4'-bis-{3-[(m-carboxyphenoxy)methyl]-2-pyridone}.

Example 12

This example illustrates Fc receptor modulating activity of a tripeptide and a hexapeptide.

Peptide Production.

Solid phase peptide synthesis (SPPS) was used to produce an acetylated tripeptide of sequence GKS and hexapeptide of sequence FQNGKS (SEQ ID NO:16). See for example, Merrifield, J. Am. Chem. Soc., 1963, 85, 2419, and Merrifield et al., Anal. Chem., 1966, 38, 1905. The peptides were synthesized on a 432A synergy Peptide Synthesizer. Construction of peptides was based on Fmoc chemistry (Carpino et al., J. Org. Chem. 1972, 37, 3404), while amidated C-terminal resins were used as starting material. Once construction of peptides was complete, an active ester was generated to react with peptide and produce an acetylated N-terminus.

Standard TFA cleavage procedures (Fmoc compatible) were performed and the product were purified using reversed-phase high-performance liquid chromatography (RP-HPLC). (See for example, Mant, C. T. and Hodges, R. S. eds, 1991, "High-Performance Liquid Chromatography of Peptides and Proteins: Separation, Analysis and Confirmation," CRC Press, Boca Raton, Fla.). The two mobile phases were, 0.1% trifluoroacetic acid (TFA)/99% H$_2$O and 0.1% TFA/60% CH$_3$CN/39.9% H$_2$O. The stationary phase was a prep grade C8 Brownlee Column. Mass spectral analysis was obtained on the final product, which confirmed identity and a purity of greater than 95% for both peptides.

Analysis of FcγRIIa binding in the presence of hexa or tripeptides

Analysis of the interaction between the baculovirus derived FcγRIIa and peptide (tripeptide: GKS, hexapeptide: FQNGKS (SEQ ID NO:16)) was performed using a BIAcore 2000 biosensor (Pharmacia Biotech, Uppsala, Sweden) at 22 C in Hepes buffered saline (HBS: 10 mM Hepes, (pH 7.4), 150 mM NaCl, 3.4 mM EDTA, 0.005% Surfactant P20 (Pharmacia). Monomeric human IgG1, IgG3, and IgE (50 ?g/mL), were covalently coupled to the carboxymethylated dextran surface of the CM-5 sensor-chip (BIAcore, Uppsala, Sweden) using the amine coupling protocol (BIAcore, Uppsala, Sweden). A channel with no Ig attached was also chemically treated using the coupling protocol. FcγRIIa at a fixed concentration (50 µg/mL, 50% binding concentration) was mixed with a range of peptide concentrations (see FIGS. 28 and 29), for 1 hour at 22 C before the mixture was injected over the sensor-chip surface for 1 min at 20 L/min followed by a 3 minute dissociation phase. At the conclusion of the concentration dependence measurements all surfaces were regenerated using 50 mM diethylamine (pH 11.5), 1 M NaCl. The total response measured for each concentration of peptide was determined and plotted against the peptide concentration. The non-specific binding responses (IgE channel) were subtracted from binding to IgG1 or IgG3.

Results

Figure 28:
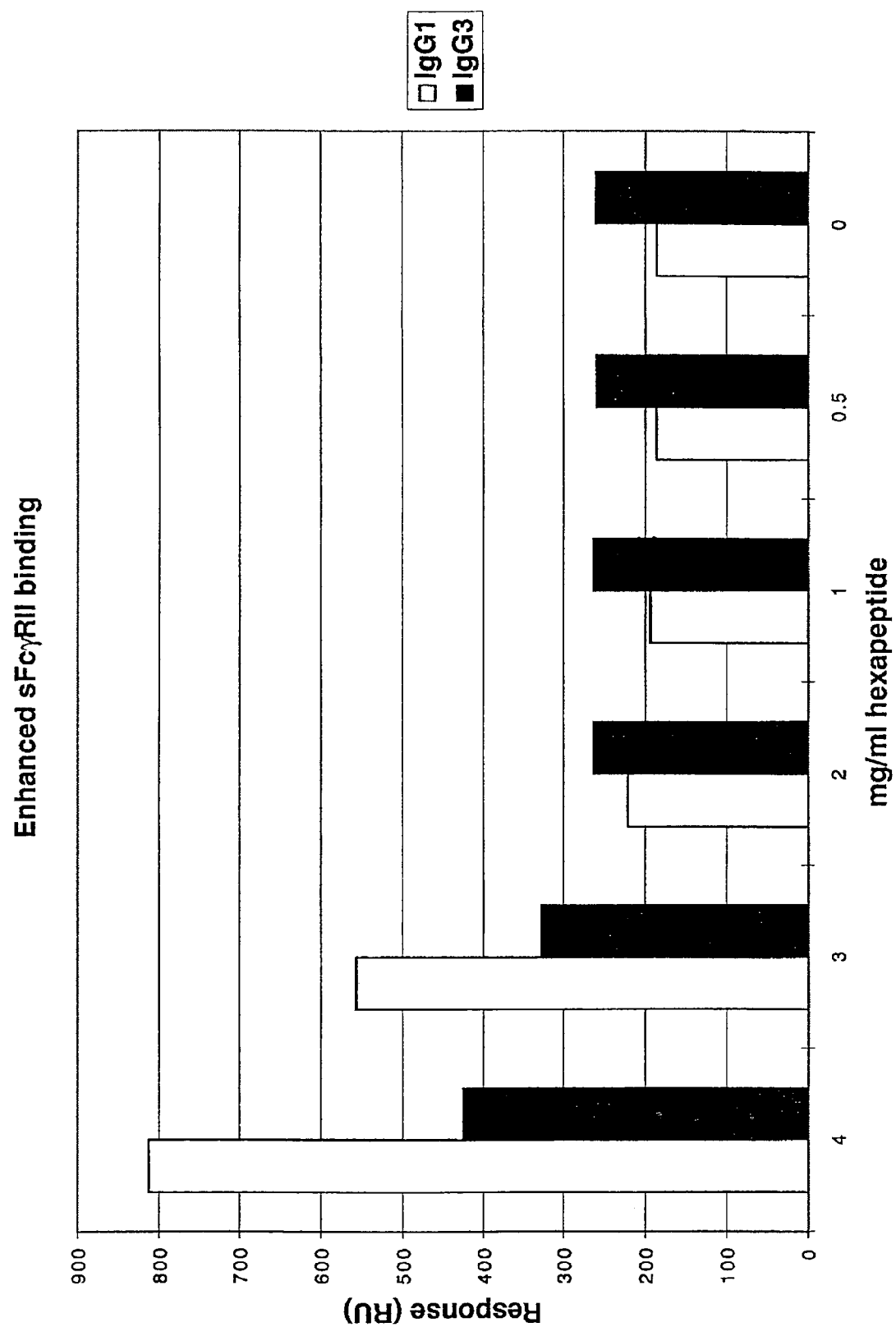

Using the sensitivity of surface plasmon resonance (SPR), the binding of soluble FcγRIIa to IgG1 and IgG3 was examined in the presence of a hexapeptide (FQNGKS (SEQ ID NO:16)) or tripeptide (GKS). In the presence of the hexapeptide, the binding of soluble FcγRIIa to the immobilized IgG1 was enhanced four fold and 1.6 fold for interaction with IgG3 (FIG. 28). However, the interaction of soluble FcγRIIa with IgG1 or IgG3 in the presence of the tripeptide was inhibited over a similar peptide concentration range (0-4 mg/mL, FIG. 29).

Example 13

This example illustrates platelet aggregation inhibition activity of some of the compounds of the present invention. The procedure generally involves adding the compound to a mixture of the platelets and HAGG. Without being bound by any theory, it is believed that this procedure shows the ability of the compound to inhibit a platelet aggregate formation as well as its ability to break apart the platelet aggregates which have formed prior to the addition of the compound.

Platelets express a single class of gamma receptors, FcγRIIa. Following the cross-linking of FcγRIIa, platelets undergo a variety of biochemical and cellular modifications that culminate in aggregation. The capacity of the compounds to inhibit platelet activation was measured using an assay that specifically measures platelet aggregation.

Material and Method.

Platelets were isolated as follows: 30 mL of fresh whole blood was collected into citrated collection vials and centrifuged at 1000 rpm for ten minutes. The platelet rich plasma was separated and centrifuged at 2000 rpm for five minutes in four tubes. The supernatants were removed and the platelets were gently resuspended in 2 mL of Tyrodes buffer per tube (137 mM NaCl, 2.7 mM KCl, 0.36 mM $NaH_2PO_4$, 0.1% dextrose, 30 mM sodium citrate, 1.0 mM $MgCl_2.6H_2O$, pH 6.5) and centrifuged again at 2000 rpm for five minutes. The supernatants were again removed and platelets were resuspensed in 0.5 mL of Hepes containing Tyrodes buffer per tube (137 mM NaCl, 2.7 mM KCl, 0.36 mM $NaH_2PO_4$, 0.1% dextrose, 5 mM Hepes, 2 mM $CaCl_2$ 1.0 mM $MgCl_2.6H_2O$, pH 7.35). The platelet count was determined using a haematolog analyzer (Coulter) and adjusted to a concentration of approximately $100\times10^5$ platelets/mL using the Hepes containing Tyrodes buffer.

For each aggregation experiment, a mixture of 50 μL of the Fc receptor agonist, heat aggregated gamma globulin ("HAGG", 200 □g/mL) or collagen (2 μg/mL) was incubated with 50 μL of phosphate buffered saline ("PBS": 3.5 mM $NaH_2PO_4$, 150 mM NaCl) or BRI compound (5 mg/mL in PBS) for 60 minutes at room temperature. The assay was then performed using a two cell aggregometer at 37 C as follows: glass cuvettes were placed in holders and prewarmed to 37 C and 400 μL of the platelet suspension added. After a stable baseline was reached, 100 μL of HAGG:PBS, HAGG:BRI compound or collagen:PBS, collagen:BRI compound were added to the platelet suspension. The subsequent aggregation of the platelets was monitored for 15 minutes or until aggregation was complete. The rate of aggregation was determined by measuring the gradient of the aggregation slope.

Results

The ability of compounds (BRI6855, BRI6803, BRI6813, BRI6864, BRI6856, BRI6868, BRI7002) to inhibit the HAGG induced Fc□RIIa dependent aggregation was examined. The rate of platelet aggregation, measured as the ratio of increased light transmission (y) over time (x), see for example, FIGS. 30 and 31, in the presence of compounds BRI6855, BRI6803, BRI6813, BRI6864 and BRI6856 was reduced compared to the rate achieved when using the FcγRIIa agonist, heat aggregated gamma globulin (100%), see Table 7. Compounds BRI6868 and BRI7002 did not appear to significantly inhibit the rate of platelet activation, Table 7. Compounds BRI6855 and BRI6803 reduced HAGG induced platelet aggregation but did not significantly inhibit the collagen induced platelet aggregation. This indicates activities of BRI6855 and BRI6803 are specific for HAGG.

TABLE 7

Rate of platelet activation in the presence of FcγRIIa agonists or antagonists

| Compound | Rate of platelet aggregation (%) | |
|---|---|---|
| | Expt. 1 | Expt. 2 |
| HAGG + PBS | 100 | 100 |
| HAGG + BRI6855 | 56 | 57 |
| HAGG + BRI6803 | 56 | 58 |
| HAGG + BRI6813 | 82 | 93 |
| HAGG + BRI6864 | 63 | NT |
| HAGG + BRI6856 | 82 | 50 |
| HAGG + BRI6868 | 113 | 116 |
| HAGG + BRI7002 | 92 | NT |
| Collagen + PBS | 100 | 100 |
| Collagen + BRI6855 | 100 | NT |
| Collagen + BRI6803 | 73 | NT |

100% is the value of the slope obtained for platelet aggregation using HAGG.
Note that in every experiment effect of compound was simultaneously compared to HAGG induced aggregation.
NT = Not Tested.

100% is the value of the slope obtained for platelet aggregation using HAGG.

Note that in every experiment effect of compound was simultaneously compared to HAGG induced aggregation.

NT=Not Tested.

Example 14

This example illustrates platelet aggregation inhibition activity of some of the compounds of the present invention. The procedure generally involves adding HAGG being added to a mixture of the platelets and the compound. Without being bound by any theory, it is believed that unlike Example 13, this method only shows the ability of the compound to inhibit the formation of a platelet aggregates.

Material and Method.

Experimental procedure of Example 13 was used to isolate platelets and determine the platelet count.

Unlike Example 13, the platelet aggregation assay was performed by adding 50 mL of PBS or BRI compound to the platelet suspension. After about one minute, 50 mL of agonist (HAGG, collagen or ADP) were added to the platelet suspension. The subsequent aggregation of the platelets was monitored for 10-15 minutes or until aggregation was complete. The rate of aggregation was determined by measuring the gradient of the aggregation slope.

Results

The ability of compound BRI6728 to inhibit the HAGG induced FcγRIIa dependent aggregation was examined. The rate of platelet aggregation, measured as the ratio of increased light transmission (y) over time (x), see for example, FIG. 32, in the presence of titrating amounts of the compound BRI6728 was reduced compared to the rate achieved when using the FcγRIIa agonist, heat aggregated gamma globulin (100%), see FIG. 32. Results of platelet aggregation using other compounds are shown on Table 8.

TABLE 8

Platelet aggregation in the presence of a various compounds.

| Compound | Amount of platelet aggregation (%) | |
|---|---|---|
| | Expt. 1 | Expt. 2 |
| PBS | 100 | NT |
| BRI6855 | 81 | NT |
| BRI6864 | 41 | NT |
| BRI6829 | 35 | NT |
| BRI6816 | 0 | 0 |
| BRI6734 | 0 | NT |
| BRI6727 | 0 | NT |

TABLE 8-continued

Platelet aggregation in the presence of a various compounds.

| | Amount of platelet aggregation (%) | |
|---|---|---|
| Compound | Expt. 1 | Expt. 2 |
| BRI6728 | 0 | 0 |
| BRI6822 | 0 | 0 |
| BRI6817 | 75 | NT |

100% is the amount of platelet aggregation obtained using PBS.
NT = Not Tested.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

LENGTHY TABLES

The patent contains a lengthy table section. A copy of the table is available in electronic form from the USPTO web site (http://seqdata.uspto.gov/?pageRequest=docDetail&DocID=US07553809B2). An electronic copy of the table will also be available from the USPTO upon request and payment of the fee set forth in 37 CFR 1.19(b)(3).

What is claimed is:

1. A method of reducing IgG-mediated tissue damage and inflammation associated with rheumatoid arthritis, the method comprising:
    administering to a patient in need of such treatment, a compound in an amount effective to inhibit FcγRIIa receptor binding of immunoglobulin,
    wherein the FcγRIIa receptor is a dimer of two FcR monomers, each comprising domains 1 (D1) and 2 (D2), and
    wherein the compound binds to a surface an immunoglobulin-binding site of the FcγRIIa receptor wherein the surface comprises a structure defined by the conformation of amino acid residues 155, 156, 158-160, 113-116, 129, 131, 133 and 134 of SEQ ID NO:3.

2. A method of reducing IgG-mediated tissue damage and inflammation associated with rheumatoid arthritis, the method comprising:
    administering to a patient in need of such treatment, a compound in an amount effective to inhibit FcγRIIa receptor binding of immunoglobulin,
    wherein the FcγRIIa receptor is a dimer of two FcR monomers, each comprising domains 1 (D1) and 2 (D2), and
    wherein the compound binds to a surface on an upper groove of the FcγRIIa receptor, wherein the surface comprises a structure defined by the conformation of amino acid residues 117-121, 125-129, 150-154 and 157-161 of SEQ ID NO:3.

3. The method of claim 2, wherein the structure comprises an FG loop.

4. A method of reducing IgG-mediated tissue damage and inflammation associated with rheumatoid arthritis, the method comprising:
    administering to a patient in need of such treatment, a compound in an amount effective to inhibit FcγRIIa receptor binding of immunoglobulin,
    wherein the FcγRIIa receptor is a dimer of two FcR monomers, each comprising domains 1 (D1) and 2 (D2), and
    wherein the compound binds to a surface on a dimerization interface of the FcR monomers of the FcγRIIa receptor wherein the surface comprises a structure defined by the conformation of amino acid residues 117-131 and 150-164 of SEQ ID NO:3.

5. A method of reducing IgG-mediated tissue damage and inflammation associated with rheumatoid arthritis, the method comprising:
    administering to a patient in need of such treatment, a compound in an amount effective to inhibit FcγRIIa receptor binding of immunoglobulin, wherein the FcγRIIa receptor is a dimer of two FcR monomers, each comprising domains 1 (D1) and 2 (D2), and wherein the compound binds to a surface on the interface between D1 and D2 of the FcγRIIa receptor comprising a structure defined by the conformation of amino acid residues 17-20 of SEQ ID NO:3.

6. A method of reducing IgG-mediated tissue damage and inflammation associated with rheumatoid arthritis, the method comprising:

administering to a patient in need of such treatment, a compound in an amount effective to inhibit FcγRIIa receptor binding of immunoglobulin, wherein the FcγRIIa receptor is a dimer of two FcR monomers, each comprising domains 1 (D1) and 2 (D2), and wherein the compound binds to a surface on a cleft region between D1 and D2 of the FcγRIIa receptor, wherein the surface comprises a structure defined by the conformation of amino acid residues 12-14, 6-10, 77-80, 93-96 and 101 of SEQ ID NO:3.

* * * * *

```
                              SEQUENCE LISTING

<160> NUMBER OF SEQ ID NOS: 15

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence:PRIMER

<400> SEQUENCE: 1
tacgaattcc tatggagacc caaatgtctc                                       30

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence:PRIMER

<400> SEQUENCE: 2
cattctagac tattggacag tgatggtcac                                       30

<210> SEQ ID NO 3
<211> LENGTH: 171
<212> TYPE: PRT
<213> ORGANISM: Homo sapiens

<400> SEQUENCE: 3

Ala Pro Pro Lys Ala Val Leu Lys Leu Glu Pro Pro Trp Ile Asn Val
 1               5                  10                  15

Leu Gln Glu Asp Ser Val Thr Leu Thr Cys Gln Gly Ala Arg Ser Pro
                20                  25                  30

Glu Ser Asp Ser Ile Gln Trp Phe His Asn Gly Asn Leu Ile Pro Thr
            35                  40                  45

His Thr Gln Pro Ser Tyr Arg Phe Lys Ala Asn Asn Asn Asp Ser Gly
        50                  55                  60

Glu Tyr Thr Cys Gln Thr Gly Gln Thr Ser Leu Ser Asp Pro Val His
```

-continued

```
                65                  70                  75                  80
Leu Thr Val Leu Phe Glu Trp Leu Val Leu Gln Thr Pro His Leu Glu
                    85                  90                  95

Phe Gln Glu Gly Glu Thr Ile Met Leu Arg Cys His Ser Trp Lys Asp
                100                 105                 110

Lys Pro Leu Val Lys Val Thr Phe Phe Gln Asn Gly Lys Ser Gln Lys
                115                 120                 125

Phe Ser His Leu Asp Pro Thr Phe Ser Ile Pro Gln Ala Asn His Ser
            130                 135                 140

His Ser Gly Asp Tyr His Cys Thr Gly Asn Ile Gly Tyr Thr Leu Phe
145                 150                 155                 160

Ser Ser Lys Pro Val Thr Ile Thr Val Gln Val
                165                 170

<210> SEQ ID NO 4
<211> LENGTH: 8
<212> TYPE: PRT
<213> ORGANISM: Homo sapiens

<400> SEQUENCE: 4

Ala Pro Pro Lys Ala Val Leu Lys
  1               5

<210> SEQ ID NO 5
<211> LENGTH: 170
<212> TYPE: PRT
<213> ORGANISM: Homo sapiens

<400> SEQUENCE: 5

Ala Pro Pro Lys Ala Val Leu Lys Leu Glu Pro Gln Trp Ile Asn Val
  1               5                  10                  15

Leu Gln Glu Asp Ser Val Thr Leu Thr Cys Arg Gly Thr His Ser Pro
                 20                  25                  30

Glu Ser Asp Ser Ile Gln Trp Phe His Asn Gly Asn Leu Ile Pro Thr
             35                  40                  45

His Thr Gln Pro Ser Tyr Arg Phe Lys Ala Asn Asn Asn Asp Ser Gly
        50                  55                  60

Glu Tyr Thr Cys Gln Thr Gly Gln Thr Ser Leu Ser Asp Pro Val His
 65                  70                  75                  80

Leu Thr Val Leu Ser Glu Trp Leu Val Leu Gln Thr Pro His Leu Glu
                    85                  90                  95

Phe Gln Glu Gly Glu Thr Ile Val Leu Arg Cys His Ser Trp Lys Asp
                100                 105                 110

Lys Pro Leu Val Lys Val Thr Phe Phe Gln Asn Gly Lys Ser Lys Lys
                115                 120                 125

Phe Ser Arg Ser Ile Pro Asn Phe Ser Ile Pro Gln Ala Asn His Ser
            130                 135                 140

His Ser Gly Asp Tyr His Cys Thr Gly Asn Ile Gly Tyr Thr Leu Tyr
145                 150                 155                 160

Ser Ser Lys Pro Val Thr Ile Thr Val Gln
                165                 170

<210> SEQ ID NO 6
<211> LENGTH: 170
<212> TYPE: PRT
<213> ORGANISM: Homo sapiens

<400> SEQUENCE: 6
```

```
Ala Pro Pro Lys Ala Val Leu Lys Leu Glu Pro Gln Trp Ile Asn Val
 1               5                  10                  15

Leu Gln Glu Asp Ser Val Thr Leu Thr Cys Arg Gly Thr His Ser Pro
            20                  25                  30

Glu Ser Asp Ser Ile Gln Trp Phe His Asn Gly Asn Leu Ile Pro Thr
        35                  40                  45

His Thr Gln Pro Ser Tyr Arg Phe Lys Ala Asn Asn Asn Asp Ser Gly
    50                  55                  60

Glu Tyr Thr Cys Gln Thr Gly Gln Thr Ser Leu Ser Asp Pro Val His
65                  70                  75                  80

Leu Thr Val Leu Ser Glu Trp Leu Val Leu Gln Thr Pro His Leu Glu
                85                  90                  95

Phe Gln Glu Gly Glu Thr Ile Val Leu Arg Cys His Ser Trp Lys Asp
            100                 105                 110

Lys Pro Leu Val Lys Val Thr Phe Phe Gln Asn Gly Lys Ser Lys Lys
        115                 120                 125

Phe Ser Arg Ser Asp Pro Asn Phe Ser Ile Pro Gln Ala Asn His Ser
    130                 135                 140

His Ser Gly Asp Tyr His Cys Thr Gly Asn Ile Gly Tyr Thr Leu Tyr
145                 150                 155                 160

Ser Ser Lys Pro Val Thr Ile Thr Val Gln
                165                 170

<210> SEQ ID NO 7
<211> LENGTH: 261
<212> TYPE: PRT
<213> ORGANISM: Homo sapiens

<400> SEQUENCE: 7

Thr Thr Lys Ala Val Ile Thr Leu Gln Pro Pro Trp Val Ser Val Phe
 1               5                  10                  15

Gln Glu Glu Thr Val Thr Leu His Cys Glu Val Leu His Leu Pro Gly
            20                  25                  30

Ser Ser Ser Thr Gln Trp Phe Val Asn Gly Thr Ala Thr Gln Thr Ser
        35                  40                  45

Thr Pro Ser Tyr Arg Ile Thr Ser Ala Ser Val Asn Asp Ser Gly Glu
    50                  55                  60

Tyr Arg Cys Gln Arg Gly Leu Ser Gly Arg Ser Asp Pro Ile Gln Leu
65                  70                  75                  80

Glu Ile His Arg Gly Trp Leu Leu Leu Gln Val Ser Ser Arg Val Phe
                85                  90                  95

Thr Glu Gly Glu Pro Leu Ala Leu Arg Cys His Ala Trp Lys Asp Lys
            100                 105                 110

Leu Val Tyr Asn Val Leu Tyr Tyr Arg Asn Gly Lys Phe Lys Phe Phe
        115                 120                 125

His Trp Asn Ser Asn Leu Thr Ile Leu Lys Thr Asn Ile Ser His Asn
    130                 135                 140

Gly Thr Tyr His Cys Ser Gly Met Gly Lys His Arg Tyr Thr Ser Ala
145                 150                 155                 160

Gly Ile Ser Val Thr Val Lys Glu Leu Phe Pro Ala Pro Val Leu Asn
                165                 170                 175

Ala Ser Val Thr Ser Pro Leu Leu Glu Gly Asn Leu Val Thr Leu Ser
            180                 185                 190

Cys Glu Thr Lys Leu Leu Lys Gln Arg Pro Gly Leu Gln Leu Tyr Phe
```

-continued

```
                195                 200                 205
Ser Phe Tyr Met Gly Ser Lys Thr Leu Arg Gly Arg Asn Thr Ser Ser
    210                 215                 220

Glu Tyr Gln Ile Leu Thr Ala Arg Arg Glu Asp Ser Gly Leu Tyr Trp
225                 230                 235                 240

Cys Glu Ala Ala Thr Glu Asp Gly Asn Val Leu Lys Arg Ser Pro Glu
                245                 250                 255

Leu Glu Leu Gln Val
            260

<210> SEQ ID NO 8
<211> LENGTH: 174
<212> TYPE: PRT
<213> ORGANISM: Homo sapiens

<400> SEQUENCE: 8

Arg Thr Glu Asp Leu Pro Lys Ala Val Val Phe Leu Glu Pro Gln Trp
  1               5                  10                  15

Tyr Ser Val Leu Glu Lys Asp Ser Val Thr Leu Lys Cys Gln Gly Ala
                 20                  25                  30

Tyr Ser Pro Glu Asp Asn Ser Thr Gln Trp Phe His Asn Glu Ser Leu
             35                  40                  45

Ile Ser Ser Gln Ala Ser Ser Tyr Phe Ile Asp Ala Ala Thr Val Asn
     50                  55                  60

Asp Ser Gly Glu Tyr Arg Cys Gln Thr Asn Leu Ser Thr Leu Ser Asp
 65                  70                  75                  80

Pro Val Gln Leu Glu Val His Ile Gly Trp Leu Leu Leu Gln Ala Pro
                 85                  90                  95

Arg Trp Val Phe Lys Glu Glu Asp Pro Ile His Leu Arg Cys His Ser
                100                 105                 110

Trp Lys Asn Thr Ala Leu His Lys Val Thr Tyr Leu Gln Asn Gly Lys
            115                 120                 125

Asp Arg Lys Tyr Phe His His Asn Ser Asp Phe His Ile Pro Lys Ala
        130                 135                 140

Thr Leu Lys Asp Ser Gly Ser Tyr Phe Cys Arg Gly Leu Val Gly Ser
145                 150                 155                 160

Lys Asn Val Ser Ser Glu Thr Val Asn Ile Thr Ile Thr Gln
                165                 170

<210> SEQ ID NO 9
<211> LENGTH: 172
<212> TYPE: PRT
<213> ORGANISM: Homo sapiens

<400> SEQUENCE: 9

Val Pro Gln Lys Pro Lys Val Ser Leu Asn Pro Pro Trp Asn Arg Ile
  1               5                  10                  15

Phe Lys Gly Glu Asn Val Thr Leu Thr Cys Asn Gly Asn Asn Phe Phe
                 20                  25                  30

Glu Val Ser Ser Thr Lys Trp Phe His Asn Gly Ser Leu Ser Glu Glu
             35                  40                  45

Thr Asn Ser Ser Leu Asn Ile Val Asn Ala Lys Phe Glu Asp Ser Gly
     50                  55                  60

Glu Tyr Lys Cys Gln His Gln Gln Val Asn Glu Ser Glu Pro Val Tyr
 65                  70                  75                  80

Leu Glu Val Phe Ser Asp Trp Leu Leu Leu Gln Ala Ser Ala Glu Val
```

```
                    85                  90                  95
Val Met Glu Gly Gln Pro Leu Phe Leu Arg Cys His Gly Trp Arg Asn
            100                 105                 110

Trp Asp Val Tyr Lys Val Ile Tyr Lys Asp Gly Glu Ala Leu Lys
        115                 120                 125

Tyr Trp Tyr Glu Asn His Asn Ile Ser Ile Thr Asn Ala Thr Val Glu
    130                 135                 140

Asp Ser Gly Thr Tyr Tyr Cys Thr Gly Lys Val Trp Gln Leu Asp Tyr
145                 150                 155                 160

Glu Ser Glu Pro Leu Asn Ile Thr Val Ile Lys Ala
                165                 170

<210> SEQ ID NO 10
<211> LENGTH: 170
<212> TYPE: PRT
<213> ORGANISM: Homo sapiens

<400> SEQUENCE: 10

Ala Pro Pro Lys Ala Val Leu Lys Leu Glu Pro Pro Trp Ile Asn Val
1               5                   10                  15

Leu Gln Glu Asp Ser Val Thr Leu Thr Cys Gln Gly Ala Arg Ser Pro
            20                  25                  30

Glu Ser Asp Ser Ile Gln Trp Phe His Asn Gly Asn Leu Ile Pro Thr
        35                  40                  45

His Thr Gln Pro Ser Tyr Arg Phe Lys Ala Asn Asn Asn Asp Ser Gly
    50                  55                  60

Glu Tyr Thr Cys Gln Thr Gly Gln Thr Ser Leu Ser Asp Pro Val His
65                  70                  75                  80

Leu Thr Val Leu Ser Glu Trp Leu Val Leu Gln Thr Pro His Leu Glu
                85                  90                  95

Phe Gln Glu Gly Glu Thr Ile Met Leu Arg Cys His Ser Trp Lys Asp
            100                 105                 110

Lys Pro Leu Val Lys Val Thr Phe Phe Gln Asn Gly Lys Ser Gln Lys
        115                 120                 125

Phe Ser Arg Leu Asp Pro Thr Phe Ser Ile Pro Gln Ala Asn His Ser
    130                 135                 140

His Ser Gly Asp Tyr His Cys Thr Gly Asn Ile Gly Tyr Thr Leu Phe
145                 150                 155                 160

Ser Ser Lys Pro Val Thr Ile Thr Val Gln
                165                 170

<210> SEQ ID NO 11
<211> LENGTH: 170
<212> TYPE: PRT
<213> ORGANISM: Homo sapiens

<400> SEQUENCE: 11

Ala Pro Pro Lys Ala Val Leu Lys Leu Glu Pro Pro Trp Ile Asn Val
1               5                   10                  15

Leu Gln Glu Asp Ser Val Thr Leu Thr Cys Trp Gly Ala Arg Ser Pro
            20                  25                  30

Glu Ser Asp Ser Ile Gln Trp Phe His Asn Gly Asn Leu Ile Pro Thr
        35                  40                  45

His Thr Gln Pro Ser Tyr Arg Phe Lys Ala Asn Asn Asn Asp Ser Gly
    50                  55                  60

Glu Tyr Thr Cys Gln Thr Gly Gln Thr Ser Leu Ser Asp Pro Val His
```

```
                65                  70                  75                  80
Leu Thr Val Leu Phe Glu Trp Leu Val Leu Gln Thr Pro His Leu Glu
                    85                  90                  95
Phe Gln Glu Gly Glu Thr Ile Met Leu Arg Cys His Ser Trp Lys Asp
                100                 105                 110
Lys Pro Leu Val Lys Val Thr Phe Phe Gln Asn Gly Lys Ser Gln Lys
                115                 120                 125
Phe Ser His Leu Asp Pro Thr Phe Ser Ile Pro Gln Ala Asn His Ser
            130                 135                 140
His Ser Gly Asp Tyr His Cys Thr Gly Asn Ile Gly Tyr Thr Leu Phe
145                 150                 155                 160
Ser Ser Lys Pro Val Thr Ile Thr Val Gln
                165                 170

<210> SEQ ID NO 12
<211> LENGTH: 170
<212> TYPE: PRT
<213> ORGANISM: Homo sapiens

<400> SEQUENCE: 12

Ala Pro Pro Lys Ala Val Leu Lys Leu Glu Pro Pro Trp Ile Asn Val
1               5                   10                  15
Leu Gln Glu Asp Ser Val Thr Leu Thr Cys Trp Gly Ala Arg Ser Pro
                20                  25                  30
Glu Ser Asp Ser Ile Gln Trp Phe His Asn Gly Asn Leu Ile Pro Thr
            35                  40                  45
His Thr Gln Pro Ser Tyr Arg Phe Lys Ala Asn Asn Asn Asp Ser Gly
        50                  55                  60
Glu Tyr Thr Cys Gln Thr Gly Gln Thr Ser Leu Ser Asp Pro Val His
65                  70                  75                  80
Leu Thr Val Leu Phe Glu Trp Leu Val Leu Gln Thr Pro His Leu Glu
                    85                  90                  95
Phe Gln Glu Gly Glu Thr Ile Met Leu Arg Cys His Ser Trp Lys Asp
                100                 105                 110
Lys Pro Leu Val Lys Val Thr Phe Phe Gln Asn Gly Lys Ser Gln Lys
                115                 120                 125
Phe Ser Arg Leu Asp Pro Thr Phe Ser Ile Pro Gln Ala Asn His Ser
            130                 135                 140
His Ser Gly Asp Tyr His Cys Thr Gly Asn Ile Gly Tyr Thr Leu Phe
145                 150                 155                 160
Ser Ser Lys Pro Val Thr Ile Thr Val Gln
                165                 170

<210> SEQ ID NO 13
<211> LENGTH: 287
<212> TYPE: PRT
<213> ORGANISM: Homo sapiens

<400> SEQUENCE: 13

Met Asp Pro Lys Gln Thr Thr Leu Leu Cys Leu Val Leu Cys Leu Gly
1               5                   10                  15
Gln Arg Ile Gln Ala Gln Glu Gly Asp Phe Pro Met Pro Phe Ile Ser
                20                  25                  30
Ala Lys Ser Ser Pro Val Ile Pro Leu Asp Gly Ser Val Lys Ile Gln
            35                  40                  45
Cys Gln Ala Ile Arg Glu Ala Tyr Leu Thr Gln Leu Met Ile Ile Lys
```

```
                 50                  55                  60
Asn Ser Thr Tyr Arg Glu Ile Gly Arg Arg Leu Lys Phe Trp Asn Glu
 65                  70                  75                  80

Thr Asp Pro Glu Phe Val Ile Asp His Met Asp Ala Asn Lys Ala Gly
                 85                  90                  95

Arg Tyr Gln Cys Gln Tyr Arg Ile Gly His Tyr Arg Phe Arg Tyr Ser
                100                 105                 110

Asp Thr Leu Glu Leu Val Val Thr Gly Leu Tyr Gly Lys Pro Phe Leu
                115                 120                 125

Ser Ala Asp Arg Gly Leu Val Leu Met Pro Gly Glu Asn Ile Ser Leu
130                 135                 140

Thr Cys Ser Ser Ala His Ile Pro Phe Asp Arg Phe Ser Leu Ala Lys
145                 150                 155                 160

Glu Gly Glu Leu Ser Leu Pro Gln His Gln Ser Gly Glu His Pro Ala
                165                 170                 175

Asn Phe Ser Leu Gly Pro Val Asp Leu Asn Val Ser Gly Ile Tyr Arg
                180                 185                 190

Cys Tyr Gly Trp Tyr Asn Arg Ser Pro Tyr Leu Trp Ser Phe Pro Ser
                195                 200                 205

Asn Ala Leu Glu Leu Val Val Thr Asp Ser Ile His Gln Asp Tyr Thr
210                 215                 220

Thr Gln Asn Leu Ile Arg Met Ala Val Ala Gly Leu Val Leu Val Ala
225                 230                 235                 240

Leu Leu Ala Ile Leu Val Glu Asn Trp His Ser His Thr Ala Leu Asn
                245                 250                 255

Lys Glu Ala Ser Ala Asp Val Ala Glu Pro Ser Trp Ser Gln Gln Met
                260                 265                 270

Cys Gln Pro Gly Leu Thr Phe Ala Arg Thr Pro Ser Val Cys Lys
                275                 280                 285

<210> SEQ ID NO 14
<211> LENGTH: 171
<212> TYPE: PRT
<213> ORGANISM: Homo sapiens

<400> SEQUENCE: 14

Ala Ala Pro Pro Lys Ala Val Leu Lys Leu Glu Pro Pro Trp Ile Asn
 1               5                  10                  15

Val Leu Gln Glu Asp Ser Val Thr Leu Thr Cys Gln Gly Ala Arg Ser
                20                  25                  30

Pro Glu Ser Asp Ser Ile Gln Trp Phe His Asn Gly Asn Leu Ile Pro
                35                  40                  45

Thr His Thr Gln Pro Ser Tyr Arg Phe Lys Ala Asn Asn Asn Asp Ser
        50                  55                  60

Gly Glu Tyr Thr Cys Gln Thr Gly Gln Thr Ser Leu Ser Asp Pro Val
 65                  70                  75                  80

His Leu Thr Val Leu Ser Glu Trp Leu Val Leu Gln Thr Pro His Leu
                85                  90                  95

Glu Phe Gln Glu Gly Glu Thr Ile Met Leu Arg Cys His Ser Trp Lys
                100                 105                 110

Asp Lys Pro Leu Val Lys Val Thr Phe Phe Gln Asn Gly Lys Ser Gln
                115                 120                 125

Lys Phe Ser His Leu Asp Pro Thr Phe Ser Ile Pro Gln Ala Asn His
        130                 135                 140
```

-continued

```
Ser His Ser Gly Asp Tyr His Cys Thr Gly Asn Ile Gly Tyr Thr Leu
145                 150                 155                 160

Phe Ser Ser Lys Pro Val Thr Ile Thr Val Gln
                165             170

<210> SEQ ID NO 15
<211> LENGTH: 171
<212> TYPE: PRT
<213> ORGANISM: Homo sapiens

<400> SEQUENCE: 15

Ala Ala Pro Pro Lys Ala Val Leu Lys Leu Glu Pro Pro Trp Ile Asn
1               5                   10                  15

Val Leu Gln Glu Asp Ser Val Thr Leu Thr Cys Gln Gly Ala Arg Ser
                20                  25                  30

Pro Glu Ser Asp Ser Ile Gln Trp Phe His Asn Gly Asn Leu Ile Pro
            35                  40                  45

Thr His Thr Gln Pro Ser Tyr Arg Phe Lys Ala Asn Asn Asn Asp Ser
        50                  55                  60

Gly Glu Tyr Thr Cys Gln Thr Gly Gln Thr Ser Leu Ser Asp Pro Val
65                  70                  75                  80

His Leu Thr Val Leu Phe Glu Trp Leu Val Leu Gln Thr Pro His Leu
                85                  90                  95

Glu Phe Gln Glu Gly Glu Thr Ile Met Leu Arg Cys His Ser Trp Lys
            100                 105                 110

Asp Lys Pro Leu Val Lys Val Thr Phe Phe Gln Asn Gly Lys Ser Gln
        115                 120                 125

Lys Phe Ser His Leu Asp Pro Thr Phe Ser Ile Pro Gln Ala Asn His
    130                 135                 140

Ser His Ser Gly Asp Tyr His Cys Thr Gly Asn Ile Gly Tyr Thr Leu
145                 150                 155                 160

Phe Ser Ser Lys Pro Val Thr Ile Thr Val Gln
                165             170
```